US009382529B2

(12) United States Patent
Bauer et al.

(10) Patent No.: US 9,382,529 B2
(45) Date of Patent: Jul. 5, 2016

(54) PROCESSES FOR PRODUCING POLYUNSATURATED FATTY ACIDS IN TRANSGENIC ORGANISMS

(71) Applicant: BASF Plant Science GmbH, Ludwigshafen (DE)

(72) Inventors: Jörg Bauer, Limburgerhof (DE); Tom Wetjen, Mannheim (DE)

(73) Assignee: BASF Plant Science GmbH, Ludwigshafen (DE)

( * ) Notice: Subject to any disclaimer, the term of this patent is extended or adjusted under 35 U.S.C. 154(b) by 314 days.

(21) Appl. No.: 13/911,675

(22) Filed: Jun. 6, 2013

(65) Prior Publication Data

US 2013/0340103 A1 Dec. 19, 2013

Related U.S. Application Data

(62) Division of application No. 12/444,193, filed as application No. PCT/EP2007/060554 on Oct. 4, 2007, now Pat. No. 8,710,299.

(30) Foreign Application Priority Data

Oct. 6, 2006 (EP) .................................. 06121888

(51) Int. Cl.
  *C12N 9/00* (2006.01)
  *A23D 9/00* (2006.01)
  *C12N 9/02* (2006.01)
  *C12N 9/10* (2006.01)
  *C12N 15/82* (2006.01)
  *C12P 7/64* (2006.01)
  *A61K 38/00* (2006.01)
  *A23K 1/16* (2006.01)
  *A23K 1/18* (2006.01)

(52) U.S. Cl.
  CPC .. *C12N 9/93* (2013.01); *A23D 9/00* (2013.01); *A23K 1/164* (2013.01); *A23K 1/188* (2013.01); *C12N 9/0071* (2013.01); *C12N 9/0083* (2013.01); *C12N 9/1029* (2013.01); *C12N 15/8247* (2013.01); *C12P 7/6427* (2013.01); *C12P 7/6472* (2013.01); *A61K 38/00* (2013.01); *Y02P 20/52* (2015.11)

(58) Field of Classification Search
  None
  See application file for complete search history.

(56) References Cited

U.S. PATENT DOCUMENTS

| | | | |
|---|---|---|---|
| 5,614,393 | A | 3/1997 | Thomas et al. |
| 6,043,411 | A | 3/2000 | Nishizawa et al. |
| 6,087,124 | A | 7/2000 | Steinbrück et al. |
| 2007/0028326 | A1 | 2/2007 | Cirpus et al. |
| 2007/0224661 | A1 | 9/2007 | Cirpus et al. |
| 2008/0076166 | A1 | 3/2008 | Cirpus et al. |
| 2008/0160054 | A1 | 7/2008 | Heinz et al. |

FOREIGN PATENT DOCUMENTS

| | | |
|---|---|---|
| DE | 102 19 203 A1 | 4/2002 |
| EP | 0 794 250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A2 | 7/1996 |
| WO | WO-97/21340 A1 | 6/1997 |
| WO | WO-97/30582 A1 | 8/1997 |
| WO | WO-98/01572 A1 | 1/1998 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-99/64616 A2 | 12/1999 |
| WO | WO-00/12720 A2 | 3/2000 |
| WO | WO-00/21557 A1 | 4/2000 |
| WO | WO-01/59128 A2 | 8/2001 |
| WO | WO-02/08401 A2 | 1/2002 |
| WO | WO-02/44320 A2 | 6/2002 |
| WO | WO-02/077213 A2 | 10/2002 |
| WO | WO-2005/012316 A2 | 2/2005 |
| WO | WO-2005/083053 A2 | 9/2005 |
| WO | WO-2006/069710 A1 | 7/2006 |
| WO | WO 2006069710 A1 * | 7/2006 |

OTHER PUBLICATIONS

Derelle E et al. Genome analysis of the smallest free-living eukaryote Ostreococcus tauri unveils many uniquie features. 2006. PNAS. vol. 103, No. 31. pp. 11647-11652.*

Palenik B et al. The tiny eukaryote Ostreococcus provides genomic insights into the paradox of the plankton speciation. 2007. PNAS. vol. 104, No. 18. pp. 7705-7710.*

Worden AZ et al. Assessing the dynamics and ecology of marine picophytoplankton: The importance of the eukaryotic component. 2004. Limnol. Oceanogr. 49(1). pp. 168-179.*

Poulos, A., "Very Long Chain Fatty Acids in Higher Animals—A Review", Lipids, vol. 30, No. 1, (1995), pp. 1-16.

Horrocks, L., et al., "Health Benefits of Docosahexaenoic Acid (DHA)", Pharmacological Research, vol. 40, No. 3, (1999), pp. 211-225.

Stukey, J.E., et al., "The OLE1 Gene of *Saccharomyces cerevisiae* Encodes the Δ 9 Fatty Acid Desaturase and Can Be Functionally Replaced by the Rat Stearoyl-CoA Desaturase Gene", The Journal of Biological Chemistry, vol. 265, No. 33, (1990), pp. 20144-20149.

(Continued)

*Primary Examiner* — Paul Holland
(74) *Attorney, Agent, or Firm* — Drinker Biddle & Reath LLP

(57) ABSTRACT

The present invention relates to polynucleotides from *Ostreococcus lucimarinus* which code for desaturases and elongases and which can be employed for the recombinant production of polyunsaturated fatty acids. The invention furthermore relates to vectors, host cells and transgenic nonhuman organisms which comprise the polynucleotides, and to the polypeptides encoded by the polynucleotides. Finally, the invention also relates to production processes for the polyunsaturated fatty acids and for oil, lipid and fatty acid compositions.

9 Claims, 14 Drawing Sheets

(56) References Cited

OTHER PUBLICATIONS

Wada, H., et al., "Enhancement of Chilling Tolerance of a Cyanobacterium by Genetic Manipulation of Fatty Acid Desaturation", Nature, vol. 347, (1990), pp. 200-203.
Huang, Y.-S., et al., "Cloning of Δ 12- and Δ 6-Desaturases from *Morierella alpine* and Recombinant Production of γ-Linolenic Acid in *Saccharomyces cerevisiae*", Lipids, vol. 34, No. 7, (1999), pp. 649-659.
McKeon, T., et al., "Stearoyl-Acyl Carrier Protein Desaturase from Safflower Seeds", Methods in Enzymology, vol. 71, (1981), pp. 275-281.
Wang, X. M., et al., "Biosynthesis and Regulation of Linolenic Acid in Higher Plants", Plant Physiol. Biochem., vol. 26, No. 6, (1988), pp. 777-792.
Vazhappilly, R., et al., "Heterotrophic Production Potential of Omega-3 Polyunsaturated Fatty Acids by Microalgae and Algae-like Micororganisms", Botanica Marina, vol. 41, (1998), pp. 553-558.
Totani, K., et al., "The Filamentous Fungus *Mortierella alpine*, High in Arachidonic Acid", Lipids, vol. 22, No. 12, (1987), pp. 1060-1062.
Akimoto, M., et al., "Carbon Dioxide Fixation and Polyunsaturated Fatty Acid Production by the Red Alga *Porphyridium Cruentum*", Applied Biochemistry and Biotechnology, vol. 73, (1998), pp. 269-278.
Yu, R., et al., "Production of Eicosapentaenoic Acid by a Recombinant Marine Cyanobacterium, *Synechococcus* sp.", Lipids, vol. 35, No. 10, (2000), pp. 1061-1064.
Takeyama, H., et al., "Expression of the Eicosapentaenoic Acid Synthesis Gene Cluster from *Shewanella* sp. in a Transgenic Marine Cyanobacterium, *Synechococcus* sp.", Micorbiology, vol. 143, (1997), pp. 2725-2731.
Zank, T.K., et al., "Cloning and Functional Characterisation of an Enzyme Involved in the Elongation of Δ 6-Polyunsaturated Fatty Acids from the Moss *Physcomitrella patens*", The Plant Journal, vol. 31, No. 3, (2002), pp. 255-268.
Sakuradani, E., et al., "Δ 6-Fatty Acid Desaturase from an Arachidonic Acid-Producing *Mortierella* Fungus Gene Cloning and its heterologous Expression on a Fungus, *Aspergillus*", Gene, vol. 238, (1999), pp. 445-453.
Sprecher, H., "Metabolism of Highly Unsaturated n-3 and n-6 Fatty Acids", Biochimica et Biophysica Acta, vol. 1486, (2000), pp. 219-231.
Tocher, D.R., et al., "Recent Advances in the Biochemistry and Molecular Biology of Fatty Acyl Desaturases", Prog. Lipid Res., vol. 37, No. 2/3, (1998), pp. 73-117.
Shimokawa, H., "Beneficial Effects of Eicosapentaenoic Acid on Endothelial Vasodilator Functions in Animals and Humans", World Rev. Nutr. Diet, vol. 88, (2001), pp. 100-108.
Calder, P.C., "Dietary Modificationof Inflammation with Lipids", Proceedings of the Nutrition Society, vol. 61, (2002), pp. 345-358.
Cleland and James, "Fish Oil and Rheumatoid Arthritis: Antiinflammatory and Collateral Health Benefits", J. Rheumatol., vol. 27, (2000), pp. 2305-2307.
Millar, A. A., et al., "Very-long-chain Fatty Acid Biosynthesis is Controlled Through the Expression and Specificity of the Condensing Enzyme", The Plant Journal, vol. 12, No. 1, (1997), pp. 121-131.
Millar, A.A., et al., "CUT1, an Arabidopsis Gene Required for Cuticular Wax Biosynthesis and Pollen Fertility, Encodes a Very-Long-Chain Fatty Acid Condensing Enzyme", The Plant Cell, vol. 11, (1999), pp. 825-838.
Tvrdik, P., et al., "Role of a New Mammalian Gene Family in the Biosynthesis of Very Long Chain Fatty Acids and Sphingolipids", The Journal of Cell Biology, vol. 149, No. 3, (2000), pp. 707-717.
Romanos, M.A., et al., "Foreign Gene Expression in Yeast: A Review", Yeast, vol. 8, (1992), pp. 423-488.
Van Den Hondel, C.A.M.J.J., et al., "Heterologous Gene Expression in Filamentous Fungi", in More Gene Manipulations In Fungi, Ed. Bennett and Lasure, Academic Press, Inc. (1991), pp. 396-428.
Van Den Hondel, C.A.M.J.J., et al., "Gene Transfer Systems and Vector Development for Filamentous Fungi", in Applied Molecular Genetics of Fungi, Ed. Peberdy, Caten, Ogden & Bennett, Symposium of the British Mycological Society held at the Univ. of Nottingham, Cambridge University Press, (1990), pp. 1-28.
Falciatore, A., et al., "Transformation of Nonselectable Reporter Genes in Marine Diatoms", Marine Biotechnology, Vo. 1, (1999), pp. 239-251.
Schmidt, R., et al., "High Efficiency *Agrobacterium tumefaciens*-Mediated Transformation of *Arabidopsis thaliana* Leaf and Cotyledon Explants", Plant Cell Reports, vol. 7, (1988), pp. 583-586.
Glick & Thompson (Eds.), "Procedures for Introducing Foregin DNA into Plants" in Methods in Plant Molecular Biology and Biotechnology, CRC Press, vol. 6/7, (1993), pp. 71-119.
White, F.F., et al., "Techniques for Gene Transfer", in Transgenic Plants, Engineering and Utilization, Kung and Wu. (Eds.), Academic Press, (1993), pp. 128-143.
Potrykus, I., "Gene Transfer to Plants: Assessment of Published Approaches and Results", Annu. Rev. Plant Physiol. Plant Molec. Biol, vol. 42, (1991), pp. 205-225.
Mikoklajczak, K.L., et al., "Search for New Industrial Oils v. Oils of Cruciferae", Journal of the American Oil Chemical Society, vol. 38, (1961), pp. 678-681.
Napier, J.A., et al., "Genomic and Functional Characterization of Polyunsaturated Fatty Acid Biosynthesis in *Caenorhabditis elegans*", Lipids, vol. 36, No. 8, (2001), pp. 761-766.
Sayanova, O., et al., "Mutagenesis and Heterologous Expression in Yeast of a Plant Δ6—Fatty Acid Desaturase", Journal of Experimental Botany, vol. 52, No. 360, (2001), pp. 1581-1585.
Sperling, P., et al., "Functional Identification of a Δ8-Sphingolipid Desaturase from *Borago officinalis*", Archives of Biochemistry and Biophysics, vol. 388, No. 2, (2001), pp. 293-298.
Michaelson, L.V., et al., "Functional Identification of a Fatty Acid Δ5 Desaturase Gene from *Caenorhabditis elegans*", FEBS, vol. 439, (1998), pp. 215-218.
Domergue, F., et al., "Cloning and Functional Characterization of *Phaeodactylum tricornutum* Front-End Desaturases Involved in Eicosapentaenoic Acid Biosynthesis", Eur. J. Biochem., vol. 269, (2002), pp. 4105-4113.
"Ostreococcus tauri chromosome 17 contig 1, DNA sequence", Database Accession EMBL No. CR954217, Apr. 30, 2005, Versiond 5 and 10.
Derelle, E., et al., "Genome Analysis of the Smallest Free-Living Eukaryote *Ostreococcus tauri* Unveils Many Unique Features", PNAS, vol. 103, No. 31, (2006), pp. 11647-11652.
Palenik, B., et al., "The Tiny Eukaryote *Ostreococcus* Provides Genomic Insights into the Paradox of Plankton Speciation", PNAS, vol. 104, No. 19, (2007), pp. 7705-7710.
Doerks, et al., "Protein Annotation: Detective Work for Function Prediction", TIG, vol. 14, No. 6, (1998), pp. 248-250.
Brenner, SE, TIG, 15(4), 132-133, (1999).
Bork et al., TIG, vol. 12, No. 10, (1996), pp. 425-427.
Petrie, J. R., et al., "Isolation and Characterisation of a High-Efficiency Desaturase and Elongases from Microalgae for Transgenic LC-PUFA Production", Marine Biotechnology, 2010, vol. 12, pp. 430-438.

* cited by examiner

```
                  *        20         *        40         *        60         *
d4-des-Olu  : ------------------------------------------------------------------MMSLE    :   6
d4-des-Ota  : MYLGRGRLESGTTRGMMRTBARRPSTTSNPCARSRVRKTTERSLAR RRSTSEKG  L LERESER RE GGK  A  :  76
d4-des-Tps  : -------------------------------------------- CNGNLPAS  Q KSTSKPQ QH HRTIS   :  30
                                                          a               e      ar

*        80         *       100         *       120         *       140         *
d4-des-Olu  :                                                                                      :  84
d4-des-Ota  :                                                                                      : 152
d4-des-Tps  : SELAQHNTPKE WCAVHSTPATDP H NNKQHAH VL T  AS HPGG  L L A GK A V  TYH F G F             : 104
              e  Lr    rpdvaApg    dpwndekw k kwtvfrd6ayD6  pFF 4HPGG wL6nLA G4Dc3aL E3YH1RpeVaT

*       160         *       180         *       200         *       220         *
d4-des-Olu  :                                                                 --            --VYA  : 156
d4-des-Ota  :                                                                 --   GDGDDS  RRL LMP-Q Y : 225
d4-des-Tps  : SLIQR  QIGVMSEEAFRDSFYSWT  SDF  TV   RV       RGS   IWIF LFL    WYC  KMYT S           : 179
              arfrmLpkle  fpv av  ksprpnDSplYnn64nRVrReLfpSeGkl    h4 gqdha      gF    ly    t

*       240         *       260         *       280         *       300         *
d4-des-Olu  :   LSGCLLG A----      LT    HBGA     VN    G    DLIY          H                ----   : 224
d4-des-Ota  :   VPFF SPR SR---    RG V RFR     HBGA     VN    G    DLIG          H  HH      ----   : 294
d4-des-Tps  : D DQ GIA AYS GMGTFA   K C  PG HGA FAQNKL    AG  L MIA SAFT LQ  HE EYT VLDG              : 255
              6pg         6          ga 6g    iqHcaNHGAmspspadNg6lGlTnD6lGg6slmWryhHq6sHHibcN

*       320         *       340         *       360         *       380         *
d4-des-Olu  : -------------                   V    D         M          A                           : 265
d4-des-Ota  : -------------                         D         A         AA                          : 335
d4-des-Tps  : VEEERKERGEDVALEEKDQ FE ATEGR YHI  ANVETGSVWH VMR  AMKVIT GY  MGLPIYFR  LRGVGLFV         : 331
                              dnsmDqdVyTampLlrfDArrpk  wyhrfq  SSmflafp6lq6afqvqdi  g6ftrdtega

*       400         *       420         *       440         *
d4-des-Olu  :            T TV  T Y   AA -----      A VA              AV  --P                        : 354
d4-des-Ota  :            T TV  T Y   AA                               AV    A                       : 424
d4-des-Tps  : IG L CGELE TN  FV NH   EH YE TKDLVGGA HVDEKR   KPTTV GDT PA TRSE R KS HNNNKKK GEK      : 407
              klHgAttweLaT6v6gk  VhfG6l  gp     lmsHa  s  v6  givgf6ecqg6Vlactf A6shN   v  eaK  pel

*       460         *       480         *       500         *       520         *
d4-des-Olu  : T  D    TS DH ---    PTGGL  QVEHHLF  IC         TV   A        T PY A             T    : 428
d4-des-Ota  : T  D    TS DH         PTGGL  QVEHHLF  IC         TV   A        T PYA             T    : 498
d4-des-Tps  : SVPSVPFM D AAV CC S MD PGSWPW N FSGGL SHQIEHHALF SICHTN CH QD V EST L FY VPYQSE SN     : 483
              3ggeawerDWqvqQlvTSalWq    gkiqNfF3GGLnlQ6SHHLFPaICfvhYp  Iak6V  eeaAk  g6FY  SyrtL

*       540         *       560         *
d4-des-Olu  :  A     VR HC A       DD L  FA     C AN      : 466
d4-des-Ota  :  A     VR    A       GE     IF        AKA A : 536
d4-des-Tps  : FVA SKMISH KF CK KCE------------------------ : 503
              pgi5v  fw f64d6Gt Aeqi    v  lpk   npql  p
```

PROCESSES FOR PRODUCING POLYUNSATURATED FATTY ACIDS IN TRANSGENIC ORGANISMS

RELATED APPLICATIONS

This application is a divisional of U.S. application Ser. No. 12/444,193, filed Apr. 3, 2009, now U.S. Pat. No. 8,710,299, which is a national stage application (under 35 U.S.C. §371) of PCT/EP2007/060554, filed Oct. 4, 2007, which claims benefit of European application 06121888.9, filed Oct. 6, 2006, the entire contents of each of which are hereby incorporated by reference in this application.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_Listing_17418_00113_US. The size of the text file is 199 KB, and the text file was created on Aug. 22, 2013.

DESCRIPTION

The present invention relates to polynucleotides from *Ostreococcus lucimarinus* which code for desaturases and elongases and which can be employed for the recombinant production of polyunsaturated fatty acids. The invention furthermore relates to vectors, host cells and transgenic nonhuman organisms which comprise the polynucleotides, and to the polypeptides encoded by the polynucleotides. Finally, the invention also relates to production processes for the polyunsaturated fatty acids and for oil, lipid and fatty acid compositions.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter. Polyunsaturated $\omega$3-fatty acids and $\omega$6-fatty acids are therefore an important constituent in animal and human nutrition.

Polyunsaturated long-chain $\omega$3-fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the currently customary composition of human food, an addition of polyunsaturated $\omega$3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (poly unsaturated fatty acids, PUFA, long chain poly unsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta5,8,11,14}$), dihomo-$\gamma$-linolenic acid ($C20:3^{\Delta8,11,14}$) or docosapentaenoic acid (DPA, $C22:5^{\Delta7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated $\omega$3-fatty acids are said to have a positive effect on the cholesterol level in the blood and thus on the possibility of preventing heart disease. The risk of heart disease, stroke or hypertension can be reduced markedly by adding these $\omega$3-fatty acids to the food. Also, $\omega$3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. $\omega$6-Fatty acids such as arachidonic acid tend to have a negative effect on these disorders in connection with these rheumatic diseases on account of our usual dietary intake.

$\omega$3- and $\omega$6-fatty acids are precursors of tissue hormones, known as eicosanoids, such as the prostaglandins, which are derived from dihomo-$\gamma$-linolenic acid, arachidonic acid and eicosapentaenoic acid, and of the thromoxanes and leukotrienes, which are derived from arachidonic acid and eicosapentaenoic acid. Eicosanoids (known as the $PG_2$ series) which are formed from $\omega$6-fatty acids generally promote inflammatory reactions, while eicosanoids (known as the $PG_3$ series) from $\omega$3-fatty acids have little or no proinflammatory effect.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describes a $\Delta$9-desaturase. WO 93/11245 claims a $\Delta$15-desaturase and WO 94/11516 a $\Delta$12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ06-Desaturases are described in WO 93/06712, U.S. Pat. No. 5,614,393, WO 96/21022, WO 00/21557 and WO 99/27111 and the application for the production in transgenic organisms is described in WO 98/46763, WO 98/46764 and WO 98/46765. In this context, the expression of various desaturases and the formation of polyunsaturated fatty acids is also described and claimed in WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum, Porphiridium* species, *Thraustochytrium* species, *Schizochytrium* species or *Crypthecodinium* species, ciliates such as *Stylonychia* or *Colpidium*, fungi such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible.

However, only limited amounts of the desired polyunsaturated fatty acids such as DPA, EPA or ARA can be produced with the aid of the abovementioned microorganisms, and, depending on the microorganism used, these are generally obtained as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the above-described pathway by Δ6-desaturase, Δ6-elongase, Δ5-desaturase, Δ5-elongase and Δ4-desaturase is the Sprecher pathway (Sprecher 2000, Biochim. Biophys. Acta 1486:219-231) in mammals. Instead of the Δ4-desaturation, a further elongation step is effected here to give $C_{24}$, followed by a further Δ6-desaturation and finally β-oxidation to give the $C_{22}$ chain length. Thus what is known as Sprecher pathway is, however, not suitable for the production in plants and microorganisms since the regulatory mechanisms are not known.

Depending on their desaturation pattern, the polyunsaturated fatty acids can be divided into two large classes, viz. ω6- or ω3-fatty acids, which differ with regard to their metabolic and functional activities.

The starting material for the ω6-metabolic pathway is the fatty acid linoleic acid (18:2$^{Δ9,12}$) while the ω3-pathway proceeds via linolenic acid (18:3$^{Δ9,12,15}$) Linolenic acid is formed by the activity of an ω3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω3-desaturase) and must take up these fatty acids (essential fatty acids) via the food. Starting with these precursors, the physiologically important polyunsaturated fatty acids arachidonic acid (=ARA, 20:4$^{Δ5,8,11,14}$), an ω6-fatty acid and the two ω3-fatty acids eicosapentaenoic acid (=EPA, 20:5$^{Δ5,8,11,14,17}$) and docosahexaenoic acid (DHA, 22:6$^{Δ4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

The elongation of fatty acids, by elongases, by 2 or 4 C atoms is of crucial importance for the production of $C_{20}$- and $C_{22}$-PUFAs, respectively. This process proceeds via 4 steps. The first step is the condensation of malonyl-CoA onto the fatty acid-acyl-CoA by ketoacyl-CoA synthase (KCS, hereinbelow referred to as elongase). This is followed by a reduction step (ketoacyl-CoA reductase, KCR), a dehydration step (dehydratase) and a final reduction step (enoyl-CoA reductase). It has been postulated that the elongase activity affects the specificity and rate of the entire process (Millar and Kunst, 1997 Plant Journal 12:121-131).

There have been a large number of attempts in the past to obtain elongase genes. Millar and Kunst, 1997 (Plant Journal 12:121-131) and Millar et al. 1999, (Plant Cell 11:825-838) describe the characterization of plant elongases for the synthesis of monounsaturated long-chain fatty acids (C22:1) and for the synthesis of very long-chain fatty acids for the formation of waxes in plants ($C_{28}$-$C_{32}$). Descriptions regarding the synthesis of arachidonic acid and EPA are found, for example, in WO0159128, WO0012720, WO02077213 and WO0208401. The synthesis of polyunsaturated $C_{24}$-fatty acids is described, for example, in Tvrdik et al. 2000, JCB 149:707-717 or WO0244320.

No specific elongase has been described to date for the production of DHA (C22:6 n-3) in organisms which do not naturally produce this fatty acid. Only elongases which provide $C_{20}$- or $C_{24}$-fatty acids have been described to date. A Δ5-elongase activity has not been described to date.

Higher plants comprise polyunsaturated fatty acids such as linoleic acid (C18:2) and linolenic acid (C18:3). ARA, EPA and DHA are found not at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants, preferably in oil crops such as oilseed rape, linseed, sunflower and soybeans, would be advantageous since large amounts of high-quality LCPUFAs for the food industry, animal nutrition and pharmaceutical purposes might be obtained economically in this way. To this end, it is advantageous to introduce, into oil crops, genes which encode enzymes of the LCPUFA biosynthesis via recombinant methods and to express them therein. These genes encode for example Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*.

The first transgenic plants to comprise and express genes encoding LCPUFA biosynthesis enzymes and which produce LCPUFAs were described for the first time, for example, in DE 102 19 203 (process for the production of polyunsaturated fatty acids in plants). However, these plants produce LCPUFAs in amounts which require further optimization for processing the oils which are present in the plants.

To make possible the fortification of food and of feed with these polyunsaturated fatty acids, there is therefore a great need for means and measures for a simple inexpensive production of these polyunsaturated fatty acids, specifically in eukaryotic systems. The object of the present invention would therefore be the provision of such means and measures. This object is achieved by the use forms which are described in the patent claims and hereinbelow.

The present invention thus relates to a polynucleotide comprising a nucleic acid sequence selected from the group consisting of:
(a) nucleic acid sequence as shown in one of the SEQ ID NO. 1, 3, 5, 7, 9, 11, 13 or 15;
(b) nucleic acid sequence which codes for a polypeptide which features an amino acid sequence as shown in one of SEQ ID NO. 2, 4, 6, 8, 10, 12, 14 or 16;
(c) nucleic acid sequence which codes for a polypeptide with at least 70% identity to a polypeptide which is encoded by the nucleic acid sequence of (a) or (b), where the polypeptide has desaturase or elongase activity; and
(d) nucleic acid sequence for a fragment of a nucleic acid of (a), (b) or (c), where the fragment codes for a polypeptide with a desaturase or elongase activity.

According to the invention, the term "polynucleotide" relates to polynucleotides which comprise nucleic acid sequences which code for polypeptides with desaturase or elongase activity. The desaturase or elongase activities are preferably required for the biosynthesis of lipids or fatty acids. Especially preferably, they take the form of the following desaturase or elongase activities: Δ4-desaturase, Δ5-desaturase, Δ5-elongase, Δ6-desaturase, Δ6-elongase or Δ12-desaturase. The desaturases and/or elongases are preferably involved in the synthesis of polyunsaturated fatty acids (PUFAs) and especially preferably in the synthesis of long-chain PUFAs (LCPUFAs). Suitable detection systems for these desaturase or elongase activities are described in the examples or in WO2005/083053. Especially preferably, the above-mentioned activities are, as regards substrate specificities and conversion rates, those of the respective enzymes from *Ostreococcus lucimarinus*. The specific polynucleotides according to the invention, i.e. the polynucleotides with a nucleic acid sequence as shown in SEQ ID NO: 1, 3, 5, 7, 9, 11, 13 or 15, were obtained from *Ostreococcus lucimarinus*.

Therefore, polynucleotides according to the invention are in particular:

Polynucleotides which code for a polypeptide with Δ12-desaturase activity and which (i) comprise a nucleic acid sequence as shown in SEQ ID NO: 1 or 3, (ii) comprise a nucleic acid sequence which codes for a polypeptide as shown in SEQ ID NO: 2 or 4, (iii) comprise a nucleic acid sequence with at least 83% identity to one of the nucleic acid sequences of (i) or (ii), or (iv) a nucleic acid sequence of a fragments of a nucleic acid from (i), (ii) or (iii).

Polynucleotides which code for a polypeptide with Δ4-desaturase activity and which (i) comprise a nucleic acid sequence as shown in SEQ ID NO: 5, (ii) comprise a nucleic acid sequence which codes for a polypeptide as shown in SEQ ID NO: 6, (iii) comprise a nucleic acid sequence with at least 72% identity to one of the nucleic acid sequences of (i) or (ii), or (iv) a nucleic acid sequence of a fragments of a nucleic acid from (i), (ii) or (iii).

Polynucleotides which code for a polypeptide with Δ5-desaturase activity and which (i) comprise a nucleic acid sequence as shown in SEQ ID NO: 7 or 9, (ii) comprise a nucleic acid sequence which codes for a polypeptide as shown in SEQ ID NO: 8 or 10, (iii) comprise a nucleic acid sequence with at least 72% identity to one of the nucleic acid sequences of (i) or (ii), or (iv) a nucleic acid sequence of a fragment of a nucleic acid from (i), (ii) or (iii).

Polynucleotides which code for a polypeptide with Δ5-elongase activity and which (i) comprise a nucleic acid sequence as shown in SEQ ID NO: 11, (ii) comprise a nucleic acid sequence which codes for a polypeptide as shown in SEQ ID NO: 12, (iii) comprise a nucleic acid sequence with at least 78% identity to one of the nucleic acid sequences of (i) or (ii), or (iv) a nucleic acid sequence of a fragment of a nucleic acid from (i), (ii) or (iii).

Polynucleotides which code for a polypeptide with Δ6-desaturase activity and which (i) comprise a nucleic acid sequence as shown in SEQ ID NO: 13, (ii) comprise a nucleic acid sequence which codes for a polypeptide as shown in SEQ ID NO: 14, (iii) comprise a nucleic acid sequence with at least 72% identity to one of the nucleic acid sequences of (i) or (ii), or (iv) a nucleic acid sequence of a fragment of a nucleic acid from (i), (ii) or (iii).

Polynucleotides which code for a polypeptide with Δ6-elongase activity and which (i) comprise a nucleic acid sequence as shown in SEQ ID NO: 15, (ii) comprise a nucleic acid sequence which codes for a polypeptide as shown in SEQ ID NO: 16, (iii) comprise a nucleic acid sequence with at least 71% identity to one of the nucleic acid sequences of (i) or (ii), or (iv) a nucleic acid sequence of a fragment of a nucleic acid from (i), (ii) or (iii).

Naturally, the abovementioned specific sequences may, taking into consideration the degeneracy of the genetic code, also be modified, where the modified polynucleotides still code for polypeptides with an amino acid sequence as shown in any of SEQ ID NO: 2, 4, 6, 8, 10, 12, 14 or 16 which feature the abovementioned desaturase or elongase activities.

The term "polynucleotide" also comprises variants of the abovementioned specific polynucleotides. These may be homologous, orthologous or paralogous sequences. Such variants comprise nucleic acid sequences which feature at least one base substitution, one base addition or one base deletion, it being intended that the variants still encode a polypeptide with the abovementioned biological activity of the respective starting sequence. Variants comprise polynucleotides which are capable of hybridization, with the abovementioned polynucleotides, preferably under stringent conditions. Especially preferred stringent conditions are known to the skilled worker and can be found in Current Protocols in Molecular Biology, John Wiley & Sons, N.Y. (1989), 6.3.1-6.3.6. A preferred example of stringent hybridization conditions are hybridizations in 6× sodium chloride/sodium citrate (=SSC) at approximately 45° C., followed by one or more wash steps in 0.2×SSC, 0.1% SDS at 50 to 65° C. The skilled worker knows that these hybridization conditions differ regarding temperature and buffer concentration, depending on the type of the nucleic acid and when for example organic solvents are present. The temperature differs for example under "standard hybridization conditions" as a function of the type of the nucleic acid between 42° C. and 58° C. in an aqueous buffer at a concentration of from 0.1 to 5×SSC (pH 7.2). If organic solvent is present in the abovementioned buffer, for example 50% formamide, the temperature under standard conditions is approximately 42° C. Preferably, the hybridization conditions for DNA:DNA hybrids are, for example, 0.1×SSC and 20° C. to 45° C., preferably between 30° C. and 45° C. Preferably, the hybridization conditions for DNA:RNA hybrids are, for example, 0.1×SSC and 30° C. to 55° C., preferably between 45° C. and 55° C. The abovementioned hybridization temperatures are determined for example for a nucleic acid with a length of approximately 100 bp (=base pairs) and a G+C content of 50% in the absence of formamide. The skilled worker knows how the hybridization conditions required can be determined by referring to textbooks such as the abovementioned textbooks, or from the following textbooks: Sambrook et al., "Molecular Cloning", Cold Spring Harbor Laboratory, 1989; Hames and Higgins (Eds.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, it is possible to provide variants of the specific polynucleotides according to the invention by means of processes which are based on the polymerase chain reaction (PCR). To this end, it is first possible to derive primers from conserved sequences (for example sequences which code for functional domains in the polypeptide). Conserved sequences can be determined by sequence alignments with polynucleotides which code for polypeptides with a similar activity. The template used may be DNA or cDNA from bacteria, fungi, plants or animals. DNA fragments which were obtained by PCR can be used for screening suitable genomic libraries or cDNA libraries in order—if required, to isolate, and to determine by sequencing, the complete open reading frame of the polynucleotide. Further variants comprise polynucleotides which comprise a nucleic acid sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity, or with any other percentage identity mentioned herein, with one of the abovementioned specific nucleic acid sequences and which codes for a polypeptide with the respective biological activity. Equally comprised are polynucleotides which comprise nucleic acid sequences which code for a polypeptide with an amino acid sequence which has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity, or with any other percentage identity mentioned herein, with one of the abovementioned specific amino acid sequences and where the polypeptide has the respective biological activity of the starting sequence. The percentage of identical nucleotides or amino acids preferably relates to a sequence segment of at least 50% of the sequences to be compared, and preferably over the entire length of the sequences to be compared. A multiplicity of programs which implement algorithms for such comparisons are described in the prior art and commercially available. In particular, reference may be made to the algorithms of Needleman and Wunsch or Smith and Waterman, which give particularly reliable results. These algorithms can preferably be implemented by the following programs: PileUp (J. Mol. Evolution., 25, 351-360, 1987, Higgins et al., CABIOS, 5 1989: 151-153), Gap and BestFit (Needleman and Wunsch (J. Mol. Biol. 48; 443-453 (1970)) and Smith and Waterman (Adv. Appl. Math. 2; 482-489 (1981))), as part of the GCG software [Genetics Computer Group, 575 Science Drive, Madison, Wis., USA 53711 (1991)]. For the purposes of the present invention, it is especially preferred to determine the percentage (%) of the sequence identity with the GAP program over the entire sequence, with the following set parameters: Gap Weight: 50, Length Weight: 3, Average Match: 10.000 and Average Mismatch: 0.000.

A polynucleotide which only comprises a fragment of the abovementioned nucleic acid sequences is also a polynucleotide according to the invention. Here, it is intended that the fragment codes for a polypeptide which features the biological activity of the starting sequence, or of the polypeptide which the latter codes for. Polypeptides which are encoded by such polynucleotides therefore comprise, or consist of, domains of the abovementioned specific polypeptides (starting polypeptides) which confer the biological activity. A fragment for the purposes of the invention preferably comprises at least 50, at least 100, at least 250 or at least 500 consecutive nucleotides of the abovementioned specific sequences or codes for an amino acid sequence comprising at least 20, at least 30, at least 50, at least 80, at least 100 or at least 150 consecutive amino acids of one of the abovementioned specific amino acid sequences.

The polynucleotide variants according to the invention preferably feature at least 10%, at least 20%, at least 30%, at least 40%, at least 50%, at least 60%, at least 70%, at least 80% or at least 90% of the respective biological activity of the polypeptide which is encoded by the starting sequence. That is to say the polypeptides which are encoded by the polynucleotides according to the invention can participate in the metabolism of compounds required for the synthesis of fatty acids, fatty acid esters such as diacylglycerides and/or triacylglycerides in an organism, preferably in a plant or plant cell, or can participate in the transport of molecules across membranes, which means $C_{18}$-, $C_{20}$- or $C_{22}$-carbon chains in the fatty acid molecule with double bonds at at least two, advantageously three, four, five or six positions.

The polynucleotides according to the invention either comprise the abovementioned specific nucleic acid sequences or consist of them. This is to say that the polynucleotides according to the invention may, in principle, also comprise further nucleotides. These may preferably be 3'- or 5'-untranslated regions of the genomic nucleic acid sequence. They preferably consist of at least 100, 200 or 500 nucleotides at the 5' terminus and of at least 20, 50 or 100 nucleotides at the 3' terminus of the coding region. Further polynucleotides which comprise additional nucleic acid sequences are those which code for fusion proteins. Such fusion proteins can code for further polypeptide or polypeptide portions, in addition to the abovementioned polypeptides. The additional polypeptide or polypeptide portion may take the form of further enzymes of lipid or fatty acid biosynthesis. Others which are feasible are polypeptides which may act as expression markers (green, yellow, red, blue fluorescent proteins, alkaline phosphatase and others) or so-called "tags" as labels or as an aid for purification (for example FLAG tags, 6-histidine tags, MYC tags and others).

Polynucleotide variants can be isolated from different natural or artificial sources. For example, they can be generated artificially by in-vitro or in-vivo mutagenesis. Homologs or orthologs of the specific sequences can be obtained from a wide range of animals, plants or microorganisms. They are preferably obtained from algae. Especially preferred are algae of the family Prasinophyceae such as from the genera *Heteromastix, Mammella, Mantoniella, Micromonas, Neph-* roselmis, Ostreococcus, Prasinocladus, Prasinococcus, Pseudoscourfielda, Pycnococcus, Pyramimonas, Scherffelia or Tetraselmis, such as of the genera and species Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus sp. Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas sp., Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa fo. Rubens or Tetraselmis sp. The polynucleotides are preferably derived from algae of the genera Mantoniella and Ostreococcus. Equally preferred are algae such as Isochrysis or Crypthecodinium, algae/diatoms such as Thalassiosira, Phaeodactylum or Thraustochytrium, mosses such as Physcomitrella or Ceratodon, very especially preferred are the algae of the genera Mantoniella or Ostreococcus or the diatoms of the genera Thalassiosira or Crypthecodinium. The polynucleotides can also be preferably obtained from higher plants such as Primulaceae such as Aleuritia, Calendula stellata, Osteospermum spinescens or Osteospermum hyoseroides, microorganisms such as fungi, such as Aspergillus, Thraustochytrium, Phytophthora, Entomophthora, Mucor or Mortierella, bacteria such as Shewanella, yeasts or animals such as nematodes, for example caenorhabditis, insects or fish. The polynucleotide variants are also preferably derived from an animal from the order vertebrates. Especially preferably, the polynucleotides are derived from the class Vertebrata; Euteleostomi, Actinopterygii; Neopterygii; Teleostei; Euteleostei, Protacanthopterygii, Salmoniformes; Salmonidae or Oncorhynchus and, very especially preferably, from the order Salmoniformes such as the family Salmonidae, such as the genus Salmo, for example from the genera and species Oncorhynchus mykiss, Trutta trutta or Salmo trutta fario. Here, the polynucleotides according to the invention can be isolated by means of standard techniques of molecular biology and of the sequence information provided herein. Also, it is possible, with the aid of comparative algorithms, to identify for example a homologous sequence or homologous, conserved sequence regions at the DNA or amino acid level. These can be employed as hybridization probe and standard hybridization techniques (such as, for example, those described in Sambrook et al., Molecular Cloning: A Laboratory Manual. 2$^{nd}$ Ed., Cold Spring Harbor Laboratory, Cold Spring Harbor Laboratory Press, Cold Spring Harbor, N.Y., 1989) for isolating further nucleic acid sequences which are useful in the process. Moreover, it is possible to isolate polynucleotides or fragments thereof by means of polymerase chain reaction (PCR), where oligonucleotide primers which are based on this sequence or parts thereof are employed (for example, a nucleic acid molecule comprising the complete sequence or part thereof can be isolated by polymerase chain reaction using oligonucleotide primers which have been generated on the basis of the same sequence). For example, it is possible to isolate mRNA from cells (for example by the guanidinium thiocyanate extractive method by Chirgwin et al. (1979) Biochemistry 18:5294-5299) and cDNA can be generated by means of reverse transcriptase (for example Moloney MLV reverse transcriptase, obtainable from Gibco/BRL, Bethesda, Md., or AMV reverse transcriptase, obtainable from Seikagaku America, Inc., St. Petersburg, Fla.). Synthetic oligonucleotide primers for the amplification by means of polymerase chain reaction can be generated on the basis of the amino acid sequences shown in the SEQ ID numbers. A nucleic acid according to the invention can be amplified using cDNA or, alternatively, genomic DNA as the template and suitable oligonucleotide primers, following standard PCR amplification techniques. The nucleic acid amplified thus can be cloned into a suitable vector and characterized by means of DNA sequence analysis. Oligonucleotides which correspond to a desaturase nucleotide sequence can be generated by synthetic standard methods, for example using an automatic DNA synthesizer.

The polynucleotides according to the invention can either be provided in the form of isolated polynucleotides (i.e. isolated from their natural origin, for example the genomic locus) or else in genetically modified form (i.e. the polynucleotides may also be present at their natural genetic locus, but, in such a case, must be genetically modified). An isolated polynucleotide preferably comprises less than 5 kb, 4 kb, 3 kb, 2 kb, 1 kb, 0.5 kb or 0.1 kb of nucleic acid sequence which occurs naturally in its environment. The polynucleotide according to the invention may be present as a single-stranded or double-stranded nucleic acid molecule and may take the form of genomic DNA, cDNA or RNA. The polynucleotides according to the invention comprise all orientations of the sequences shown in the SEQ ID numbers, i.e. also complementary strands and reverse, or reverse-complementary, orientations. The term furthermore also comprises chemically modified nucleic acids, such as the naturally occurring methylated DNA molecules, or artificial nucleic acids, for example biotinylated nucleic acids.

The invention also comprises oligonucleotides of at least 15 bp, preferably at least 20 bp, at least 25 bp, at least 30 bp, at least 35 bp or at least 50 bp, which are capable of specifically hybridizing under stringent conditions with one of the abovementioned polynucleotides. The oligonucleotides may consist of DNA or RNA or both. Such oligonucleotides can be employed as primers for the PCR, as expression-inhibitory antisense oligonucleotides, for RNA interference (RNAi) approaches or for chimeroplastic or genoplastic approaches. RNAi methods are described for example in Fire et al., Nature (1998) 391:806-811; Fire, Trends Genet. 15, 358-363 (1999); Sharp, RNA interference 2001. Genes Dev. 15, 485-490 (2001); Hammond et al. Nature Rev. Genet. 2, 1110-1119 (2001); Tuschl, Chem. Biochem. 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir et al., Genes Dev. 15, 188-200 (2001); WO 01/29058; WO 99/32619; or Elbashir et al., 2001 Nature 411: 494-498 and serve for inhibiting gene expression by degrading the mRNA. Chimeroplastic or genoplastic approaches serve the in-vivo modification (for example the introduction of point mutations) into genes at their endogenous loci. Such methods are disclosed in U.S. Pat. No. 5,565,350, U.S. Pat. No. 5,756,325, U.S. Pat. No. 5,871,984, U.S. Pat. No. 5,731,181, U.S. Pat. No. 5,795,972, U.S. Pat. No. 6,573,046, U.S. Pat. No. 6,211,351, U.S. Pat. No. 6,586,184, U.S. Pat. No. 6,271,360 and U.S. Pat. No. 6,479,292.

Advantageously, it has emerged that the polynucleotides according to the invention can be employed particularly efficiently for the recombinant production of polyunsaturated fatty acids in host cells and transgenic organisms. In particular, the polypeptides encoded by the polynucleotides according to the invention, which have Δ12-desaturase, Δ4-desaturase, Δ5-desaturase, Δ5-elongase, Δ6-desaturase and Δ6-elongase activity, are capable of converting $C_{18}$-, $C_{20}$- and $C_{22}$-fatty acids with one, two, three, four or five double bonds, and preferably polyunsaturated $C_{18}$-fatty acids with one, two or three double bonds such as $C18:1^{\Delta 9}$, $C18:2^{\Delta 9,12}$ or $C18:3^{\Delta 9,12,15}$, polyunsaturated $C_{20}$-fatty acids with three or four double bonds such as $C20:3^{\Delta 8,11,14}$ or $C20:4^{\Delta 8,11,14,17}$ or polyunsaturated $C_{22}$-fatty acids with four or five double bonds such as $C22:4^{\Delta 7,10,13,16}$ or $C22:5^{\Delta 7,10,13,16,19}$. Preferably, it is the fatty acids in phospholipids or CoA fatty acid esters which are desaturated, advantageously in the CoA fatty acid esters. Thus, a simple, inexpensive production of these polyunsaturated fatty acids is possible, specifically in eukaryotic systems. The unsaturated fatty acids produced by means of the polynucleotides according to the invention can then be formulated as oil, lipid and fatty acid compositions and can be employed in a suitable manner.

The present invention furthermore relates to a vector which comprises the polynucleotide according to the invention.

The term "vector" refers to a nucleic acid molecule which is capable of transporting another nucleic acid molecule, such as the polynucleotides according to the invention, to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA, artificial chromosomes. Finally, the term also comprises constructs for the targeted, i.e. homologous, recombination, or the heterologous insertion of polynucleotides.

Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Suitable cloning vectors are generally known to the skilled worker. In particular, they include vectors which can replicate in microbial systems, that is mainly vectors which ensure efficient cloning in yeasts or fungi and which make possible the stable transformation of plants. Those which must be mentioned are in particular various binary and cointegrated vector systems which are suitable for the T-DNA-mediated transformation. Such vector systems are, as a rule, characterized in that they comprise at least the vir genes, which are required for the *agrobacterium*-mediated transformation, and the T-DNA-bordering sequences (T-DNA border). Preferably, these vector systems also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, and the second vector bears T-DNA, but no vir genes. As a result, the last-mentioned vectors are relatively small, easy to manipulate and to replicate both in *E. coli* and in *Agrobacterium*. These binary vectors include vectors from the pBIB-HYG series, the pPZP series, the pBecks series and the pGreen series. Preferably used according to the invention are Bin19, pBI101, pBinAR, pGPTV and pCAMBIA. An overview over binary vectors and their use is found in Hellens et al, Trends in Plant Science (2000) 5, 446-451. The vectors with the inserted polynucleotides according to the invention can be propagated stably under selective conditions in microorganisms, in particular *Escherichia coli* and *Agrobacterium tumefaciens*, and make possible a transfer of heterologous DNA into plants or microorganisms. The polynucleotides according to the invention can be introduced into organisms such as microorganisms or plants by means of the cloning vectors and thus used for transforming plants. Vectors which are suitable for this purpose are published in: Plant Molecular Biology and Biotechnology (CRC Press, Boca Raton, Fla.), chapter 6/7, p. 71-119 (1993); F. F. White, Vectors for Gene Transfer in Higher Plants; in: Transgenic Plants, vol. 1, Engineering and Utilization, eds.: Kung and R. Wu, Academic Press, 1993, 15-38; B. Jenes et al., Techniques for Gene Transfer, in: Transgenic Plants, vol. 1, Engineering and Utilization, eds.: Kung and R. Wu, Academic Press (1993), 128-143; Potrykus, Annu. Rev. Plant Physiol. Plant Molec. Biol. 42 (1991), 205-225)).

The vector is preferably an expression vector. The polynucleotide is present in the expression vector according to the invention in operative (i.e. functional) linkage with an expression control sequence. The expression control sequence together with the polynucleotide and optionally further sequence elements of the vector is also referred to as the expression cassette. The expression control sequence ensures that, after transformation or transfection into a host cell, the polynucleotide can be expressed. The expression control sequence to be used preferably comprises cis-regulatory elements such as promoter and/or enhancer nucleic acid sequences, which are recognized by the transcription machinery of the host cells. The term furthermore comprises other expression control elements, for example polyadenylation signals and RNA-stabilizing sequences. These regulatory sequences are described for example in Goeddel: Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, chapter 7, 89-108, including the literature cited therein. Expression control sequences comprise those which govern the constitutive expression of a nucleotide sequence in many types of host cells, and those which govern the direct expression of the nucleotide sequence only in certain host cells under certain conditions. The skilled worker knows that the design of the expression vector may depend on factors such as the choice of the host cell to be transformed, the extent of the expression of the desired protein and the like. The polynucleotides according to the invention may be present in one or more copies in the expression cassette or in the expression vector according to the invention (for example in the form of several expression cassettes). Here, the regulatory sequences or factors can have a positive effect on, preferably the gene expression of the introduced genes, as described above, and thereby increase it. Thus, it is possible to enhance the regulatory elements advantageously at the transcription level by using strong transcription signals such as promoters and/or "enhancers". Besides, it is also possible to enhance the translation, for example by improving the mRNA stability. Further expression control sequences within the meaning of the present invention are translation terminators at the 3' end of the polynucleotides to be translated. An example of a terminator which can be used here is the OCS1 terminator. As in the case of the promoters, a different terminator sequence should be used for each of the polynucleotides to be expressed.

Preferred expression control sequences or regulatory sequences are present in promoters such as the cos, tac, trp, tet, trp-tet, lpp, lac, lpp-lac, lacIq, T7, T5, T3, gal, trc, ara, SP6, λ-PR or λ-PL promoters and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/355 [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscissic acid-inducible) or WO 93/21334 (ethanol- or cyclohexenol-inducible) promoters. Further suitable plant promoters are the cytosolic FBPase promoter or the ST-LSI promoter of potato (Stockhaus et al., EMBO J. 8, 1989, 2445), the *glycine max* phosphoribosylpyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter as described, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arobidopsis oleosin* promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890. In principle, it is possible to use all natural promoters together with their regulatory sequences, such as those mentioned above, as expression control sequences. It is also possible to use synthetic promoters, either in addition or alone, in particular when they mediate seed-specific expression, such as those described in WO 99/16890.

In order to achieve a particularly high PUFA content, especially in transgenic plants, the polynucleotides of the present invention should preferably be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Bäumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2,2, 1992], Lpt2 and lpt1 (barley) [WO 95/15389 and WO95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure the stable integration of the various biosynthesis genes into the transgenic plant over a plurality of generation, each of the polynucleotides according to the invention should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site, advantageously in a polylinker, for insertion of the nucleic acid to be expressed and, if appropriate, a terminator is then positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338. However, it is also possible to insert a plurality of nucleic acid sequences behind a promoter and, if appropriate, before a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoter, and different terminators can be used in the expression cassette. However, it is also possible to use only one type of promoter in the cassette. This, however, may lead to undesired recombination events.

The recombinant expression vectors used can be designed for the expression in prokaryotic or eukaryotic cells. This is advantageous since intermediate steps of the vector construction are frequently carried out in microorganisms for the sake of simplicity. For example, the Δ12-desaturase, Δ6-desaturase, Δ6-elongase, Δ5-desaturase, Δ5-elongase and/or Δ4-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, is fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the pTrc vector is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophage which harbors a T7 gn1 gene under the transcriptional control of the lacUV 5 promoter.

Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples for vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable yeast vectors are, for example, pAG-1, YEp6, YEp13 or pEMBLYe23.

As an alternative, the polynucleotides according to the invention can also be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

Preferred plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable. Since plant gene expression is very often not limited to the transcriptional level, a plant expression cassette preferably comprises other sequences which are linked operably, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No.

5,352,605 and WO 84/02913), or plant promoters, such as the promoter of the small Rubisco subunit, which is described in U.S. Pat. No. 4,962,028. Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, oil bodies, peroxisomes and other compartments of plant cells.

As described above, plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504, 200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the *sorghum* kasirin gene or the rye secalin gene, which are described in WO 99/16890. Also especially suitable promoters are those which lead to the plastid-specific expression, since plastids are the compartment in which the precursors and some of the end products of lipid biosynthesis are synthesized. Suitable promoters, such as the viral RNA polymerase promoter, are described in WO 95/16783 and WO 97/06250, and the clpP promotor from *Arabidopsis*, described in WO 99/46394.

The abovementioned vectors are only a small overview over possible vectors which are suitable. Further plasmids are known to the skilled worker and are described for example in: Cloning Vectors (eds. Pouwels, P. H., et al., Elsevier, Amsterdam-New York-Oxford, 1985, ISBN 0 444 904018). Further suitable expression systems for prokaryotic and eukaryotic cells, see chapters 16 and 17 of Sambrook, J., Fritsch, E. F., and Maniatis, T., Molecular Cloning: A Laboratory Manual, $2^{nd}$ ed., Cold Spring Harbor Laboratory, Cold Spring Harbor Laboratory Press, Cold Spring Harbor, N.Y., 1989.

As described above, the expression vector can also comprise further genes which are to be introduced into the organisms. It is possible and preferred to introduce into the host organisms, and express in them, regulatory genes, such as genes for inductors, repressors or enzymes which, as a result of their enzymatic activity, engage in the regulation of one or more genes of a biosynthetic pathway. These genes can be of heterologous or homologous origin. Heterologous genes or polynucleotides are derived from a starting organism which differs from the target organism into which the genes or polynucleotides are to be introduced. In the case of homologous genes or polynucleotides, target organism and starting organism are identical. The vector therefore preferably comprises at least one further polynucleotide which codes for a further enzyme which is involved in the biosynthesis of lipids or fatty acids. The enzyme is preferably selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), $\Delta 4$-desaturase(s), $\Delta 5$-desaturase(s), $\Delta 6$-desaturase(s), $\Delta 8$-desaturase(s), $\Delta 9$-desaturase(s), $\Delta 12$-desaturase(s), $\Delta 5$-elongase(s), $\Delta 6$-elongase(s) and $\Delta 9$-elongase(s).

The invention also relates to a host cell which comprises the polynucleotide according to the invention or the vector according to the invention.

In principle, host cells for the purposes of the present invention may be all eukaryotic or prokaryotic cells. They may be primary cells from animals, plants or multi-celled microorganisms, for example from those which are mentioned in another place in the description. The term furthermore also comprises cell lines which can be obtained from these organisms.

However, host cells for the purposes of the invention may also be single-celled microorganisms, for example bacteria or fungi. Especially preferred microorganisms are fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Saccharomycetaceae, Saprolegniaceae, Schizosacharomycetaceae, Sodariaceae or Tuberculariaceae. Further preferred microorganisms are selected from the group: Choanephoraceae, such as the genera *Blakeslea, Choanephora*, for example the genera and species *Blakeslea trispora, Choanephora cucurbitarum, Choanephora infundibulifera* var. *cucurbitarum, Mortierellaceae*, such as the genus *Mortierella*, for example the genera and species *Mortierella isabellina, Mortierella polycephala, Mortierella ramanniana, Mortierella vinacea, Mortierella zonata, Pythiaceae*, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae, Saccharomycetaceae*, such as the genera *Hansenula, Pichia, Saccharomyces, Saccharomycodes, Yarrowia*, for example the genera and species *Hansenula anomala, Hansenula californica, Hansenula canadensis,*

*Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilliermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceta, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces roses, Saccharomyces rouxii, Saccharomyces uvarum, Saccharomycodes ludwigii, Yarrowia lipolytica,* Schizosaccharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe,* Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense.*

Equally preferred as microorganisms are bacteria selected from the group of the families Bacillaceae, Enterobacteriacae or Rhizobiaceae. It is especially preferred to mention the following bacteria selected from the group: Bacillaceae, such as the genus *Bacillus,* for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis;* Enterobacteriacae such as the genera *Citrobacter, Edwardsiella, Enterobacter, Erwinia, Escherichia, Klebsiella, Salmonella* or *Serratia,* for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli-mutabile, Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea;* Rhizobiaceae, such as the genera *Agrobacterium, Carbophilus, Chelatobacter, Ensifer, Rhizobium, Sinorhizobium,* for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium*

*radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense.*

Further utilizable host cells are detailed in: Goeddel, Gene Expression Technology: Methods in Enzymology 185, Academic Press, San Diego, Calif. (1990). Expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Polynucleotides or vectors can be introduced into the host cell as described above by means of transformation or transfection methods which are known in the prior art. Conditions and media for the cultivation of the host cells are also known to the skilled worker.

The host cell according to the invention preferably additionally comprises at least one further enzyme which is involved in the biosynthesis of lipids or fatty acids. Preferred enzymes have already been mentioned in another place in the description. The enzyme can be present in the host cell in endogenous form, i.e. the host cell already naturally expresses a gene which codes for the enzyme in question. Alternatively, it is also possible to introduce, into the host cell, a heterologous polynucleotide which codes for the enzyme. Suitable methods and means for the expression of a heterologous polynucleotide are known in the prior art and are described herein in connection with the polynucleotides, vectors and host cells according to the invention.

The invention also relates to a method of generating a polypeptide with desaturase or elongase activity, comprising the steps:
 (a) expressing a polynucleotide according to the invention in a host cell; and
 (b) obtaining, from the host cell, the polypeptide which is encoded by the polynucleotide.

In this context, the polypeptide can be obtained by all current protein purification methods. The methods comprise, for example, affinity chromatography, molecular sieve chromatography, high-pressure liquid chromatography or else protein precipitation, if appropriate with specific antibodies. Although this is preferred, the process need not necessarily provide a pure polypeptide preparation.

The invention therefore also relates to a polypeptide which is encoded by the polynucleotide according to the invention or which is obtainable by the abovementioned method according to the invention.

The term "polypeptide" refers both to an essentially pure polypeptide, but also to a polypeptide preparation which additionally comprises further components or impurities. The term is also used for fusion proteins or protein aggregates which comprise the polypeptide according to the invention and additionally further components. The term also refers to chemically modified polypeptides. In this context, chemical modifications comprise artificial modifications or naturally occurring modifications, for example posttranslational modifications such as phosphorylation, myristylation, glycosylation and the like. The terms polypeptide, peptide or protein are interchangeable and are used accordingly in the description and in the prior art. The polypeptides according to the invention have the abovementioned biological activities, that is to say desaturase or elongase activities, and can influence the biosynthesis of polyunsaturated fatty acids (PUFAs), preferably the long-chain PUFAs (LCPUFAs), as herein described.

The invention also comprises an antibody which specifically recognizes the polypeptide according to the invention.

Antibodies against the polypeptide according to the invention can be prepared by means of known methods, where purified polypeptide or fragments thereof with suitable epitopes are used as the antigen. Suitable epitopes can be determined by means of known algorithms for the antigenicity determination, based on the amino acid sequences, of the polypeptides according to the invention, provided herein. The relevant polypeptides or fragments can then be synthesized or obtained by recombinant techniques. After animals, preferably mammals, for example hares, rats or mice, have been immunized, the antibodies can then be obtained from the serum, using known methods. Alternatively, monoclonal antibodies or antibody fragments can be provided with the known methods; see, for example, Harlow and Lane "Antibodies, A Laboratory Manual", CSH Press, Cold Spring Harbor, 1988 or Köhler and Milstein, Nature 256 (1975), 495, and Galfré, Meth. Enzymol. 73 (1981), 3.

The antibodies preferably take the form of monoclonal or polyclonal antibodies, single-chain antibodies or chimeric antibodies, and fragments of these such as Fab, Fv or scFv. Further antibodies within the meaning of the invention are bispecific antibodies, synthetic antibodies or their chemically modified derivatives.

It is intended that the antibodies according to the invention specifically recognize the polypeptides according to the invention, that is to say they should not significantly cross-react with other proteins. This can be assayed by means of methods known in the prior art. For example, the antibodies can be employed for the purposes of immunoprecipitation, immunohistochemistry or protein purification (for example affinity chromatography).

The invention furthermore relates to a transgenic, nonhuman organism which comprises the polynucleotide, the vector or the host cell of the present invention. The transgenic, nonhuman organism preferably takes the form of an animal, a plant or a multicellular microorganism.

The term "transgenic" is understood as meaning that a heterologous polynucleotide, that is to say a polynucleotide which does not occur naturally in the respective organism, is introduced in the organism. This can be achieved either by random insertion of the polynucleotide or by homologous recombination. Naturally, it is also possible to introduce the vector according to the invention instead of the polynucleotide. Methods of introducing polynucleotides or vectors for the purposes of random insertion or homologous recombination are known in the prior art and also described in greater detail hereinbelow. Host cells which comprise the polynucleotide or the vector can also be introduced into an organism and thus generate a transgenic organism. In such a case, such an organism takes the form of a chimeric organism, where only those cells which are derived from the introduced cells are transgenic, i.e. comprise the heterologous polynucleotide.

The transgenic nonhuman organisms are preferably oil-producing organisms, which means organisms which are used for the production of oils, like fungi such as *Mortierella* or *Thraustochytrium*, algae such as *Nephroselmis, Pseudo-* scourfielda, Prasinococcus, Scherffelia, Tetraselmis, Mantoniella, Ostreococcus, Crypthecodinium, Phaeodactylum or plants.

Transgenic plants which can be used are, in principle, all plants, that is to say both dicotyledonous and monocotyledonous plants. They preferably take the form of oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, *verbascum*, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, *verbascum*, sesame, cotton, pumpkin/squash, poppy, evening primrose, walnut, linseed, hemp or thistle. Very especially preferred plants are plants such as safflower, sunflower, poppy, evening primrose, walnut, linseed or hemp. In principle, however, all plants which are capable of synthesizing fatty acids are suitable, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*.

Examples which may be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sative* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia* julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa [silk tree], Medicago sativa, Medicago falcata, Medicago varia [alfalfa] Glycine max Dolichos soja, Glycine gracilis, Glycine hispida, Phaseolus max, Soja hispida or Soja max [soybean], Funariaceae, such as the genera Aphanorrhegma, Entosthodon, Funaria, Physcomitrella, Physcomitrium, for example the genera and species Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica var. arctica, Funaria hygrometrica var. calvescens, Funaria hygrometrica var. convoluta, Funaria hygrometrica var. muralis, Funaria hygrometrica var. utahensis, Funaria microstoma, Funaria microstoma var. obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri var. serratum, Physcomitrium immersum, Physcomitrium kellermanii, Physcomitrium megalocarpum, Physcomitrium pyriforme, Physcomitrium pyriforme var. serratum, Physcomitrium rufipes, Physcomitrium sandbergii, Physcomitrium subsphaericum, Physcomitrium washingtoniense, Geraniaceae, such as the genera Pelargonium, Cocos, Oleum, for example the genera and species Cocos nucifera, Pelargonium grossularioides or Oleum cocois [coconut], Gramineae, such as the genus Saccharum, for example the genus and species Saccharum officinarum, Juglandaceae, such as the genera Juglans, Wallia, for example the genera and species Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra or Wallia nigra [walnut], Lauraceae, such as the genera Persea, Laurus, for example the genera and species Laurus nobilis [bay], Persea americana, Persea gratissima or Persea persea [avocado], Leguminosae, such as the genus Arachis, for example the genus and species Arachis hypogaea [peanut], Linaceae, such as the genera Linum, Adenolinum, for example the genera and species Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne var. lewisii, Linum pratense or Linum trigynum [linseed], Lythrarieae, such as the genus Punica, for example the genus and species Punica granatum [pomegranate], Malvaceae, such as the genus Gossypium, for example the genera and species Gossypium hirsutum, Gossypium arboreum, Gossypium barbadense, Gossypium herbaceum or Gossypium thurberi [cotton], Marchantiaceae, such as the genus Marchantia, for example the genera and species Marchantia berteroana, Marchantia foliacea, Marchantia macropora, Musaceae, such as the genus Musa, for example the genera and species Musa nana, Musa acuminate, Musa paradisiaca, Musa spp. [banana], Onagraceae, such as the genera Camissonia, Oenothera, for example the genera and species Oenothera biennis or Camissonia brevipes [evening primrose], Palmae, such as the genus Elacis, for example the genus and species Elaeis guineensis [oil palm], Papaveraceae, such as, for example, the genus Papaver, for example the genera and species Papaver orientale, Papaver rhoeas, Papaver dubium [poppy], Pedaliaceae, such as the genus Sesamum, for example the genus and species Sesamum indicum [sesame], Piperaceae, such as the genera Piper, Artanthe, Peperomia, Steffensia, for example the genera and species Piper aduncum, Piper amalago, Piper angustifolium, Piper auritum, Piper betel, Piper cubeba, Piper longum, Piper nigrum, Piper retrofractum, Artanthe adunca, Artanthe elongate, Peperomia elongate, Piper elongatum, Steffensia elongate [cayenne pepper], Poaceae, such as the genera Hordeum, Secale, Avena, Sorghum, Andropogon, Holcus, Panicum, Oryza, Zea (maize), Triticum, for example the genera and species Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum [barley], Secale cereale [rye], Avena sativa, Avena fatua, Avena byzantina, Avena fatua var. sativa, Avena hybrida [oats], Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cemuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum [millet], Oryza sativa, Oryza latifolia [rice], Zea mays [maize] Triticum aestivum, Triticum durum, Triticum turgidum, Triticum hybemum, Triticum macha, Triticum sativum or Triticum vulgare [wheat], Porphyridiaceae, such as the genera Chroothece, Flintiella, Petrovanella, Porphyridium, Rhodella, Rhodosorus, Vanhoeffenia, for example the genus and species Porphyridium cruentum, Proteaceae, such as the genus Macadamia, for example the genus and species Macadamia intergrifolia [macadamia], Prasinophyceae, such as the genera Nephroselmis, Prasinococcus, Scherffelia, Tetraselmis, Mantoniella, Ostreococcus, for example the genera and species Nephroselmis olivacea, Prasinococcus capsulatus, Scherffelia dubia, Tetraselmis chui, Tetraselmis suecica, Mantoniella squamata, Ostreococcus tauri, Rubiaceae, such as the genus Coffea, for example the genera and species Cofea spp., Coffea arabica, Coffea canephora or Coffea liberica [coffee], Scrophulariaceae, such as the genus Verbascum, for example the genera and species Verbascum blattaria, Verbascum chabdi, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum or Verbascum thapsus [verbascum], Solanaceae, such as the genera Capsicum, Nicotiana, Solanum, Lycopersicon, for example the genera and species Capsicum annuum, Capsicum annuum var. glabriusculum, Capsicum frutescens [pepper], Capsicum annuum [paprika], Nicotiana tabacum, Nicotiana alata, Nicotiana attenuata, Nicotiana glauca, Nicotiana langsdorffii, Nicotiana *obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Multicellular microorganisms which can be employed as transgenic nonhuman organisms are preferably protists or diatoms selected from the group of the families Dinophyceae, Turaniellidae or Oxytrichidae, such as the genera and species: *Crypthecodinium cohnii, Phaeodactylum tricomutum, Stylonychia mytilus, Stylonychia pustulata, Stylonychia putrina, Stylonychia notophora, Stylonychia* sp., *Colpidium campylum* or *Colpidium* sp.

The invention relates to a process for the production of a substance which has the structure shown in the general formula I hereinbelow

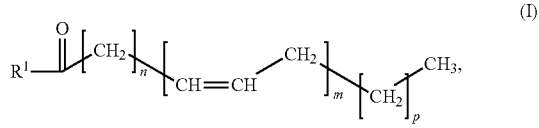

the variables and substituents being the following:
R$^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

R$^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, R$^3$=hydrogen, saturated or unsaturated $C_2$-$C_{24}$-alkylcarbonyl, or R$^2$ and R$^3$ independently of one another are a radical of the formula Ia:

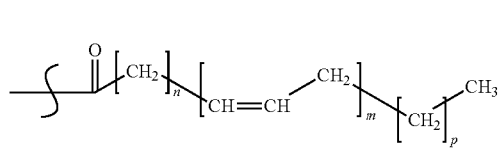

in which
n=2, 3, 4, 5, 6, 7 or 9, m=2, 3, 4, 5 or 6 and p=0 or 3.
and where the process comprises the cultivation of (i) a host cell according to the invention or (ii) a transgenic nonhuman according to the invention under conditions which permit the biosynthesis of the substance. Preferably, the abovementioned substance is provided in an amount of at least 1% by weight based on the total lipid content in the host cell or the transgenic organism.

R$^1$ in the general formula I is hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the general formula II

The abovementioned radicals of R$^1$ are always bonded to the compounds of the general formula I in the form of their thioesters.

R$^2$ in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

R$^3$ in the general formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl-, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the process as a single product or be present in a fatty acid mixture.

Advantageously, the substituents $R^2$ or $R^3$ in the general formulae I and II are, independently of one another, saturated or unsaturated $C_{18}$-$C_{22}$-alkylcarbonyl, especially advantageously, they are, independently of one another, unsaturated $C_{18}$-) $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain polyunsaturated fatty acids with 18, 20 and/or 22 C atoms.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, $C18:2^{\Delta9,12}$), γ-linolenic acid (=GLA, $C18:3^{\Delta6,9,12}$), stearidonic acid (=SDA, $C18:4^{\Delta6,9,12,15}$), dihomo-γ-linolenic acid (=DGLA, $20:3^{\Delta8,11,14}$), ω3-eicosatetraenoic acid (=ETA, $C20:4^{\Delta5,8,11,14}$), arachidonic acid (ARA, $C20:4^{\Delta5,8,11,14}$), eicosapentaenoic acid (EPA, $C20:5^{\Delta5,8,11,14,17}$), ω6-docosapentaenoic acid ($C22:5^{\Delta4,7,10,13,16}$), ω6-docosatetraenoic acid ($C22:4^{\Delta4,7,10,13,16}$), ω3-docosapentaenoic acid (=DPA, $C22:5^{\Delta7,10,13,16,19}$), docosahexaenoic acid (=DHA, $C22:6^{\Delta4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetylcoenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the process according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, $C22:5^{\Delta4,8,12,15,21}$) and no nisinic acid (tetracosahexaenoic acid, $C23:6^{\Delta3,8,12,15,18,21}$). Owing to the nucleic acid sequences of the invention, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *Arabidopsis* or linseed can be obtained when the fatty acids are detected by GC analysis (see examples).

Chemically pure polyunsaturated fatty acids or fatty acid compositions can also be prepared by the processes described above. To this end, the fatty acids or the fatty acid compositions are isolated from the organism, such as the microorganisms or the plants or the culture medium in or on which the organisms have been grown, or from the organism and the culture medium, in the known manner, for example via extraction, distillation, crystallization, chromatography or a combination of these methods. These chemically pure fatty acids or fatty acid compositions are advantageous for applications in the food industry sector, the cosmetic industry sector and especially the pharmacological industry sector.

In principle, all genes of the fatty acid or lipid metabolism can be used in the process for the production of polyunsaturated fatty acids, advantageously in combination with the inventive polynucleotide(s) [for the purposes of the present invention, the plural is understood as encompassing the singular and vice versa]. Genes of the fatty acid or lipid metabolism which are used are advantageously selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Genes selected from the group of the Δ4-desaturases, Δ5-desaturases, Δ6-desaturases, Δ9-desaturases, Δ12-desaturases, Δ6-elongases or Δ5-elongases in combination with the polynucleotides according to the invention are particularly preferably used, it being possible to use individual genes or a plurality of genes in combination.

Advantageously, the desaturases used in the process according to the invention convert their respective substrates in the form of the CoA-fatty acid esters. If preceded by an elongation step, this advantageously results in an increased product yield. The respective desaturation products are thereby synthesized in greater quantities, since the elongation step is usually carried out with the CoA-fatty acid esters, while the desaturation step is predominantly carried out with the phospholipids or the triglycerides. Therefore, a substitution reaction between the CoA-fatty acid esters and the phospholipids or triglycerides, which would require a further, possibly limiting, enzyme reaction, is not necessary.

Owing to the enzymatic activity of the polypeptides used in the process according to the invention, a wide range of polyunsaturated fatty acids can be produced in the process according to the invention. Depending on the choice of the organisms, such as the advantageous plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta9,12}$) is present as unsaturated fatty acid in the plant used for the process, the process can only afford GLA, DGLA and ARA as products, all of which can be present as free fatty acids or in bound form. If only α-linolenic acid (=ALA, C18:3$^{\Delta 9,12,15}$) is present as unsaturated fatty acid in the plant used for the process, as is the case, for example, in linseed, the process can only afford SDA, ETA, EPA and/or DHA as products, all of which can be present as free fatty acids or in bound form, as described above. Owing to the modification of the activity of the enzymes Δ5-desaturase, Δ6-desaturase, Δ4-desaturase, Δ12-desaturase, Δ5-elongase and/or Δ6-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. Advantageously, only ARA, EPA or DHA or mixtures of these are synthesized, depending on the fatty acid present in the organism, or in the plant, which acts as starting substance for the synthesis. Since biosynthetic cascades are involved, the end products in question are not present in pure substances in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA, DHA or their mixtures, advantageously EPA or DHA or their mixtures.

In addition to the production, directly in the organism, of the starting fatty acids for the polypeptides used in the process of the invention, the fatty acids can also be fed externally. The production in the organism is preferred for reasons of economy. Preferred substrates are linoleic acid (C18:2$^{\Delta 9,12}$), γ-linolenic acid (C18:3$^{\Delta 6,9,12}$), eicosadienoic acid (C20:2$^{\Delta 11,14}$), dihomo-γ-linolenic acid (C20:3$^{\Delta 8,11,14}$), arachidonic acid (C20:4$^{\Delta 5,8,11,14}$), docosatetraenoic acid (C22:4$^{\Delta 7,10,13,16}$) and docosapentaenoic acid (C22:5$^{\Delta 4,7,10,13,15}$).

To increase the yield in the above-described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which encodes a polypeptide with Δ12-desaturase. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases for producing the starting product linoleic acid is advantageous.

The process according to the invention advantageously employs the abovementioned nucleic acid sequences or their derivatives or homologues which code for polypeptides which retain the enzymatic activity of the proteins encoded by nucleic acid sequences. These sequences, individually or in combination with the polynucleotides according to the invention, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a polynucleotide according to the invention, a gene construct or a vector as described below, alone or in combination with further nucleic acid sequences which code for proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella*, *Thalassiosira*, *Mantoniella*, *Ostreococcus*, *Saccharomyces* or *Thraustochytrium*, or a greenhouse- or field-grown culture of a plant. The cell or the organism thus produced is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Suitable organisms or host cells for the process according to the invention are those which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella*, *Thraustochytrium*, *Saprolegnia*, *Phytophthora* or *Pythium*, bacteria, such as the genus *Escherichia* or *Shewanella*, yeasts, such as the genus *Saccharomyces*, cyanobacteria, ciliates, algae such as *Mantoniella* or *Ostreococcus*, or protozoans such as dinoflagellates, such as *Thalassiosira* or *Crypthecodinium*. Preferred organisms are those which are naturally capable of synthesizing substantial amounts of oil, such as fungi, such as *Mortierella alpina*, *Pythium insidiosum*, *Phytophthora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula*, *Mortierella* or *Saccharomyces cerevisiae* being especially preferred. In principle, host organisms are, in addition to the abovementioned transgenic organisms, also transgenic animals, advantageously nonhuman animals, for example *C. elegans*. Further suitable host cells and organisms have already been described extensively above.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, for example the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$ or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the above-described process, especially preferably oil, lipid or a fatty acid composition comprising PUFAs and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tariric acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, C22: $5^{\Delta 4,8,12,15,21}$) and no nisinic acid (tetracosahexaenoic acid, C23:$6^{\Delta 3,8,12,15,18,21}$).

The oils, lipids or fatty acids according to the invention preferably comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or DHA, based on the total fatty acid content of the production organism, advantageously of a plant, especially advantageously of an oil crop plant such as soybean, oilseed rape, coconut, oil palm, safflower, flax, hemp, castor-oil plant, *Calendula*, peanut, cacao bean, sunflower, or the abovementioned further mono- or dicotyledonous oil crop plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in "trans", so that the gene is operably linked with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are suitable for the polypeptides according to the invention or of the polypeptide of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are advantageously $C_{16}$-, $C_{18}$- or $C_{20}$-fatty acids. The fatty acids converted as substrates in the process are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles $C_{22}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to give $C_{20}$- and/or $C_{22}$-fatty acids with at least two double bonds in the fatty acid molecule, preferably with three, four, five or six double bonds, very especially preferably with five or six double bonds in the molecule. After a first desaturation and the elongation have taken place, further desaturation and elongation steps such as, for example, such a desaturation in the Δ5 and Δ4 position may take place. Products of the process according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of the fatty acids, oils, lipids or fats in the plants which are advantageously used is, for example, in general the seed or cell strata of the seed, so that seed-specific expression of the nucleic acids used in the process is sensible. However, it is obvious that the biosynthesis of fatty acids, oils or lipids need not be limited to the seed tissue, but can also take place in a tissue-specific manner in all the other parts of the plant, for example in epidermal cells or in the tubers.

If microorganism such as yeasts, such as *Saccharomyces* or *Schizosaccharomyces*, fungi such as *Mortierella, Aspergillus, Phytophthora, Entomophthora, Mucor* or *Thraustochytrium*, algae such as *Isochrysis, Mantoniella, Ostreococcus, Phaeodactylum* or *Cryptecodinium* are used as organisms in the process according to the invention, these organisms are advantageously grown in fermentation cultures.

Owing to the use of the nucleic acids according to the invention which code for a Δ5-elongase, the polyunsaturated fatty acids produced in the process can be increased by at least 5%, preferably by at least 10%, especially preferably by at least 20%, very especially preferably by at least 50% in comparison with the wild types of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while introducing oxygen gas. The pH of the nutrient liquid can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einfuhrüng in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air, into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The polynucleotides or polypeptides of the present invention which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes lead to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, New York, and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool from the phospholipids. This is made possible by acyl-CoA:lysophospholipid acyltransferases. Moreover, these enzymes are capable of transferring the elongated fatty acids from the CoA esters back to the phospholipids. If appropriate, this reaction sequence can be followed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the desaturases used in the process, such as the Δ12-, Δ4-, Δ5- and Δ6-desaturases and/or Δ5-, Δ6-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The synthesized $C_{20}$- or $C_{22}$-fatty acids with at least two, three, four, five or six double bonds in the fatty acid are obtained in the process according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the invention, a "glyceride" is furthermore understood as meaning glycerol derivatives. In addition to the above-described fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: JK Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantity and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms production or productivity are known in the art and encompass the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term production efficiency comprises the time required for obtaining a specific production quantity (for example the time required by the cell to establish a certain throughput rate of a fine chemical). The term yield or product/carbon yield is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained, in a specific culture quantity over a specified period of time is increased. The terms biosynthesis or biosynthetic pathway are known in the art and comprise the synthesis of a compound, preferably an organic compound, by a cell from intermediates, for example in a multi-step and strongly regulated process. The terms catabolism or catabolic pathway are known in the art and comprise the cleavage of a compound, preferably of an organic compound, by a cell to give catabolites (in more general terms, smaller or less complex molecules), for example in a multi-step and strongly regulated process. The term metabolism is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

By employing, in the process according to the invention, the polynucleotides according to the invention and optionally further polynucleotides which code for enzymes of the lipid or fatty acid metabolism it is possible to achieve various advantageous effects. Thus, it is possible to influence the yield, production and/or production efficiency of the polyunsaturated fatty acids in a plant, preferably in an oil crop plant, or in a microorganism. The number or activity of the polypeptides or polynucleotides according to the invention can be increased, so that larger amounts of the gene products and, ultimately, larger amounts of the compounds of the general formula I are produced. A de novo synthesis in an organism, which, before the gene(s) in question has/have been introduced, had been lacking the activity and capability of biosynthesizing the compounds, is also possible. The same applies analogously to the combination with further desaturases or elongases or further enzymes of the fatty acid and lipid metabolism. The use of a variety of divergent sequences, i.e. sequences which differ at the DNA sequence level, may be advantageous in this context, or else the use of gene expression promoters which makes possible a different gene expression as far as timing is concerned, for example as a function of the degree of maturity of a seed or oil-storing tissue.

By introducing, into an organism, a polynucleotide according to the invention alone or in combination with other genes into a cell it is possible not only to increase the biosynthetic flow towards the end product, but also to increase, or to create de novo, the corresponding triacylglycerol composition. Equally, the number or activity of other genes which are required for the import of nutrients for the biosynthesis of one or more fatty acids, oils, polar and/or neutral lipids, so that the concentration of these precursors, cofactors or intermediates within the cells or within the storage compartment is increased, whereby the ability of the cells to produce PUFAs is further enhanced. By optimizing the activity, or increasing the number, of one or more polynucleotides or polypeptides according to the invention which are involved in the biosynthesis of these compounds, or by destroying the activity of one or more genes which are involved in the degradation of these compounds, it may be possible to increase the yield, production and/or production efficiency of fatty acid and lipid molecules from organisms, in particular from plants. The fatty acids obtained in the process are suitable as starting materials for the chemical synthesis of further products of interest. For example, they can be used for the preparation of pharmaceuticals, foodstuffs, animal feeds or cosmetics, either alone or in combination with one another.

It can be seen from what has been said above that the invention also relates to a process for the preparation of an oil, lipid or fatty acid composition, comprising the steps of the process according to the invention and the further step of formulating the substance as an oil, lipid or fatty acid composition.

In a preferred embodiment of this process, the oil, lipid or fatty acid composition is formulated further to give a pharmaceutical, a cosmetic product, a foodstuff, a feeding stuff, preferably fish food, or a food supplement.

Finally, the invention relates to the principle of using the polynucleotide, the vector, the host cell, the polypeptide or the transgenic, nonhuman organism of the present invention for the production of an oil, lipid or fatty acid composition. The latter is then preferably to be employed as pharmaceutical, cosmetic product, foodstuff, feeding stuff, preferably fish food, or food supplement.

The content of all the references, patent applications, patents and published patent applications cited in the present patent application is herewith incorporated by reference to the respective specific disclosure.

FIGURES

Figure 1:
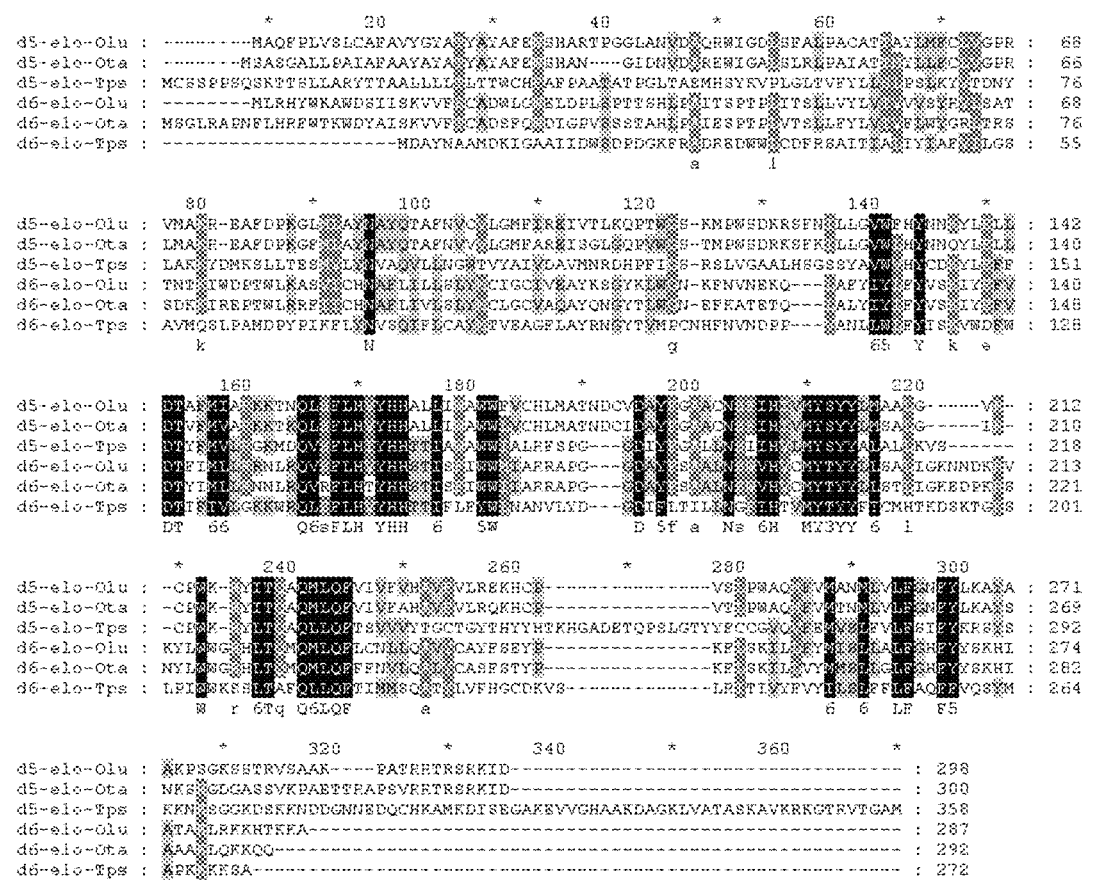

FIG. 1 shows a sequence alignment of the Δ5- and Δ6-elongase amino acid sequences from *O. lucimarinus* (d5-elo-Olu (SEQ ID NO: 12); d6-elo-Olu (SEQ ID NO: 16)), *O. tauri* (d5-elo-Ota (SEQ ID NO: 18); d6-elo-Ota (SEQ ID NO: 20)), and *T. pseudonana* (d5-elo-Tps (SEQ ID NO: 34); d6-elo-Tps (SEQ ID NO: 36)) in the ClustalW comparison.

FIG. 2 shows a sequence alignment of the Δ4-desaturase amino acid sequences from *O. lucimarinus* (d4-des-Olu (SEQ ID NO: 6)), *O. tauri* (d4-des-Ota (SEQ ID NO: 24)), and *T. pseudonana* (d4-des-Tps (SEQ ID NO: 42)) in the ClustalW comparison.

Figure 3:
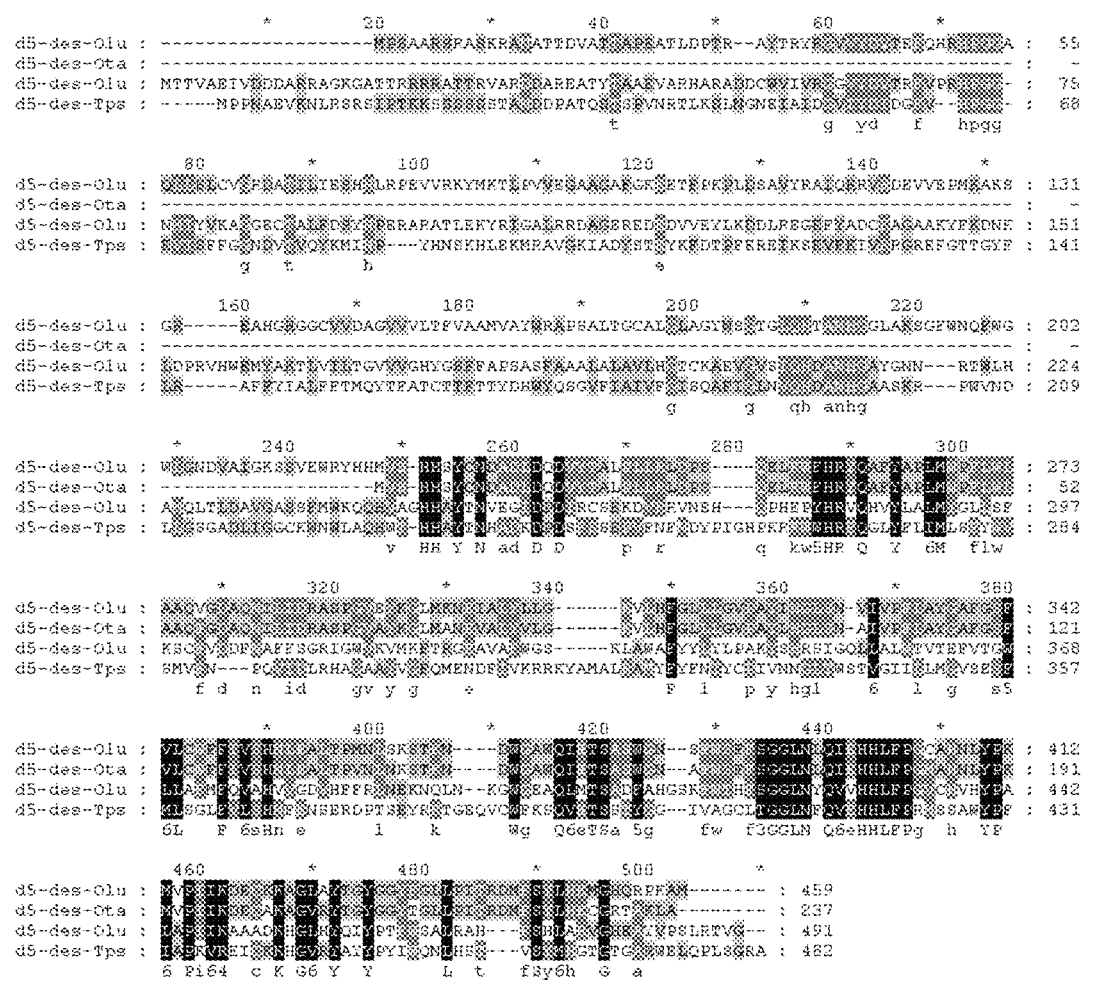

FIG. 3 shows a sequence alignment of the Δ5-desaturase amino acid sequences from *O. lucimarinus* (first d5-des-Olu (SEQ ID NO: 8); second d5-des-Olu (SEQ ID NO: 10)), *O. tauri* (d5-des-Ota (SEQ ID NO: 28)), and *T. pseudonana* (d5-des-Tps (SEQ ID NO: 40)) in the ClustalW comparison.

Figure 4:
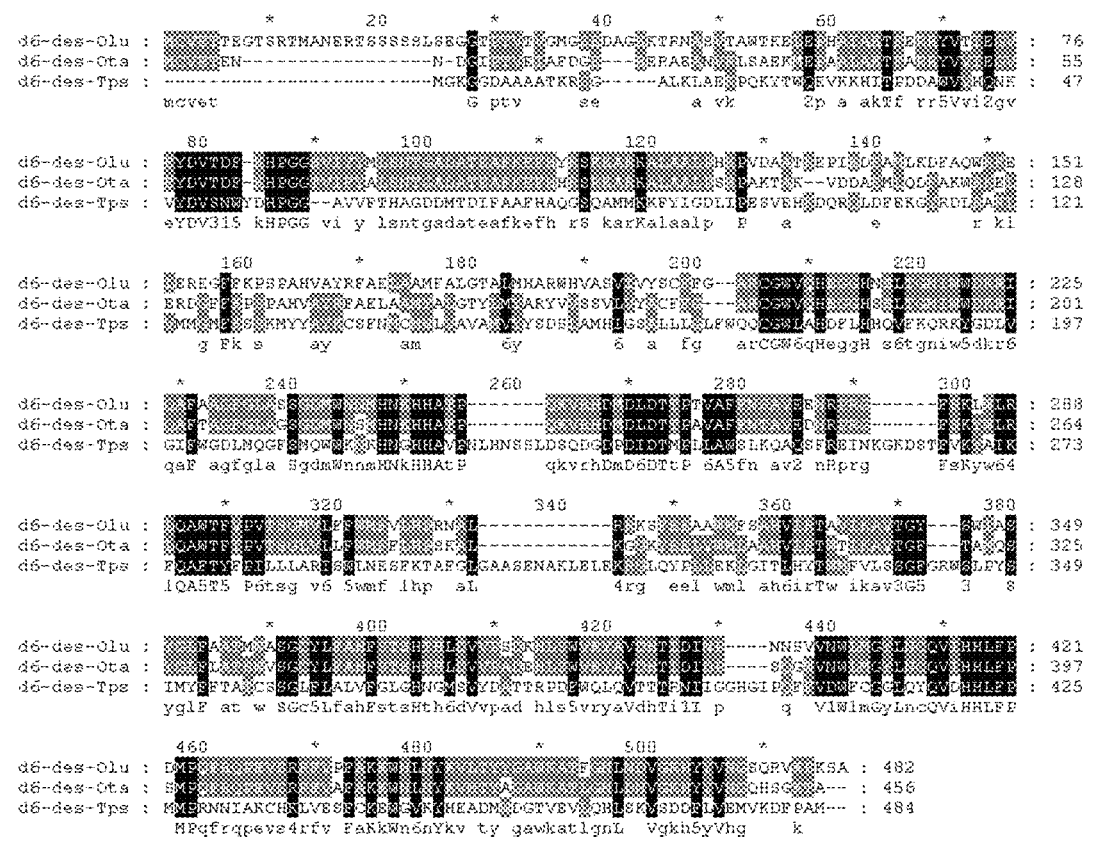

FIG. 4 shows a sequence alignment of the Δ6-desaturase amino acid sequences from *O. lucimarinus* (d6-des-Olu (SEQ ID NO: 14)), *O. tauri* (d6-des-Ota (SEQ ID NO: 30)), and *T. pseudonana* (d6-des-Tps (SEQ ID NO: 38)) in the ClustalW comparison.

Figure 5:
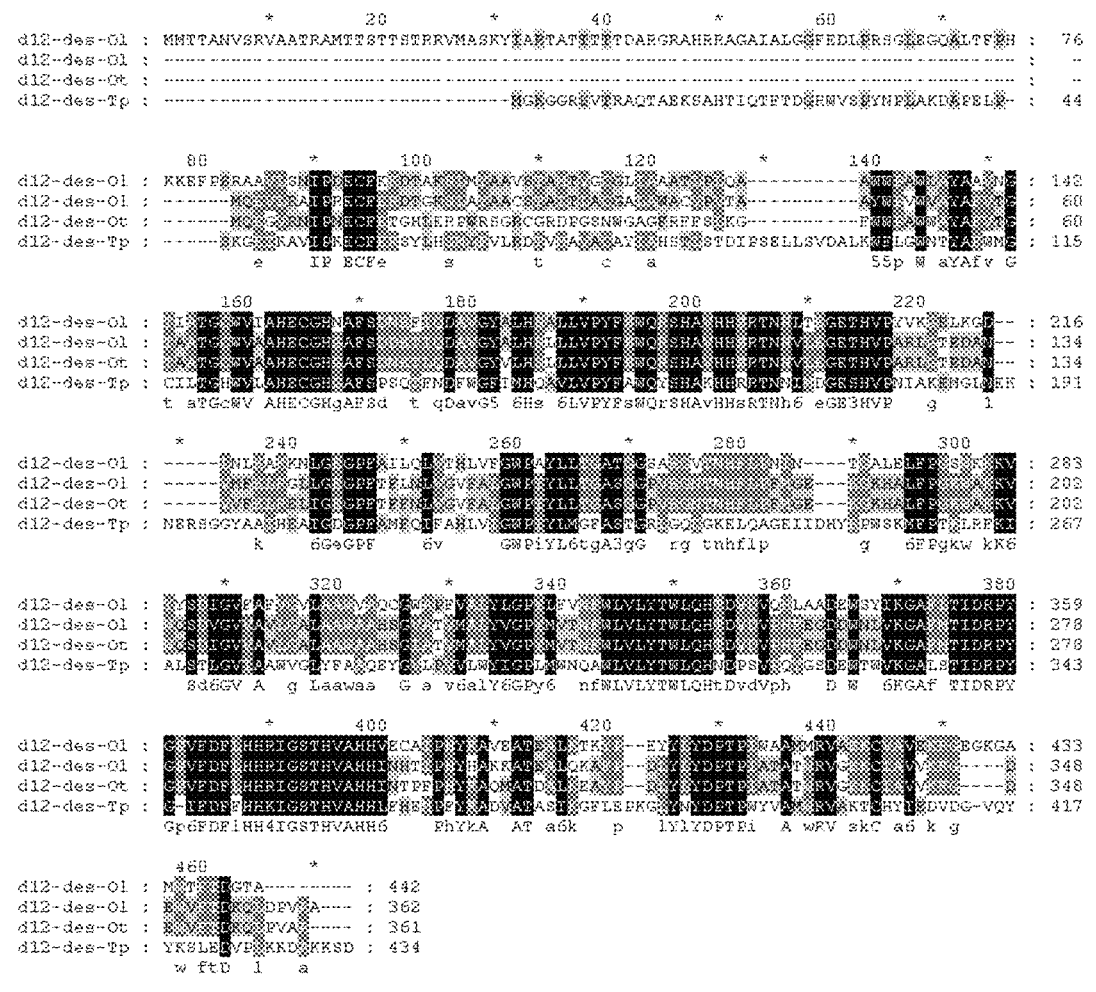

FIG. 5 shows a sequence alignment of the Δ12-desaturase amino acid sequences from *O. lucimarinus* (first d12-des-OI (SEQ ID NO: 4); second d12-des-OI (SEQ ID NO: 2)), *O. tauri* (d12-des-Ot (SEQ ID NO: 32)), and *T. pseudonana* (d12-des-Tp (SEQ ID NO: 44)) in the ClustalW comparison.

Figure 6:
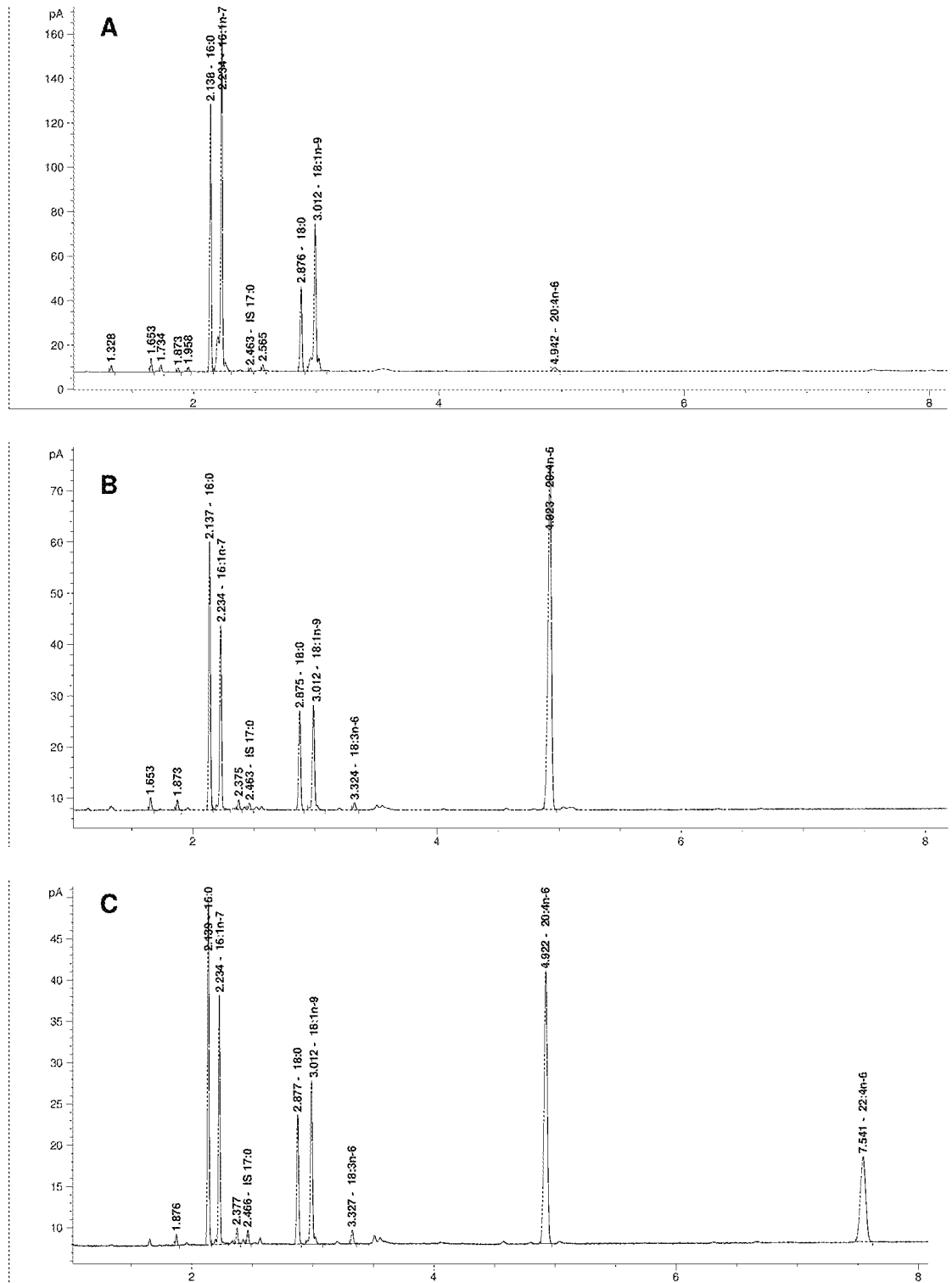
FIG. 6 shows the gas-chromatographic determination of the fatty acids from yeasts which have been transformed with the plasmid pYES (A, B) or pYES-D5Elo(OI) (C). The fatty acid 20:4Δ5,8,11,14 was fed (B, C).

The present invention is illustrated in greater detail by the examples which follow, which are not to be construed as limiting.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA74, 5463-5467). Fragments obtained by polymerase chain reaction were sequenced and verified to avoid polymerase errors in constructs to be expressed.

Example 3

Lipid Extraction from Yeasts

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of the lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Better, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

The unambiguous proof for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 µm, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Example 4

Cloning and Characterization of Elongase Genes from *Ostreococcus lucimarinus*

By searching for conserved regions in the protein sequences in elongase genes, it was possible to identify two sequences with corresponding motifs in an *Ostreococcus lucimarinus* sequence database. In a further step, the genes were characterized by means of sequence alignment, gene prediction and the search for coding regions. The following coding regions were found:

TABLE 1

| Coding regions | | |
|---|---|---|
| Name of gene | SEQ ID | Amino acids |
| D5Elo(Ol) | 12 | 298 |
| D6Elo(Ol) | 16 | 287 |

FIG. 1 shows the sequence similarities with other algae (*Ostreococcus tauri, Thalassiosira pseudonana*) for the various elongase amino acid sequences in the ClustalW sequence alignment. Surprisingly, the *O. lucimarinus* sequences differ markedly from the other algae in their amino acid sequence.

TABLE 2

| Sequence identities of individual elongases | | | |
|---|---|---|---|
| Name of gene | SEQ ID | Organism | Identity in % |
| D5Elo(Ol) | 28 | *O. lucimarinus* | 100 |
| | | *O. tauri* | 77 |
| | | *T. pseudonana* | 21 |
| D6Elo(Ol) | 32 | *O. lucimarinus* | 100 |
| | | *O. tauri* | 71 |
| | | *T. pseudonana* | 25 |

The cloning procedure was carried out as follows:

40 ml of an *Ostreococcus lucimarinus* culture in the stationary phase were spun down and resuspended in 100 µl of double-distilled water and stored at −20° C. The relevant genomic DNAs were amplified based on the PCR method. The corresponding primer pairs were selected in such a way that they contained the yeast consensus sequence for highly efficient translation (Kozak, Cell 1986, 44:283-292) next to the start codon. The amplification of the DNAs was carried out using in each case 1 µl of defrosted cells, 200 µM dNTPs, 2.5 U Taq polymerase and 100 pmol of each primer in a total volume of 50 µl. The conditions for the PCR were as follows: first denaturation at 95° C. for 5 minutes, followed by 30 cycles at 94° C. for 30 seconds, 55° C. for 1 minute and 72° C. for 2 minutes, and a final elongation step at 72° C. for 10 minutes.

To characterize the function of the *Ostreococcus lucimarinus* elongases, the open reading frames of the DNAs in question are cloned downstream of the galactose-inducible GAL1 promoter of pYES2.1/V5-His-TOPO (Invitrogen), giving rise to pOLE1 and pOLE2.

The *Saccharomyces cerevisiae* strain 334 is transformed with the vector pOLE1 or pOLE2, respectively, by electroporation (1500V). A yeast which is transformed with the blank vector pYES2 is used as control. The transformed yeasts are selected on complete minimal dropout uracil medium (CM-dum) agar plates supplemented with 2% glucose. After the selection, in each case three transformants are selected for the further functional expression.

To express the Ol elongases, precultures consisting of in each case 5 ml of CMdum dropout uracil liquid medium supplemented with 2% (w/v) raffinose are initially inoculated with the selected transformants and incubated for 2 days at 30° C. and 200 rpm. Then, 5 ml of CMdum (dropout uracil) liquid medium supplemented with 2% raffinose and 300 µM various fatty acids are inoculated with the precultures to an $OD_{600}$ of 0.05. Expression is induced by the addition of 2% (w/v) galactose. The cultures were incubated for a further 96 hours at 20° C.

Yeasts which have been transformed with the plasmids pYES2, pOLE1 and pOLE2 are analyzed as follows:

The yeast cells from the main cultures are harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) are prepared by acid methanolysis. To this end, the cell sediments are incubated for one hour at 80° C. together with 2 ml of 1 N methanolic sulfuric acid and 2% (v/v) of dimethoxypropane. The FAMEs are extracted twice with petroleum ether (PE). To remove nonderivatized fatty acids, the organic phases are washed in each case once with 2 ml of 100 mM $NaHCO_3$, pH 8.0 and 2 ml of distilled water. Thereafter, the PE phases are dried with $Na_2SO_4$, evaporated under argon and taken up in 100 µl of PE. The samples are separated on a DB-23 capillary column (30 m, 0.25 mm, 0.25

μm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of D5Elo(OI):

To determine the activity and substrate specificity of d5Elo (OI), various fatty acids were fed (table 3). The substrates fed can be detected in large amounts in all of the transgenic yeasts. The transgenic yeasts reveal the synthesis of novel fatty acids, the products of the d5Elo(OI) reaction. This means that the gene d5Elo(OI) was expressed functionally.

TABLE 3

Feeding of yeasts with the plasmids pYES and pYES-D5Elo(Ol)

| Sample name/fatty acid fed | Expected conversion | Substrate | Product |
|---|---|---|---|
| pYES | Control | — | — |
| pYES-D5Elo(Ol_GA) 20:4 | 20:4 –> 22:4 | 98.0 | 48.5 |
| pYES-D5Elo(Ol_GA) 20:4 | 20:4 –> 22:4 | 62.6 | 32.2 |

FIG. 6 shows the chromatograms of the individual experiments. In FIG. 6a, yeasts transformed with pYES were analyzed without the addition of fatty acids by way of control. In FIG. 1b, the pYES-transformed yeasts were fed the fatty acid 20:4Δ5,8,11,14. Here, the fed fatty acid can be detected in large amounts. The same experiment is carried out in FIG. 6C for yeasts transformed with the plasmid pYES-D5Elo(OI). As opposed to FIG. 6B, it is possible to detect, in the yeasts with pYES-D5Elo(OI), an additional fatty acid, which must be attributed to the D5Elo(OI) activity. With reference to the activity, it is possible to characterize D5Elo(OI) as a Δ5-elongase.

Summary of the D5Elo(OI) Results:

It was possible to demonstrate in the yeast feeding experiments that the cloned gene D5Elo(OI) SEQ ID12 was expressed functionally and that it has elongase activity. By reference of the fed fatty acid, it is possible to characterize D5Elo(OI) as a Δ5-elongase, i.e. C20-fatty acids with a Δ5-double bond are elongated specifically.

Activity and Substrate Determination of D6Elo(OI):

To determine the activity and substrate specificity of D6Elo (OI), various fatty acids were fed (table 4). The substrates fed can be detected in large amounts in all of the transgenic yeasts. The transgenic yeasts reveal the synthesis of novel fatty acids, the products of the D6Elo(OI) reaction. This means that the gene D6Elo(OI) was expressed functionally.

TABLE 4

Feeding/conversion of various fatty acids with D6Elo(Ol)

| Sample name/fatty acid fed | Expected conversion | Substrate | Product |
|---|---|---|---|
| pYES | Control | — | — |
| pYES-D6Elo(Ol_GA) γ18:3 | γ18:3 –> 20:3 | 236.5 | 232.1 |
| pYES-D6Elo(Ol_GA) γ18:3 | γ18:3 –> 20:3 | 111.2 | 126.5 |

TABLE 4-continued

Feeding/conversion of various fatty acids with D6Elo(Ol)

| Sample name/fatty acid fed | Expected conversion | Substrate | Product |
|---|---|---|---|
| pYES-D6Elo(Ol_GA) 18:4 | 18:4 –> 20:4 | 94.3 | 82.9 |
| pYES-D6Elo(Ol_GA) 18:4 | 18:4 –> 20:4 | 73.2 | 68.3 |

Figure 7:
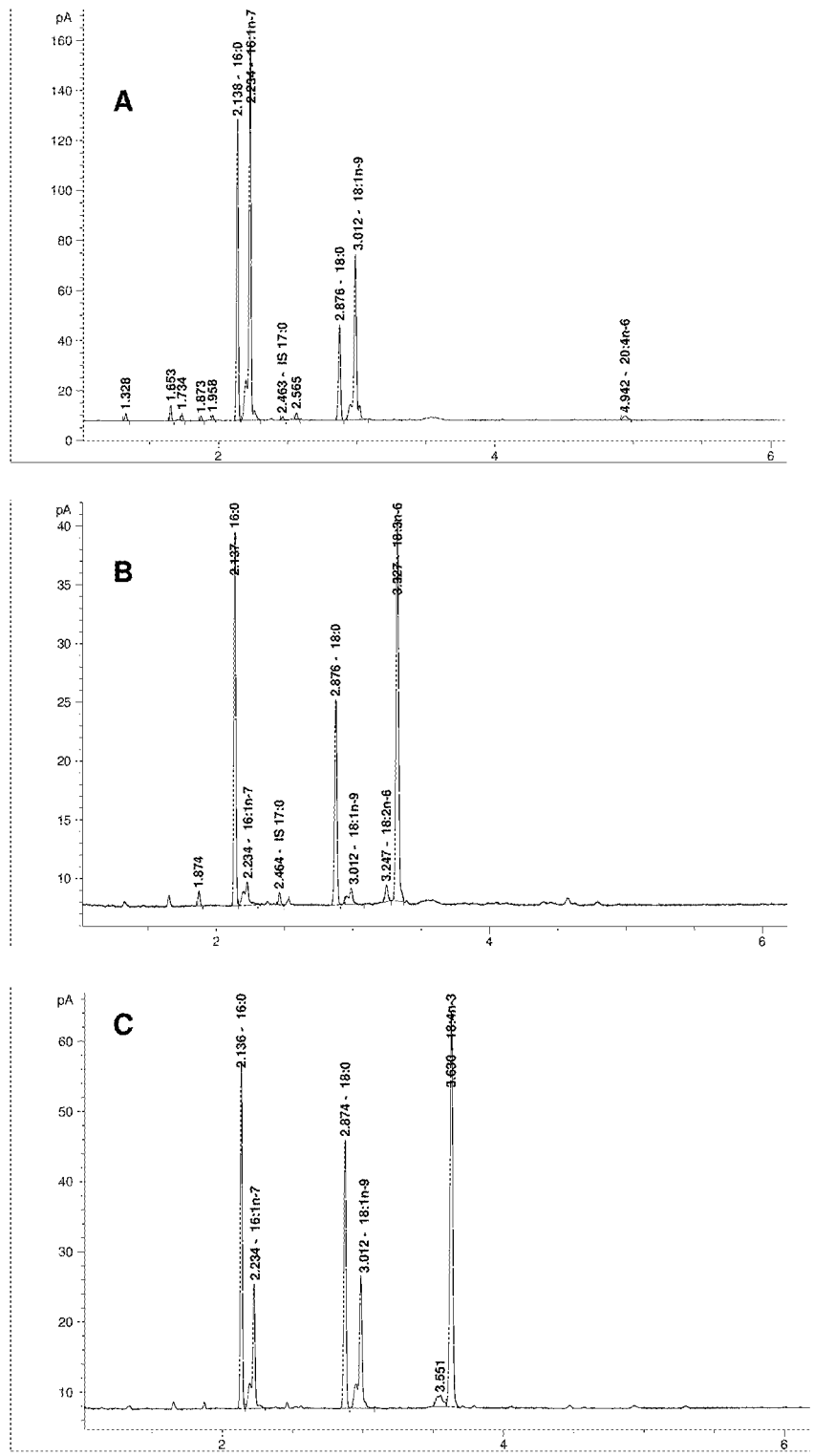
FIG. 7 shows the gas-chromatographic determination of the fatty acids from yeasts which have been transformed with the plasmid pYES (A, B, C) or pYES-D6Elo(OI) (D,E). The fatty acids 18:3Δ6,9,12 or 18:4Δ6,9,12,15 were fed (B, D) and (C, E), respectively.
Figure 7:
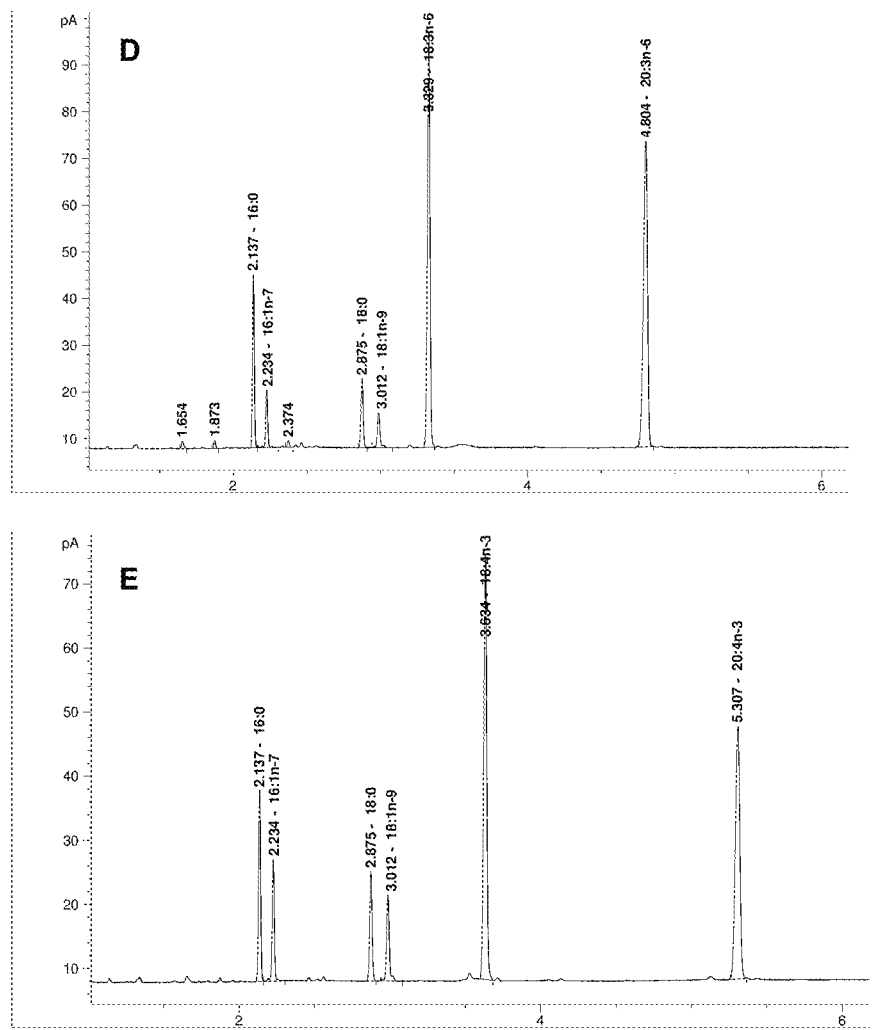

FIG. 7 shows the chromatograms of the individual experiments. In FIG. 7a, yeasts transformed with pYES were analyzed without the addition of fatty acids by way of control. In FIGS. 7b and 7c, the pYES-transformed yeasts were fed the fatty acid 18:3Δ6,9,12(b) and 18:4Δ6,9,12,15(c), respectively. Here, the fed fatty acids can be detected in large amounts. The same experiment is carried out in FIGS. 7C and 7D for yeasts transformed with the plasmid pYES-D6Elo (OI). As opposed to FIGS. 7B and 7C, it is possible to detect, in the yeasts with pYES-D6Elo(OI), an additional fatty acid, which must be attributed to the D6Elo(OI) activity. With reference to the activity, it is possible to characterize D6Elo (OI) as a Δ6-elongase.

Summary of the D6Elo(OI) Results:

It was possible to demonstrate in the yeast feeding experiments that the cloned gene D6Elo(OI) SEQ ID NO: 16 was expressed functionally and that it has elongase activity. By reference to the fed fatty acid, it is possible to characterize D6Elo(OI) as a Δ6-elongase, i.e. C18-fatty acids with a Δ6-double bond are elongated specifically.

Example 5

Cloning and Characterization of *Ostreococcus lucimarinus* Desaturase Genes

By searching for conserved regions in the protein sequences with the aid of conserved motifs (H is boxes, Domergue et al. 2002, Eur. J. Biochem. 269, 4105-4113), it was possible to identify five sequences with corresponding motifs in an *Ostreococcus lucimarinus* sequence database (genomic sequences). In a further step, the genes were characterized by means of sequence alignment, gene prediction and the search for coding regions. The following coding regions were found:

TABLE 5

Coding regions

| Name of gene | SEQ ID | Amino acids |
|---|---|---|
| D4Des(Ol) | 6 | 466 |
| D5Des(Ol) | 8 | 459 |
| D5Des_2(Ol) | 10 | 491 |
| D6Des(Ol) | 14 | 482 |
| D12Des(Ol) | 4 | 442 |
| D12Des_2(Ol) | 2 | 362 |

To characterize the function of the *Ostreococcus lucimarinus* desaturase d6Des(OI) (=Δ6-desaturase), the open reading frame of the DNA is cloned downstream of the galactose-inducible GAL1 promoter of pYES2.1/V5-His-TOPO (Invitrogen), giving rise to the corresponding pYES2.1-d6Elo (OI) clone. Further desaturase genes from *Ostreococcus* can be cloned accordingly.

The *Saccharomyces cerevisiae* strain 334 is transformed with the vector pYES2.1-d6Elo(OI), by electroporation (1500 V). A yeast which is transformed with the blank vector pYES2 was used as control. The transformed yeasts were selected on complete minimal dropout uracil medium (CMdum) agar plates supplemented with 2% glucose.

After the selection, in each case three transformants were selected for the further functional expression.

To express the d6Elo(OI) desaturase, precultures consisting of in each case 5 ml of CMdum dropout uracil liquid medium supplemented with 2% (w/v) raffinose are initially inoculated with the selected transformants and incubated for 2 days at 30° C. and 200 rpm. Then, 5 ml of CMdum (dropout uracil) liquid medium supplemented with 2% raffinose and 300 µM various fatty acids are inoculated with the precultures to an $OD_{600}$ of 0.05. Expression is induced by the addition of 2% (w/v) galactose. The cultures are incubated for a further 96 hours at 20° C.

In the ClustalW sequence alignment, FIGS. 2 to 5 show sequence similarities with other algae (*Ostreococcus tauri, Thalassiosira pseudonana*) for the various desaturase amino acid sequences. Surprisingly, the *O. lucimarinus* sequences differ markedly in their amino acid sequence from the other algae.

TABLE 6

Sequence identities of individual desaturases

| Name of gene | SEQ ID | Organism | Identity in % |
|---|---|---|---|
| D4Des(OI) | 6 | O. lucimarinus | 100 |
|  |  | O. tauri | 69 |
|  |  | T. pseudonana | 20 |
| D5Des(OI) | 8 | D5Des_2(OI) | 23 |
|  |  | O. tauri_2 | 47 |
|  |  | T. pseudonana | 22 |
| D5Des_2(OI) | 10 | D5Des(OI) | 23 |
|  |  | O. tauri_2 | 14 |
|  |  | T. pseudonana | 19 |
| D6Des(OI) | 14 | O. lucimarinus | 100 |
|  |  | O. tauri | 62 |
|  |  | T. pseudonana | 15 |
| D12Des(OI) | 4 | D12Des_2(OI) | 51 |
|  |  | O. tauri | 82 |
|  |  | T. pseudonana | 34 |
| D12Des_2(OI) | 2 | D12Des(OI) | 51 |
|  |  | O. tauri | 47 |
|  |  | T. pseudonana | 32 |

The genes are characterized as follows:

To express the desaturases in yeast cells are harvested from the main cultures by centrifugation (100×g, 5 min, 20° C.) and washed with 100 mM $NaHCO_3$, pH 8.0 to remove residual medium and fatty acids. The yeast cell sediments are extracted for 4 hours using chloroform/methanol (1:1). The resulting organic phase is extracted with 0.45% NaCl, dried with $Na_2SO_4$ and evaporated in vacuo. Applying thin-layer chromatography (horizontal tank, chloroform:methanol:acetic acid 65:35:8), the lipid extract is separated further into the lipid classes phosphatidylcholine (PC), phosphatidylinosotol (PI), phosphatidylserine (PS), phosphatidylethanolamine (PE) and neutral lipids (NL). The various separated spots on the thin-layer plate are scraped off. For the gas-chromatographic analysis, fatty acid methyl esters (FAMEs) were prepared by acid methanolysis. To this end, the cell sediments are incubated for one hour at 80° C. together with 2 ml of 1 N methanolic sulfuric acid and 2% (v/v) dimethoxypropane. The FAMEs were extracted twice with petroleum ether (PE). To remove nonderivatized fatty acids, the organic phase is washed in each case once with 2 ml of 100 mM $NaHCO_3$, pH 8.0 and 2 ml of distilled water. Thereafter, the PE phases are dried with $Na_2SO_4$, evaporated under argon and taken up in 100 µl of PE. The samples are separated on a DB-23 capillary column (30 m, 0.25 mm, 0.25 µm, Agilent) in a Hewlett-Packard 6850 gas chromatograph equipped with flame ionization detector. The conditions for the GLC analysis are as follows: the oven temperature is programmed from 50° C. to 250° C. with a 5° C./min increment and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of D5Des_2 (OI):

To determine the activity and substrate specificity of D5Des_2 (OI) SEQ ID NO: 10, various fatty acids were fed (table 7). The substrates fed can be detected in large amounts in all of the transgenic yeasts. The transgenic yeasts reveal the synthesis of novel fatty acids, the products of the D5Des_2 (OI) reaction. This means that the gene D5Des_2 (OI) was expressed functionally.

TABLE 7

Feeding/conversion of different fatty acids by D5Des(OI_2).

| Sample name/fatty acid fed | Expected conversion | Substrate | Product |
|---|---|---|---|
| pYES | Control | — | — |
| pYES-d5Des(OI_GA) w/o FS | — |  |  |
| pYES-d5Des(OI_GA) 20:3 | 20:3 -> 20:4ara | 11.1 | 0.9 |

Figure 8:
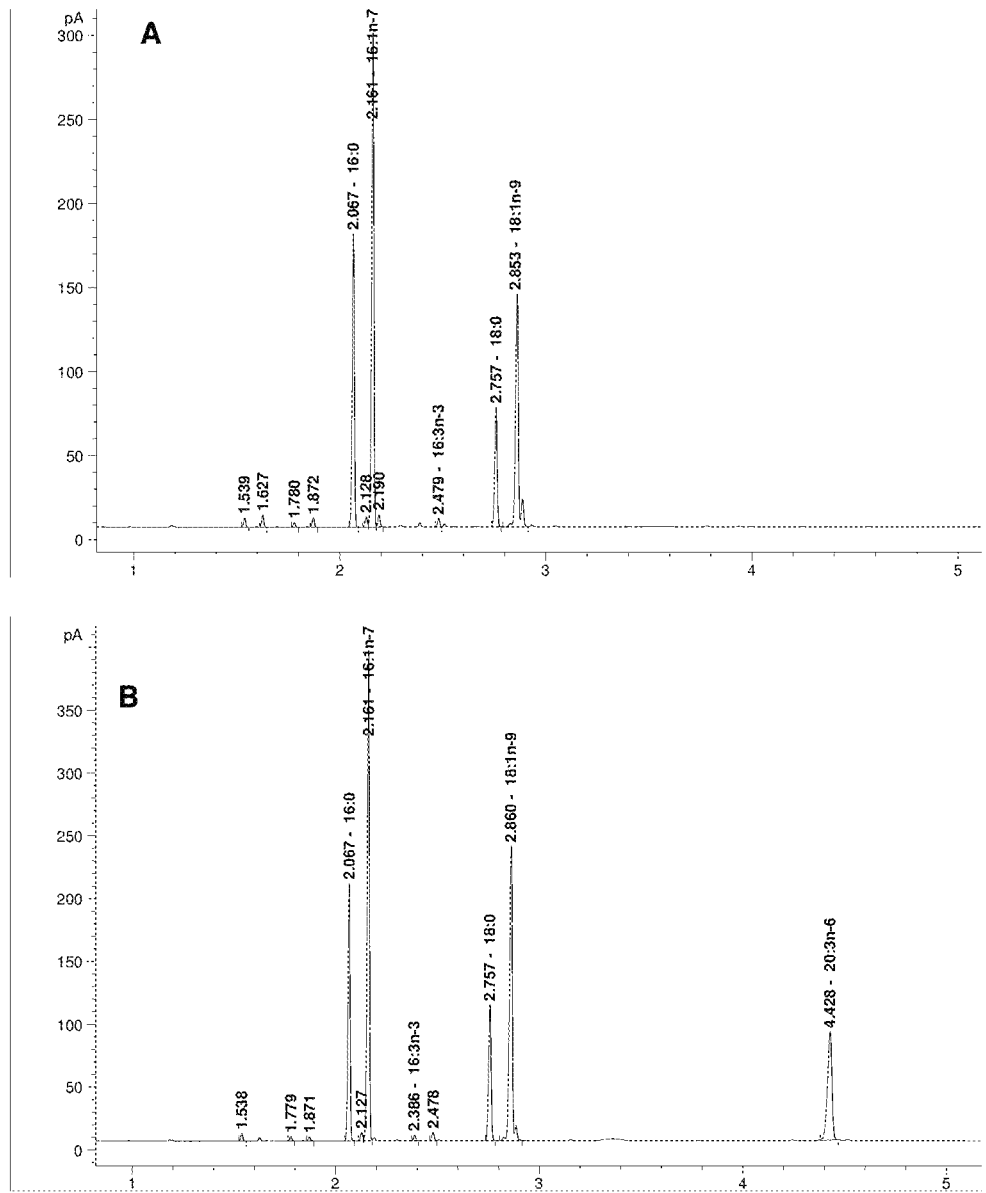
FIG. 8 shows the gas-chromatographic determination of the fatty acids from yeasts which have been transformed with the plasmid pYES (A, B) or pYES-D5Des(OI_2) (C). The fatty acid 20:3Δ5,8,11,14 was fed (B) and (C).
Figure 8:
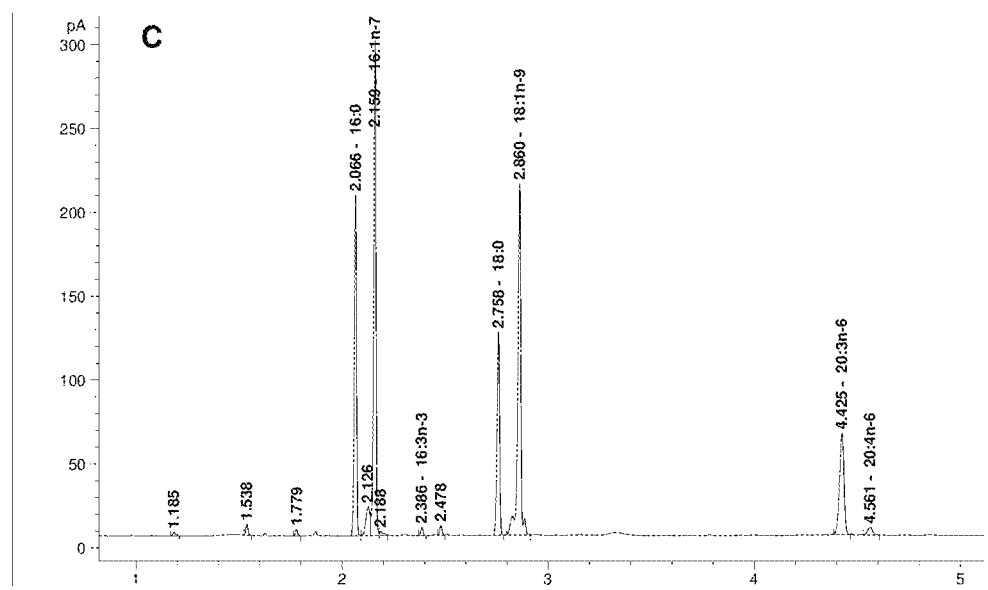

FIG. 8 shows the chromatograms of the individual experiments. In FIG. 8a, yeasts transformed with pYES were analyzed without the addition of fatty acids by way of control. In FIG. 8b, the pYES-transformed yeasts were fed the fatty acid 20:3Δ8,11,14. Here, the fed fatty acid can be detected in large amounts. The same experiment is carried out in FIG. 8C for yeasts transformed with the plasmid pYES-D5Des(OI_2). As opposed to FIG. 8B, it is possible to detect, in the yeasts with pYES-D5Des(OI_2), an additional fatty acid, which must be attributed to the D5Des(OI_2) activity. With reference to the activity, it is possible to characterize D5Des(OI_2) as a Δ5-desaturase.

Summary of the D5Des_2 (OI) Results:

It was possible to demonstrate in the yeast feeding experiments that the cloned gene D5Des_2 (OI) SEQ ID NO: 10 was expressed functionally and that it has desaturase activity. By reference to the fed fatty acid, it is possible to characterize D5Des_2 (OI) as a Δ5-desaturase, i.e. C20-fatty acids with a Δ8-double bond are dehydrogenated specifically in the Δ5 position.

Activity and Substrate Determination of D12Des(OI):

To determine the activity and substrate specificity of D12Des(OI) SEQ ID NO: 4, various fatty acids were fed (table 8). The substrates fed can be detected in large amounts in all of the transgenic yeasts. The transgenic yeasts reveal the synthesis of novel fatty acids, the products of the D12Des(OI) reaction. This means that the gene D12Des(OI) was expressed functionally.

TABLE 8

Feeding/conversion of different fatty acids by D12Des(Ol).

| Sample name/fatty acid fed | Expected conversion | Substrate | Product |
|---|---|---|---|
| pYES | Control | — | — |
| pYES-D12Des(Ol) | 18:1 –> 18:2 | 24.9 | 1.1 |
| pYES-D12Des(Ol) | 18:1 –> 18:2 | 24.1 | 1.0 |

Figure 9:
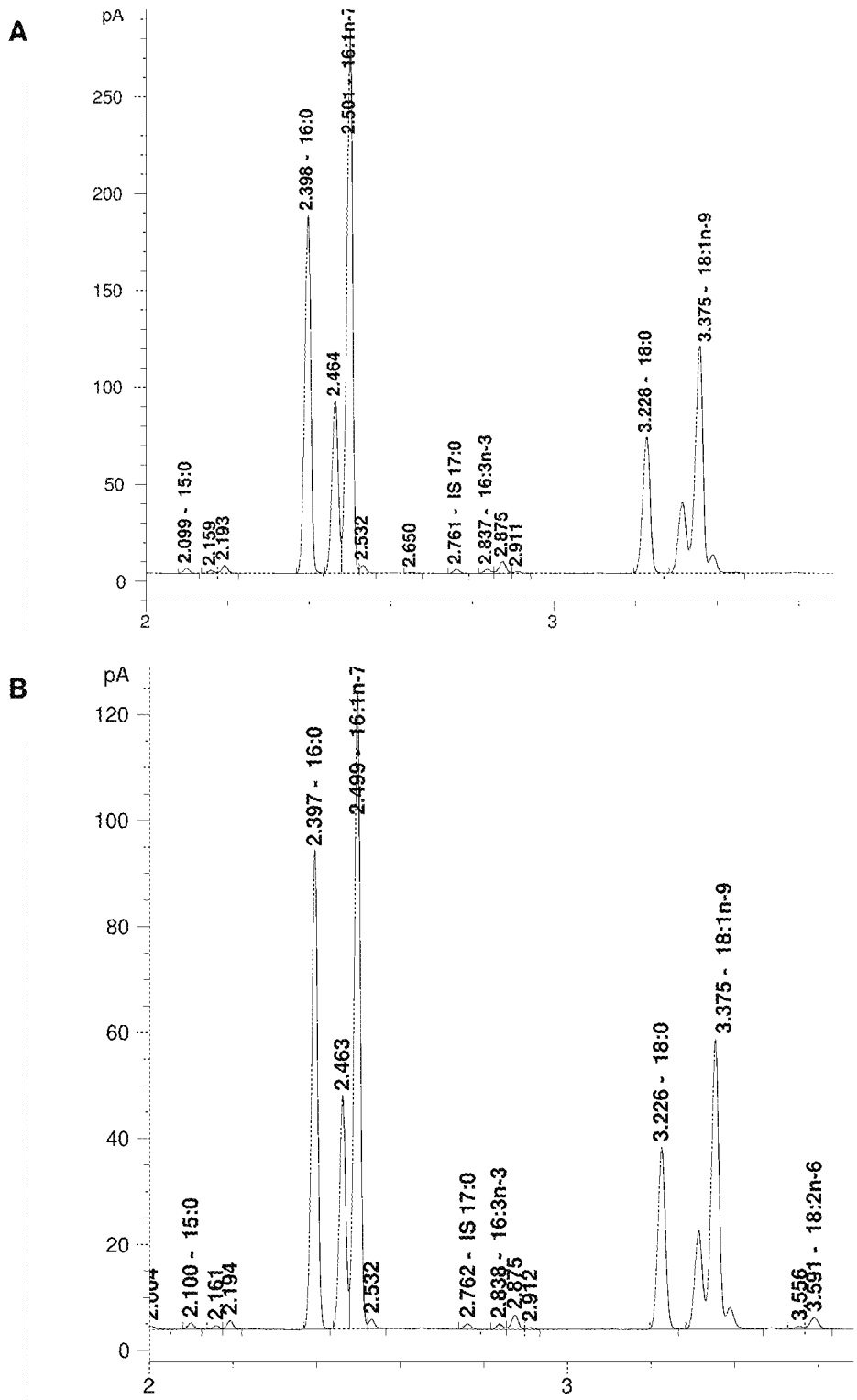
FIG. 9 shows the gas-chromatographic determination of the fatty acids from yeasts which have been transformed with the plasmid pYES (A) or pYES-D12Des(OI) (B).

FIG. 9 shows the chromatograms of the individual experiments. In FIG. 9a, yeasts transformed with pYES were analyzed without the addition of fatty acids by way of control. In FIG. 9b, the yeasts transformed with pYES-D12Des(OI) were analyzed. As opposed to FIG. 9a, it is possible to detect, in the yeasts with pYES-D12Des(OI), an additional fatty acid, which must be attributed to the D12Des(OI) activity. With reference to the activity, it is possible to characterize D12Des(OI) as a Δ12-desaturase.

Summary of the D12Des(OI) Results:

It was possible to demonstrate in the yeast feeding experiments that the cloned gene D12Des(OI) SEQ ID NO: 4 was expressed functionally and that it has desaturase activity. By reference to the fatty acid spectrum, it is possible to characterize D12Des(OI) as a Δ12-desaturase, i.e. C18-fatty acids with a Δ9-double bond are dehydrogenated specifically in the Δ12 position.

Activity and Substrate Determination of D5Des(OI):

To determine the activity and substrate specificity of D5Des(OI) SEQ ID NO: 8, various fatty acids were fed (table 9). The substrates fed can be detected in large amounts in all of the transgenic yeasts. The transgenic yeasts reveal the synthesis of novel fatty acids, the products of the D5Des(OI) reaction. This means that the gene D5Des(OI) was expressed functionally.

TABLE 9

Conversion of various fatty acids by D5Des(Ol)

| Sample | Expected conversion | Substrate | Product | Conversion rate [%] |
|---|---|---|---|---|
| d5Des(Ol_febit) | 20:3n-6 –> 20:4ara | 29.4 | 12.4 | 29.6 |
| d5Des(Ol_febit) | 20:3n-6 –> 20:4ara | 19.8 | 10.3 | 34.3 |
| d5Des(Ol_febit) | 20:4n-3 –> 20:5 | nd | 1.2 | >50% |

Figure 10:
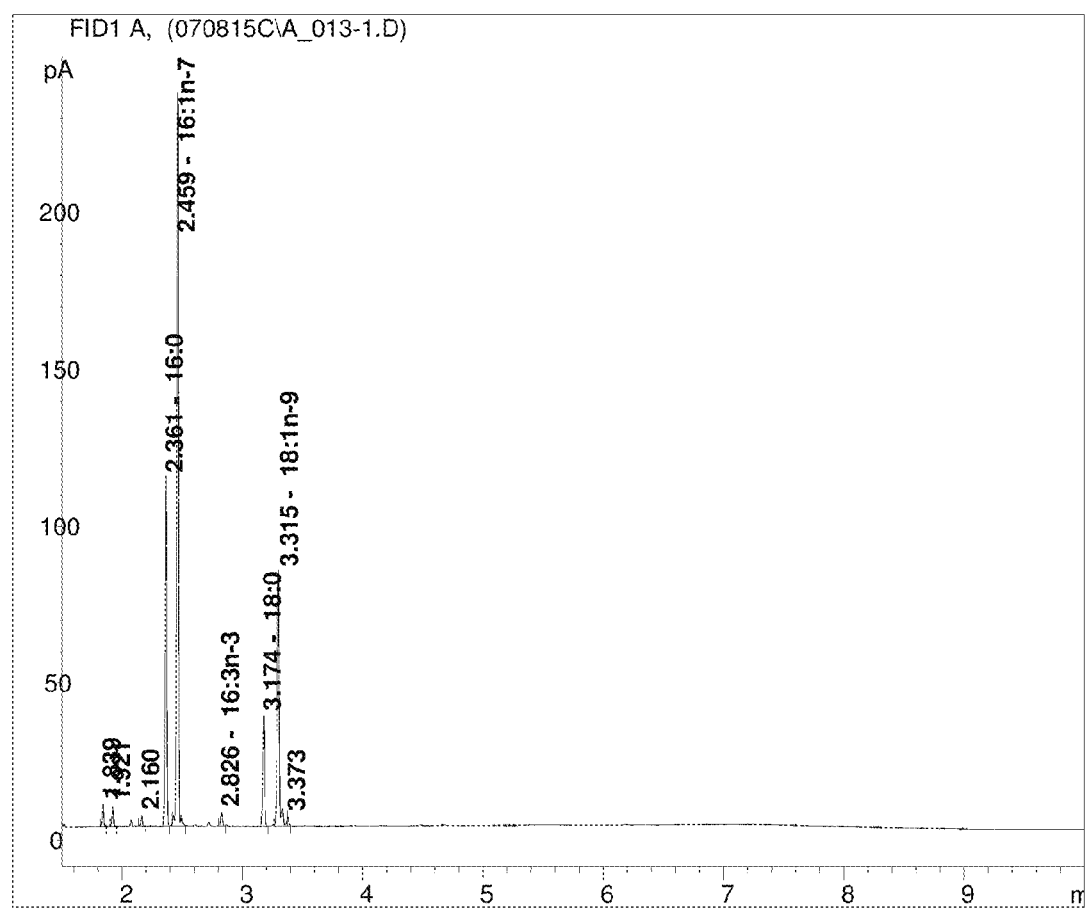
FIG. 10 shows the gas-chromatographic determination of the fatty acids from yeast. pYes-d5Des(OI_1) in yeast strain InvSc without addition of fatty acids (A); pYes-d5Des(OI_1) in yeast strain InvSc after addition of the fatty acid 20:3n-6 (B), pYes-d5Des(OI_1) in yeast strain InvSc after addition of the fatty acid 20:4n-3 (C).
Figure 10:
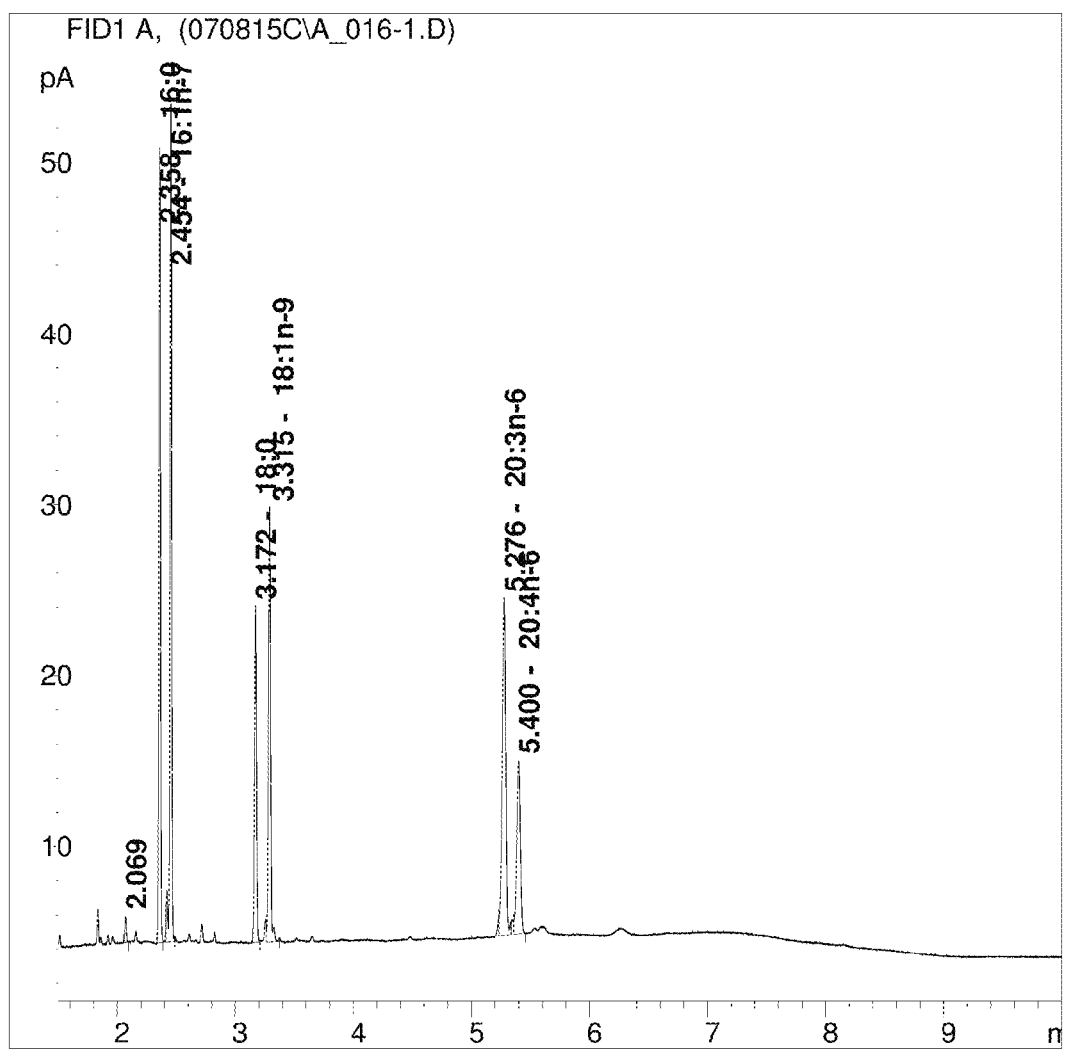
Figure 10:
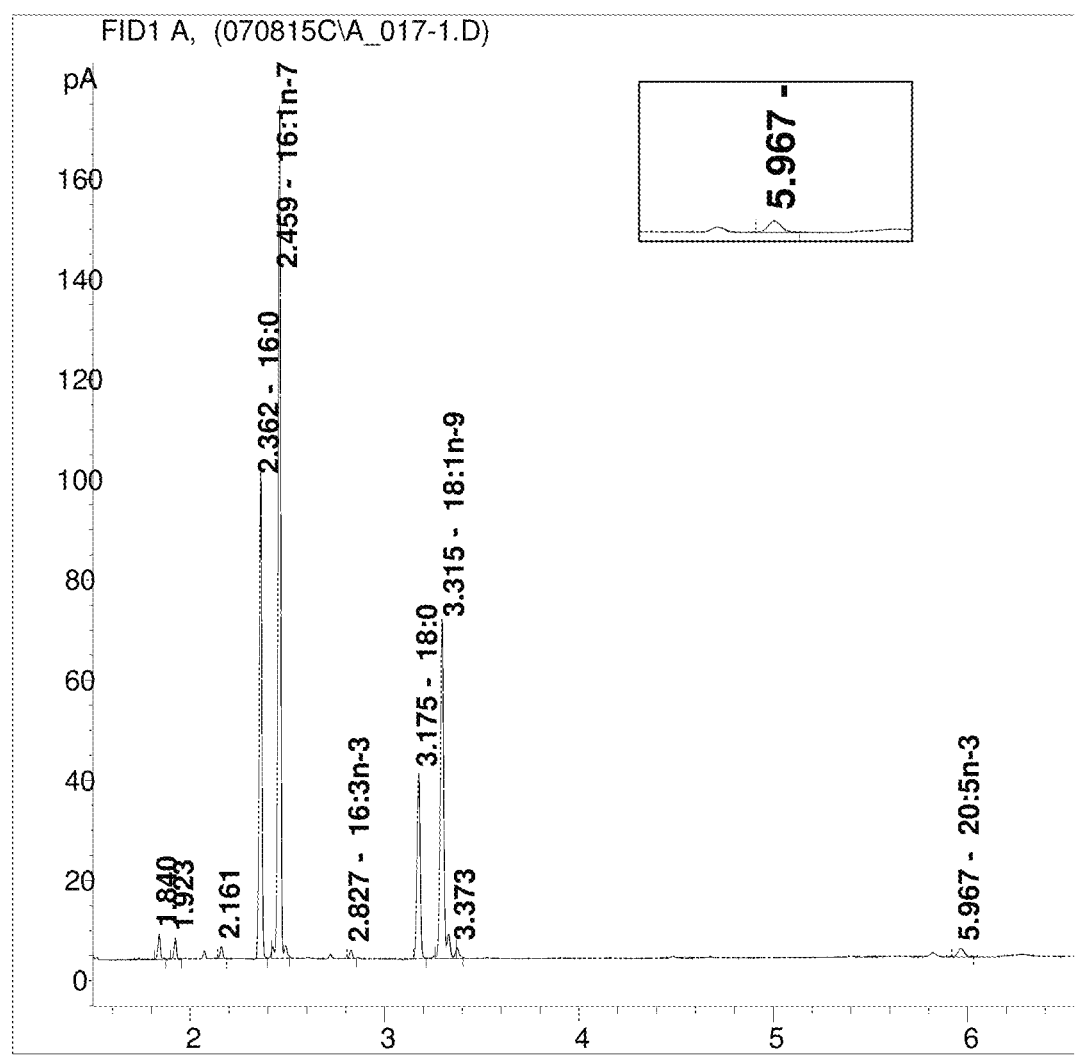

FIG. 10 shows the gas-chromatographic analysis of yeast feeding experiments. After expression of pYes-d5Des(OI_1) in yeast strain InvSc without the addition of fatty acids (FIG. 10A), no conversion of the existing fatty acids was detected. pYes-d5Des(OI_1) expression in yeast strain InvSc after addition of the fatty acid 20:3n-6 (B) leads to the specific conversion of 20:3n-6 into 20:4n-6 (arachidonic acid), and expression of pYes-d5Des(OI_1) in yeast strain InvSc after addition of the fatty acid 20:4n-3 (C) leads to the specific conversion of 20:4n-3 into 20:5n-3 (eicosapentaenoic acid). The specific incorporation of d5 double bonds into the fed fatty acids shows the d5-desaturase activity of d5Des(OI).

Summary of the D5Des(OI) Results:

It was possible to demonstrate in the yeast feeding experiments that the cloned gene D5Des(OI) SEQ ID NO: 8 was expressed functionally and that it has desaturase activity. By reference to the fatty acid spectrum, it is possible to characterize D5Des(OI) as a Δ5-desaturase, i.e. C20-fatty acids with a Δ8-double bond are dehydrogenated specifically in the Δ5 position.

We claim:

1. A fusion protein comprising a first heterologous polypeptide and a second heterologous polypeptide, wherein said first heterologous polypeptide is encoded by a polynucleotide selected from the group consisting of:
   (a) a polynucleotide comprising the nucleotide sequence of SEQ ID NO 9;
   (b) a polynucleotide encoding a polypeptide comprising the amino acid sequence of SEQ ID NO: 10; and
   (c) a polynucleotide encoding a polypeptide having at least 90% sequence identity to said polypeptide encoded by said polynucleotide of (a) or (b);
   wherein said first heterologous polypeptide has desaturase activity.

2. A method for producing a fusion protein comprising:
   (a) transforming a host cell with a polynucleotide encoding said fusion protein of claim 1;
   (b) expressing said fusion protein in said host cell; and
   (c) isolating said fusion protein from said host cell, wherein said host cell is from an organism selected from the group consisting of non-human animals, plants, multi-celled microorganisms, bacteria, and fungi.

3. The fusion protein of claim 1, wherein said second heterologous polypeptide is selected from the group consisting of:
   (a) an enzyme involved in the biosynthesis of lipids or fatty acids;
   (b) a marker protein; and
   (c) a purification tag.

4. The fusion protein of claim 3, wherein said enzyme involved in the biosynthesis of lipids or fatty acids is selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ5-elongase(s), Δ6-elongase(s), and Δ9-elongase(s).

5. The fusion protein of claim 3, wherein said marker protein is a fluorescent protein or an alkaline phosphatase.

6. The fusion protein of claim 3, wherein said purification tag is selected from the group consisting of FLAG tags, 6-histidine tags, and MYC tags.

7. The method of claim 2, wherein said host cell is a non-human animal cell or a plant cell.

8. A chemically modified polypeptide encoded by a polynucleotide selected from the group consisting of:
   (a) a polynucleotide comprising the nucleotide sequence of SEQ ID NO 9;
   (b) a polynucleotide encoding a polypeptide comprising the amino acid sequence of SEQ ID NO: 10; and
   (c) a polynucleotide encoding a polypeptide having at least 90% sequence identity to said polypeptide encoded by said polynucleotide of (a) or (b);
   wherein said chemically modified polypeptide has desaturase activity, and
   wherein said chemically modified polypeptide comprises one or more heterologous posttranslational modifications.

9. The chemically modified polypeptide of claim 8, wherein said one or more heterologous posttranslational modifications comprise phosphorylation, myristylation, and/or glycosylation.

* * * * *

SEQUENCE LISTING

```
<160> NUMBER OF SEQ ID NOS: 44

<210> SEQ ID NO 1
<211> LENGTH: 1696
<212> TYPE: DNA
<213> ORGANISM: Ostreococcus lucimarinus
<220> FEATURE:
<223> OTHER INFORMATION: Delta-12 desaturase
<220> FEATURE:
<221> NAME/KEY: CDS
<222> LOCATION: (374)..(1462)

<400> SEQUENCE: 1
cctttgtaac gccccgattc gttcgcgcgt ttcgctcgcc tcgcgtccgc cttcgcgcct      60
cgcgggataa ggctctcccg tcgcgtcgtc gcgttcgcac tcaccggcgc tcgcgcgtcg     120
accgctttcc cgcggcaccg cgatccacga acgacagtcg cgcgtcatgc tccgcgctct     180
gacgctcccg cgcgctcgcg cgctcccgcg cgccgcgttc tctcgctcga cgacgtcacg     240
tcgcgatcgc gcgcgcgtcg cccgcgccgc gcgcgccgac gccgcgacga cctacgacac     300
gtcgcgacac gaacaactgc gctcgggctt gaacgccaag gcgctgaacg ccgaggcgaa     360
gacgttcccg acg atg caa gag gtg ctg cgc gcg atc ccg agg gag tgc        409
            Met Gln Glu Val Leu Arg Ala Ile Pro Arg Glu Cys
              1               5                  10 ttc gag cgg gac acg gga aag tcg ctc gcg tac gcg gcg tgc tcg acg        457
Phe Glu Arg Asp Thr Gly Lys Ser Leu Ala Tyr Ala Ala Cys Ser Thr
         15                  20                  25 gcg atc acg ctg gcg tgc ggc gcg ctg gcg tgg gcg tgc gtg ccg gtg        505
```

```
Ala Ile Thr Leu Ala Cys Gly Ala Leu Ala Trp Ala Cys Val Pro Val
    30              35                  40 acg gcg gcg tat tgg ccg gtg tgg gtc gcg tac gcg ttc gtg acg gga        553
Thr Ala Ala Tyr Trp Pro Val Trp Val Ala Tyr Ala Phe Val Thr Gly
 45              50                  55                  60 acg gcg gcg acc ggg tgc tgg gtc gcg gcg cac gag tgc gga cac ggc        601
Thr Ala Ala Thr Gly Cys Trp Val Ala Ala His Glu Cys Gly His Gly
                 65                  70                  75 gcg ttt agc gac gat aaa acg att caa gac gcg gtg gga tac gcg ctg        649
Ala Phe Ser Asp Asp Lys Thr Ile Gln Asp Ala Val Gly Tyr Ala Leu
             80                  85                  90 cac tcg ttg ttg ttg gtg ccg tat ttt tcg tgg cag cgg tcg cac gcg        697
His Ser Leu Leu Leu Val Pro Tyr Phe Ser Trp Gln Arg Ser His Ala
         95                 100                 105 gtg cat cac tcg agg act aat cac gtg ctc gag gga gag acg cac gtg        745
Val His His Ser Arg Thr Asn His Val Leu Glu Gly Glu Thr His Val
     110                 115                 120 ccg gcg cgg ttg ggg acg gag gac gcg aac gtg atg ttc aag ttg cgc        793
Pro Ala Arg Leu Gly Thr Glu Asp Ala Asn Val Met Phe Lys Leu Arg
125                 130                 135                 140 ggg ttg ctc ggc gaa ggg ccg ttt acg ttt ttg aac ctc gtc gga gtg        841
Gly Leu Leu Gly Glu Gly Pro Phe Thr Phe Leu Asn Leu Val Gly Val
                145                 150                 155 ttc gcc ttg ggg tgg ccg att tat ttg ctc acc ggc gcc agc ggt ggg        889
Phe Ala Leu Gly Trp Pro Ile Tyr Leu Leu Thr Gly Ala Ser Gly Gly
            160                 165                 170 ccg gtt cgc ggg aac acg aac cac ttc ttg ccg ttc atg ggc gag aag        937
Pro Val Arg Gly Asn Thr Asn His Phe Leu Pro Phe Met Gly Glu Lys
        175                 180                 185 ggt aag cac gcg ttg ttc ccg ggg aag tgg gcg aag aag gtt tgg cag        985
Gly Lys His Ala Leu Phe Pro Gly Lys Trp Ala Lys Lys Val Trp Gln
    190                 195                 200 agc gac gtc ggc gtc gtg gcg gtt ttg gga gcg ctc gcg gcg tgg gcg       1033
Ser Asp Val Gly Val Val Ala Val Leu Gly Ala Leu Ala Ala Trp Ala
205                 210                 215                 220 gcg cac agc ggt gtc gcc acc gtc atg gcg ctc tac gtc gga ccg tac       1081
Ala His Ser Gly Val Ala Thr Val Met Ala Leu Tyr Val Gly Pro Tyr
                225                 230                 235 atg gtg acc aac ttt tgg ctc gtc ctg tac acg tgg ttg cag cac act       1129
Met Val Thr Asn Phe Trp Leu Val Leu Tyr Thr Trp Leu Gln His Thr
            240                 245                 250 gac gtg gac gtg ccg cac ttt gag ggc gac gac tgg aac ttg gtc aag       1177
Asp Val Asp Val Pro His Phe Glu Gly Asp Asp Trp Asn Leu Val Lys
        255                 260                 265 ggc gcg ttt atg acg att gat cgc ccg tac ggg cca gtg ttt gac ttt       1225
Gly Ala Phe Met Thr Ile Asp Arg Pro Tyr Gly Pro Val Phe Asp Phe
    270                 275                 280 ttg cac cac cgc atc ggc agc acg cac gtc gcg cat cac atc aac cac       1273
Leu His His Arg Ile Gly Ser Thr His Val Ala His His Ile Asn His
285                 290                 295                 300 acc atc ccg cac tac cac gcc aag aag gcc acc gag gcg ttg caa aag       1321
Thr Ile Pro His Tyr His Ala Lys Lys Ala Thr Glu Ala Leu Gln Lys
                305                 310                 315 gcg ttc ccg gat ctg tac ctg tat gac ccg acg ccc atc gcc acg gcg       1369
Ala Phe Pro Asp Leu Tyr Leu Tyr Asp Pro Thr Pro Ile Ala Thr Ala
            320                 325                 330 act tgg cgc gtc ggc agc aag tgc atc gcc gtc gtc aag aag ggc gac       1417
Thr Trp Arg Val Gly Ser Lys Cys Ile Ala Val Val Lys Lys Gly Asp
        335                 340                 345
```

-continued

```
gag tgg gtg ttc acg gac aag cag ctc gac ccg gtc gcg gcg tga         1462
Glu Trp Val Phe Thr Asp Lys Gln Leu Asp Pro Val Ala Ala
350                 355                 360 gcgcgcgtgt gacgaggata ttaagtttta gttagagaga cgagcattgt gattatgatt   1522
atatacgtgc gtgtttattt cacatgctgg aattcgccga agagcgaaac ggcgtattgt   1582
atcaccgctc gccccgcgag cgctctgctt cgtgtcgacg cgagaaaaat gtgcgctgct   1642
cggttttcga gcggcacaga gatcgaatga tctacagata ttaatcgcgt ttgt         1696
```

<210> SEQ ID NO 2
<211> LENGTH: 362
<212> TYPE: PRT
<213> ORGANISM: Ostreococcus lucimarinus

<400> SEQUENCE: 2

```
Met Gln Glu Val Leu Arg Ala Ile Pro Arg Glu Cys Phe Glu Arg Asp
1               5                   10                  15

Thr Gly Lys Ser Leu Ala Tyr Ala Ala Cys Ser Thr Ala Ile Thr Leu
            20                  25                  30

Ala Cys Gly Ala Leu Ala Trp Ala Cys Val Pro Val Thr Ala Ala Tyr
        35                  40                  45

Trp Pro Val Trp Val Ala Tyr Ala Phe Val Thr Gly Thr Ala Ala Thr
    50                  55                  60

Gly Cys Trp Val Ala Ala His Glu Cys Gly His Gly Ala Phe Ser Asp
65                  70                  75                  80

Asp Lys Thr Ile Gln Asp Ala Val Gly Tyr Ala Leu His Ser Leu Leu
                85                  90                  95

Leu Val Pro Tyr Phe Ser Trp Gln Arg Ser His Ala Val His His Ser
            100                 105                 110

Arg Thr Asn His Val Leu Glu Gly Glu Thr His Val Pro Ala Arg Leu
        115                 120                 125

Gly Thr Glu Asp Ala Asn Val Met Phe Lys Leu Arg Gly Leu Leu Gly
    130                 135                 140

Glu Gly Pro Phe Thr Phe Leu Asn Leu Val Gly Val Phe Ala Leu Gly
145                 150                 155                 160

Trp Pro Ile Tyr Leu Leu Thr Gly Ala Ser Gly Pro Val Arg Gly
                165                 170                 175

Asn Thr Asn His Phe Leu Pro Phe Met Gly Glu Lys Gly Lys His Ala
            180                 185                 190

Leu Phe Pro Gly Lys Trp Ala Lys Lys Val Trp Gln Ser Asp Val Gly
        195                 200                 205

Val Val Ala Val Leu Gly Ala Leu Ala Ala Trp Ala Ala His Ser Gly
    210                 215                 220

Val Ala Thr Val Met Ala Leu Tyr Val Gly Pro Tyr Met Val Thr Asn
225                 230                 235                 240

Phe Trp Leu Val Leu Tyr Thr Trp Leu Gln His Thr Asp Val Asp Val
                245                 250                 255

Pro His Phe Glu Gly Asp Asp Trp Asn Leu Val Lys Gly Ala Phe Met
            260                 265                 270

Thr Ile Asp Arg Pro Tyr Gly Pro Val Phe Asp Phe Leu His His Arg
        275                 280                 285

Ile Gly Ser Thr His Val Ala His His Ile Asn His Thr Ile Pro His
    290                 295                 300

Tyr His Ala Lys Lys Ala Thr Glu Ala Leu Gln Lys Ala Phe Pro Asp
305                 310                 315                 320
```

```
Leu Tyr Leu Tyr Asp Pro Thr Pro Ile Ala Thr Ala Thr Trp Arg Val
            325                 330                 335

Gly Ser Lys Cys Ile Ala Val Val Lys Lys Gly Asp Glu Trp Val Phe
            340                 345                 350

Thr Asp Lys Gln Leu Asp Pro Val Ala Ala
            355                 360

<210> SEQ ID NO 3
<211> LENGTH: 2039
<212> TYPE: DNA
<213> ORGANISM: Ostreococcus lucimarinus
<220> FEATURE:
<223> OTHER INFORMATION: Delta-12 desaturase
<220> FEATURE:
<221> NAME/KEY: CDS
<222> LOCATION: (572)..(1900)

<400> SEQUENCE: 3
cgttctcgcc ctcgcgcgcg tcgcgaccga cgtcttctac gcttaccgac gcgcccgcgt       60
ccgcgaccgc gcgtctggcg cgtgctcgag cgtgccgtcg attcgccgcg ccgccgtcgc      120
gcgcgcgcgt cgcgccgatc ccgcggcgcg ctcgccgacg cgcgttcgcc gcgcgcgcgc      180
gctcgatcga ccactcgcgc gcgccgaggc gcgacgcagt gcgggcgcgc gcgccgaggc      240
gcggtcggtc ggtcggtcgc cgcgtgatcg cgggcgctcc gatgatggcc atccaaagcg      300
ctcgaatgcg tggagcgacg cgatatcagc ctgcgaatgt tcacataaca taactctgac      360
tgcgaatgtc cgaacacgcg cgcgttcgcg tcgcggtcct ccgcgttcgt cgcgcacacg      420
cgcgcgcgcg aacgacgccc gacgtcgacg cgagcgacga gcgacgcaaa gtttttacgg      480
cgagaatcgc gcgcgcccag gacgcacgcg cgcccaggac gtctcgacgc gacgcgcacg      540
acgcaaacgc ggatagcgaa cgacgaggac g atg atg acg acg gca aac gtc          592
                                  Met Met Thr Thr Ala Asn Val
                                    1               5 tcg cgg gtc gcc gcg acg cgc gcg atg acg acg tcg acg acg tcg acg          640
Ser Arg Val Ala Ala Thr Arg Ala Met Thr Thr Ser Thr Thr Ser Thr
         10                  15                  20 cga cgc gtg atg gcg agt aaa tac atc gcg cga acg gcg acg acg acg          688
Arg Arg Val Met Ala Ser Lys Tyr Ile Ala Arg Thr Ala Thr Thr Thr
     25                  30                  35 acg acg gat gcg cgc gga cgg gcg cac cga cgc gcg ggc gcg atc gcg          736
Thr Thr Asp Ala Arg Gly Arg Ala His Arg Arg Ala Gly Ala Ile Ala
 40                  45                  50                  55 ctc ggt ggg ttt gaa gat ctt ccc agg agc ggg ctg gag gga cag gcg          784
Leu Gly Gly Phe Glu Asp Leu Pro Arg Ser Gly Leu Glu Gly Gln Ala
                 60                  65                  70 ctc acg ttc ccg cac aag aag gag ttc cct tcg cgc gcg gcg gtg ttg          832
Leu Thr Phe Pro His Lys Lys Glu Phe Pro Ser Arg Ala Ala Val Leu
             75                  80                  85 tca aac att ccc gat gaa tgc ttc aag aag gat acg gcc aag tcg ttg          880
Ser Asn Ile Pro Asp Glu Cys Phe Lys Lys Asp Thr Ala Lys Ser Leu
         90                  95                 100 atg tac gcc gcg gtg tcg acg gca atg acg gtg ggg tgc ggc ttg atc          928
Met Tyr Ala Ala Val Ser Thr Ala Met Thr Val Gly Cys Gly Leu Ile
     105                 110                 115 gcc gcg gcg aca ttg ccg ttg cag gcg gcg tgg tgg ccg gcg tgg ctt          976
Ala Ala Ala Thr Leu Pro Leu Gln Ala Ala Trp Trp Pro Ala Trp Leu
120                 125                 130                 135 gcg tac gcc gcg gtg aac ggt acg atc gcc act gga tgc tgg gtg atc         1024
Ala Tyr Ala Ala Val Asn Gly Thr Ile Ala Thr Gly Cys Trp Val Ile
```

-continued

```
                 140                 145                 150
gcg cac gag tgc ggc cat aac gcg ttc agc gat aac cga ttc att caa   1072
Ala His Glu Cys Gly His Asn Ala Phe Ser Asp Asn Arg Phe Ile Gln
            155                 160                 165 gac gcg gtc ggg tac gcg ttg cac tcg gcg ctc ctc gtg ccg tac ttt   1120
Asp Ala Val Gly Tyr Ala Leu His Ser Ala Leu Leu Val Pro Tyr Phe
        170                 175                 180 tcc tgg cag cgg tcg cac gct gtc cac cac tca cga acg aac cac ttg   1168
Ser Trp Gln Arg Ser His Ala Val His His Ser Arg Thr Asn His Leu
    185                 190                 195 acg gaa gga gaa acg cac gtg ccg tac gtc aag ggc gaa ttg aag ggt   1216
Thr Glu Gly Glu Thr His Val Pro Tyr Val Lys Gly Glu Leu Lys Gly
200                 205                 210                 215 gac ttg aac ctc aag gcg aag aag aac ttg ggt gag ggc ccg ttc gcg   1264
Asp Leu Asn Leu Lys Ala Lys Lys Asn Leu Gly Glu Gly Pro Phe Ala
                220                 225                 230 att ctt cag ctc gtc acc cac ttg gtt ttc ggc tgg ccg gcg tac ttg   1312
Ile Leu Gln Leu Val Thr His Leu Val Phe Gly Trp Pro Ala Tyr Leu
            235                 240                 245 ctc acc ggc gcg acg ggc ggg agc gcg aga ggc gtc acc aac cat ttc   1360
Leu Thr Gly Ala Thr Gly Gly Ser Ala Arg Gly Val Thr Asn His Phe
        250                 255                 260 ttg cct aac atc aat acc ggc gct ttg gag ctg ttc ccg gga agc tgg   1408
Leu Pro Asn Ile Asn Thr Gly Ala Leu Glu Leu Phe Pro Gly Ser Trp
    265                 270                 275 aag aag aaa gtg tac tac tcg gac att ggt gtt ttc gcg ttc gtc ggc   1456
Lys Lys Lys Val Tyr Tyr Ser Asp Ile Gly Val Phe Ala Phe Val Gly
280                 285                 290                 295 gtt ctc gcc gcc tgg gtt gcc cag tgc ggt tgg gct ccg ttt gtc gcc   1504
Val Leu Ala Ala Trp Val Ala Gln Cys Gly Trp Ala Pro Phe Val Ala
                300                 305                 310 ctg tac ctg gga ccg tat ttg ttt gtc aac ttt tgg ctc gtc ttg tac   1552
Leu Tyr Leu Gly Pro Tyr Leu Phe Val Asn Phe Trp Leu Val Leu Tyr
            315                 320                 325 acg tgg ttg cag cac acc gat gtg gac gtc caa cac ttg gcc gcg gac   1600
Thr Trp Leu Gln His Thr Asp Val Asp Val Gln His Leu Ala Ala Asp
        330                 335                 340 gag tgg tcg tac atc aag ggc gca ttc ttg acg atc gac cgc ccg tac   1648
Glu Trp Ser Tyr Ile Lys Gly Ala Phe Leu Thr Ile Asp Arg Pro Tyr
    345                 350                 355 gga ccc gtg ttt gac ttc tta cac cac cgc atc gga tcc act cac gtg   1696
Gly Pro Val Phe Asp Phe Leu His His Arg Ile Gly Ser Thr His Val
360                 365                 370                 375 gcg cac cac gtt gag tgc gcg att ccg cac tac aag gcg gtc gaa gcg   1744
Ala His His Val Glu Cys Ala Ile Pro His Tyr Lys Ala Val Glu Ala
                380                 385                 390 acc gag gcg ttg aag acg aag tat ccg gag tac tat ttg tat gac ccg   1792
Thr Glu Ala Leu Lys Thr Lys Tyr Pro Glu Tyr Tyr Leu Tyr Asp Pro
            395                 400                 405 acg ccg att tgg gcg gca atg atg cgc gtc gcg tcc aag tgc gtc gct   1840
Thr Pro Ile Trp Ala Ala Met Met Arg Val Ala Ser Lys Cys Val Ala
        410                 415                 420 gtc gag aag cgc ggc gaa ggc aag ggt gcg atg tgg act ttc act gac   1888
Val Glu Lys Arg Gly Glu Gly Lys Gly Ala Met Trp Thr Phe Thr Asp
    425                 430                 435 ggc acg gcg taa ttatgaatga ttattagtat ttagcagctc ttcgcgcaca       1940
Gly Thr Ala
440 cgcagacaca aacattttat tgatacacac taacgaaact actacgtgcg attccagttg  2000
```
cgaaagacga gtacacactt gtacacacta acgaaacta 2039

<210> SEQ ID NO 4
<211> LENGTH: 442
<212> TYPE: PRT
<213> ORGANISM: Ostreococcus lucimarinus

<400> SEQUENCE: 4

Met Met Thr Thr Ala Asn Val Ser Arg Val Ala Thr Arg Ala Met
1               5                   10                  15

Thr Thr Ser Thr Thr Ser Thr Arg Arg Val Met Ala Ser Lys Tyr Ile
            20                  25                  30

Ala Arg Thr Ala Thr Thr Thr Thr Asp Ala Arg Gly Arg Ala His
        35                  40                  45

Arg Arg Ala Gly Ala Ile Ala Leu Gly Gly Phe Glu Asp Leu Pro Arg
    50                  55                  60

Ser Gly Leu Glu Gly Gln Ala Leu Thr Phe Pro His Lys Lys Glu Phe
65                  70                  75                  80

Pro Ser Arg Ala Ala Val Leu Ser Asn Ile Pro Asp Glu Cys Phe Lys
                85                  90                  95

Lys Asp Thr Ala Lys Ser Leu Met Tyr Ala Ala Val Ser Thr Ala Met
            100                 105                 110

Thr Val Gly Cys Gly Leu Ile Ala Ala Ala Thr Leu Pro Leu Gln Ala
        115                 120                 125

Ala Trp Trp Pro Ala Trp Leu Ala Tyr Ala Ala Val Asn Gly Thr Ile
    130                 135                 140

Ala Thr Gly Cys Trp Val Ile Ala His Glu Cys Gly His Asn Ala Phe
145                 150                 155                 160

Ser Asp Asn Arg Phe Ile Gln Asp Ala Val Gly Tyr Ala Leu His Ser
                165                 170                 175

Ala Leu Leu Val Pro Tyr Phe Ser Trp Gln Arg Ser His Ala Val His
            180                 185                 190

His Ser Arg Thr Asn His Leu Thr Glu Gly Glu Thr His Val Pro Tyr
        195                 200                 205

Val Lys Gly Glu Leu Lys Gly Asp Leu Asn Leu Lys Ala Lys Lys Asn
    210                 215                 220

Leu Gly Glu Gly Pro Phe Ala Ile Leu Gln Leu Val Thr His Leu Val
225                 230                 235                 240

Phe Gly Trp Pro Ala Tyr Leu Leu Thr Gly Ala Thr Gly Gly Ser Ala
                245                 250                 255

Arg Gly Val Thr Asn His Phe Leu Pro Asn Ile Asn Thr Gly Ala Leu
            260                 265                 270

Glu Leu Phe Pro Gly Ser Trp Lys Lys Lys Val Tyr Tyr Ser Asp Ile
        275                 280                 285

Gly Val Phe Ala Phe Val Gly Val Leu Ala Ala Trp Val Ala Gln Cys
    290                 295                 300

Gly Trp Ala Pro Phe Val Ala Leu Tyr Leu Gly Pro Tyr Leu Phe Val
305                 310                 315                 320

Asn Phe Trp Leu Val Leu Tyr Thr Trp Leu Gln His Thr Asp Val Asp
                325                 330                 335

Val Gln His Leu Ala Ala Asp Glu Trp Ser Tyr Ile Lys Gly Ala Phe
            340                 345                 350

Leu Thr Ile Asp Arg Pro Tyr Gly Pro Val Phe Asp Phe Leu His His
        355                 360                 365

```
Arg Ile Gly Ser Thr His Val Ala His His Val Glu Cys Ala Ile Pro
            370                 375                 380

His Tyr Lys Ala Val Glu Ala Thr Glu Ala Leu Lys Thr Lys Tyr Pro
385                 390                 395                 400

Glu Tyr Tyr Leu Tyr Asp Pro Thr Pro Ile Trp Ala Ala Met Met Arg
                405                 410                 415

Val Ala Ser Lys Cys Val Ala Val Glu Lys Arg Gly Glu Gly Lys Gly
            420                 425                 430

Ala Met Trp Thr Phe Thr Asp Gly Thr Ala
            435                 440

<210> SEQ ID NO 5
<211> LENGTH: 1737
<212> TYPE: DNA
<213> ORGANISM: Ostreococcus lucimarinus
<220> FEATURE:
<223> OTHER INFORMATION: Delta-4 desaturase
<220> FEATURE:
<221> NAME/KEY: CDS
<222> LOCATION: (218)..(1618)

<400> SEQUENCE: 5
gcgcaccgtc gcgcgcgcgt tcgcgacgac gacgacgtcg agcgcgaggt gtgattatcg      60
ccgtcgagcg acgacgacgc gcgcgacgac gagcgcggtg cgcgcggacg cgcggcgcgc     120
gcgatcgggg aggtatgcga tcgttccgcg atcgatcgag ggcgaaggga acgccgcggt     180
cgtcgaaaga agcgtcgagg gcgaggaggg ggagaag atg atg tcc ctg gag gcg     235
                                         Met Met Ser Leu Glu Ala
                                           1               5 aga cgc gag gcg ctg agg ttg ccg cgc ccg gac gtc gcg gcg ccg ggg      283
Arg Arg Glu Ala Leu Arg Leu Pro Arg Pro Asp Val Ala Ala Pro Gly
        10                  15                  20 atg gag gat ccg tgg aac gat gag aag tgg caa aag gtg aag tgg acg      331
Met Glu Asp Pro Trp Asn Asp Glu Lys Trp Gln Lys Val Lys Trp Thr
    25                  30                  35 gtg ttt cga gac gtg gcg tac gac ctc gga ccg ttc ttt gag aag cat      379
Val Phe Arg Asp Val Ala Tyr Asp Leu Gly Pro Phe Phe Glu Lys His
40                  45                  50 ccg ggc ggg aac tgg ttg ttg aac ctc gcc atc ggt cgc gac tgc acg      427
Pro Gly Gly Asn Trp Leu Leu Asn Leu Ala Ile Gly Arg Asp Cys Thr
55                  60                  65                  70 gcg ctc atg gaa tcc tat cac ttg cga cca gag gtg gcg acg gcg cgc      475
Ala Leu Met Glu Ser Tyr His Leu Arg Pro Glu Val Ala Thr Ala Arg
                75                  80                  85 ttc agg atg tta ccc aag ctc gag ggg ttc ccg gtc gac gcc gtg gcg      523
Phe Arg Met Leu Pro Lys Leu Glu Gly Phe Pro Val Asp Ala Val Ala
            90                  95                 100 aag tca ccg aga ccg aac gat tcg ccg ctg tac aac aac atc cgc aat      571
Lys Ser Pro Arg Pro Asn Asp Ser Pro Leu Tyr Asn Asn Ile Arg Asn
        105                 110                 115 cgc gtt cgc gag gaa ctt ttc ccg gaa gaa ggg aag aac aaa cac aga      619
Arg Val Arg Glu Glu Leu Phe Pro Glu Glu Gly Lys Asn Lys His Arg
    120                 125                 130 atg ggt ggc gac cac gcg acg ata acg att ttg tct ttc gcc gcg ttt      667
Met Gly Gly Asp His Ala Thr Ile Thr Ile Leu Ser Phe Ala Ala Phe
135                 140                 145                 150 gcg tac ggt gtg tac gcc acc atc ccg ggc ttt ctc tcg ggt tgc ctc      715
Ala Tyr Gly Val Tyr Ala Thr Ile Pro Gly Phe Leu Ser Gly Cys Leu
                155                 160                 165
```

| | |
|---|---|
| ctt ggc tta gct ggt gcg tgg atc ggg ctc acg att cag cat tgc gcc<br>Leu Gly Leu Ala Gly Ala Trp Ile Gly Leu Thr Ile Gln His Cys Ala<br>     170                        175                  180 | 763 |
| aat cac ggg gcg atg tca ccg tcg ccc gcc gtc aac ggc gtc ctc ggt<br>Asn His Gly Ala Met Ser Pro Ser Pro Ala Val Asn Gly Val Leu Gly<br>185                       190                       195 | 811 |
| ttg acg aac gat ctc atc ggc ggc tcg tct ttg atg tgg cga tac cac<br>Leu Thr Asn Asp Leu Ile Gly Gly Ser Ser Leu Met Trp Arg Tyr His<br>    200                       205                  210 | 859 |
| cac cag gtg agc cac cac att cac tgc aac gac aat gct atg gat caa<br>His Gln Val Ser His His Ile His Cys Asn Asp Asn Ala Met Asp Gln<br>215                       220                    225                  230 | 907 |
| gac gtg tac acc gcc atg cct ctc ttg cgt ttc gac gct cgt cgt ccc<br>Asp Val Tyr Thr Ala Met Pro Leu Leu Arg Phe Asp Ala Arg Arg Pro<br>               235                       240                  245 | 955 |
| aag gcg tgg tac cac cgc ttc cag cac tgg tac atg ttc ttg gcc ttt<br>Lys Ala Trp Tyr His Arg Phe Gln His Trp Tyr Met Phe Leu Ala Phe<br>250                       255                       260 | 1003 |
| ccg ttg ttg cag gtg gcg ttc caa gtc ggc gac atc gtc ggt ttg ttc<br>Pro Leu Leu Gln Val Ala Phe Gln Val Gly Asp Ile Val Gly Leu Phe<br>    265                       270                  275 | 1051 |
| act cgc gat acc gaa ggc gca aag ctc cac ggg gcg acc act tgg gaa<br>Thr Arg Asp Thr Glu Gly Ala Lys Leu His Gly Ala Thr Thr Trp Glu<br>280                       285                       290 | 1099 |
| ctt gcc acc gta gtt atc ggc aag ttt gtg cac ttc ggt ttg ttg gct<br>Leu Ala Thr Val Val Ile Gly Lys Phe Val His Phe Gly Leu Leu Ala<br>295                       300                    305                310 | 1147 |
| gca cct ttg atg agc cac gcg gct tcc gcc gtc gtc gcc ggc atc gtc<br>Ala Pro Leu Met Ser His Ala Ala Ser Ala Val Val Ala Gly Ile Val<br>               315                       320                  325 | 1195 |
| ggt ttc atg gcg tgc caa gga gtc gtc ctc gcg tgt acg ttc gcg gtg<br>Gly Phe Met Ala Cys Gln Gly Val Val Leu Ala Cys Thr Phe Ala Val<br>330                       335                       340 | 1243 |
| agt cac aac gtg ccc gag gcc aaa ctc cct gaa gat acc ggt gga gag<br>Ser His Asn Val Pro Glu Ala Lys Leu Pro Glu Asp Thr Gly Gly Glu<br>    345                       350                  355 | 1291 |
| gcg tgg gaa aga gat tgg ggc gtg cag cag ttg gtg act agc gct gac<br>Ala Trp Glu Arg Asp Trp Gly Val Gln Gln Leu Val Thr Ser Ala Asp<br>360                       365                       370 | 1339 |
| tgg ggt gga aag att gga aac ttt ttc acc ggc ggt ctg aac ttg caa<br>Trp Gly Gly Lys Ile Gly Asn Phe Phe Thr Gly Gly Leu Asn Leu Gln<br>375                       380                    385                390 | 1387 |
| gtc gag cat cac ctg ttc ccg gcg att tgc ttt gtg cac tac ccc gcg<br>Val Glu His His Leu Phe Pro Ala Ile Cys Phe Val His Tyr Pro Ala<br>               395                       400                  405 | 1435 |
| atc gcg aaa att gtc gcg gaa gaa gcg gcg aag atg ggc att cct tac<br>Ile Ala Lys Ile Val Ala Glu Glu Ala Ala Lys Met Gly Ile Pro Tyr<br>          410                       415                  420 | 1483 |
| tcg tca tac aga aca ctt ccc ggc att ttc gtc gcg ttc tgg aaa ttc<br>Ser Ser Tyr Arg Thr Leu Pro Gly Ile Phe Val Ala Phe Trp Lys Phe<br>425                       430                    435 | 1531 |
| gtc aga gac atg ggc acg gcg gag caa atc gac gac gtt tta ctt ccg<br>Val Arg Asp Met Gly Thr Ala Glu Gln Ile Asp Asp Val Leu Leu Pro<br>440                       445                       450 | 1579 |
| aag ttc gcg aac ccg caa ctt tcg cca gcc atc aat tag aattataact<br>Lys Phe Ala Asn Pro Gln Leu Ser Pro Ala Ile Asn<br>455                     460                    465 | 1628 |
| taccttacgc gcttgttgac ttcaaacgag caaacgacag aaatacgatt attgtgatat | 1688 |
| acttacacct ccgcctcatc attgttttga tctaattcta acttacaaa | 1737 |

<210> SEQ ID NO 6
<211> LENGTH: 466
<212> TYPE: PRT
<213> ORGANISM: Ostreococcus lucimarinus

<400> SEQUENCE: 6

Met Met Ser Leu Glu Ala Arg Arg Glu Ala Leu Arg Leu Pro Arg Pro
1               5                   10                  15

Asp Val Ala Ala Pro Gly Met Glu Asp Pro Trp Asn Asp Glu Lys Trp
            20                  25                  30

Gln Lys Val Lys Trp Thr Val Phe Arg Asp Val Ala Tyr Asp Leu Gly
        35                  40                  45

Pro Phe Phe Glu Lys His Pro Gly Gly Asn Trp Leu Leu Asn Leu Ala
    50                  55                  60

Ile Gly Arg Asp Cys Thr Ala Leu Met Glu Ser Tyr His Leu Arg Pro
65                  70                  75                  80

Glu Val Ala Thr Ala Arg Phe Arg Met Leu Pro Lys Leu Glu Gly Phe
                85                  90                  95

Pro Val Asp Ala Val Ala Lys Ser Pro Arg Pro Asn Asp Ser Pro Leu
            100                 105                 110

Tyr Asn Asn Ile Arg Asn Arg Val Arg Glu Glu Leu Phe Pro Glu Glu
        115                 120                 125

Gly Lys Asn Lys His Arg Met Gly Gly Asp His Ala Thr Ile Thr Ile
    130                 135                 140

Leu Ser Phe Ala Ala Phe Ala Tyr Gly Val Tyr Ala Thr Ile Pro Gly
145                 150                 155                 160

Phe Leu Ser Gly Cys Leu Leu Gly Leu Ala Gly Ala Trp Ile Gly Leu
                165                 170                 175

Thr Ile Gln His Cys Ala Asn His Gly Ala Met Ser Pro Ser Pro Ala
            180                 185                 190

Val Asn Gly Val Leu Gly Leu Thr Asn Asp Leu Ile Gly Gly Ser Ser
        195                 200                 205

Leu Met Trp Arg Tyr His His Gln Val Ser His His Ile His Cys Asn
    210                 215                 220

Asp Asn Ala Met Asp Gln Asp Val Tyr Thr Ala Met Pro Leu Leu Arg
225                 230                 235                 240

Phe Asp Ala Arg Arg Pro Lys Ala Trp Tyr His Arg Phe Gln His Trp
                245                 250                 255

Tyr Met Phe Leu Ala Phe Pro Leu Leu Gln Val Ala Phe Gln Val Gly
            260                 265                 270

Asp Ile Val Gly Leu Phe Thr Arg Asp Thr Glu Gly Ala Lys Leu His
        275                 280                 285

Gly Ala Thr Thr Trp Glu Leu Ala Thr Val Val Ile Gly Lys Phe Val
    290                 295                 300

His Phe Gly Leu Leu Ala Ala Pro Leu Met Ser His Ala Ala Ser Ala
305                 310                 315                 320

Val Val Ala Gly Ile Val Gly Phe Met Ala Cys Gln Gly Val Val Leu
                325                 330                 335

Ala Cys Thr Phe Ala Val Ser His Asn Val Pro Glu Ala Lys Leu Pro
            340                 345                 350

Glu Asp Thr Gly Gly Glu Ala Trp Glu Arg Asp Trp Gly Val Gln Gln
        355                 360                 365

Leu Val Thr Ser Ala Asp Trp Gly Gly Lys Ile Gly Asn Phe Phe Thr

```
                  370                 375                 380
Gly Gly Leu Asn Leu Gln Val Glu His His Leu Phe Pro Ala Ile Cys
385                 390                 395                 400

Phe Val His Tyr Pro Ala Ile Ala Lys Ile Val Ala Glu Glu Ala Ala
                405                 410                 415

Lys Met Gly Ile Pro Tyr Ser Ser Tyr Arg Thr Leu Pro Gly Ile Phe
                420                 425                 430

Val Ala Phe Trp Lys Phe Val Arg Asp Met Gly Thr Ala Glu Gln Ile
                435                 440                 445

Asp Asp Val Leu Leu Pro Lys Phe Ala Asn Pro Gln Leu Ser Pro Ala
    450                 455                 460

Ile Asn
465

<210> SEQ ID NO 7
<211> LENGTH: 1604
<212> TYPE: DNA
<213> ORGANISM: Ostreococcus lucimarinus
<220> FEATURE:
<223> OTHER INFORMATION: Delta-5 desaturase
<220> FEATURE:
<221> NAME/KEY: CDS
<222> LOCATION: (156)..(1535)

<400> SEQUENCE: 7
tcactcagcc gtccgcgatc cgcgcgcgcg tcgcgttcga ccgcgtcgcg cccagaacga      60
acgtagaacc gaatcgcccg tcccgcgtcg cgcggatgaa tgcaaaaaac aagatgactg     120
gatgacgtcc cgcgccacac gatcgcgcgc gcgtc atg ccc tcc gcc gcg cgc       173
                                        Met Pro Ser Ala Ala Arg
                                         1               5 tcc cga gcg tcg aag cgc gcg aac gcg acg acg gac gtc gcg acg acc      221
Ser Arg Ala Ser Lys Arg Ala Asn Ala Thr Thr Asp Val Ala Thr Thr
              10                  15                  20 gct ccc gag gcg acg ctc gac ccg acg cgc gcg tac acg cgc tat cgc      269
Ala Pro Glu Ala Thr Leu Asp Pro Thr Arg Ala Tyr Thr Arg Tyr Arg
          25                  30                  35 ggc gtc gtc tac gac gtc acc gag ttt cag cat cgc cat ccc ggc ggc      317
Gly Val Val Tyr Asp Val Thr Glu Phe Gln His Arg His Pro Gly Gly
     40                  45                  50 gcg caa ttg ctc tcg ctc tgc gtc gga cgc gac gcg acg atc ctg atc      365
Ala Gln Leu Leu Ser Leu Cys Val Gly Arg Asp Ala Thr Ile Leu Ile
 55                  60                  65                  70 gag agc cat cac ttg cga cct gag gtg gtg cgc aag tac atg aag acg      413
Glu Ser His His Leu Arg Pro Glu Val Val Arg Lys Tyr Met Lys Thr
                 75                  80                  85 ctg ccc gtg gtg gag ggc gcg gcg ggc gcg ttc ggg aag gag gag acg      461
Leu Pro Val Val Glu Gly Ala Ala Gly Ala Phe Gly Lys Glu Glu Thr
             90                  95                 100 ttt ccg aaa ccg ctc gat tcg gcg gtg tat cga gcg ata caa cgc cga      509
Phe Pro Lys Pro Leu Asp Ser Ala Val Tyr Arg Ala Ile Gln Arg Arg
        105                 110                 115 gtg cga gat gaa gtc gtg gaa ccg atg aaa gca aag tct gga agg gag      557
Val Arg Asp Glu Val Val Glu Pro Met Lys Ala Lys Ser Gly Arg Glu
    120                 125                 130 gca cac gga cgc ggt ggg tgc gtc gtg gac gcg ggg gtg gtc gtg ttg      605
Ala His Gly Arg Gly Gly Cys Val Val Asp Ala Gly Val Val Val Leu
135                 140                 145                 150 acg ttt gtc gcg gcg atg gtg gcg tat tgg cgc gcg ccc tcg gcg ctc      653
Thr Phe Val Ala Ala Met Val Ala Tyr Trp Arg Ala Pro Ser Ala Leu
```

```
              155                 160                 165
acg ggg tgc gcg ttg gga ctg gcg ggg tac tgg agc ggc act ggg ttg        701
Thr Gly Cys Ala Leu Gly Leu Ala Gly Tyr Trp Ser Gly Thr Gly Leu
        170                 175                 180 caa cac acg gcg aat cac gga gga ttg gcg aag agt gga ttt tgg aat        749
Gln His Thr Ala Asn His Gly Gly Leu Ala Lys Ser Gly Phe Trp Asn
                185                 190                 195 cag ttt tgg gga tgg ctc ggg aac gac gtg gcg atc ggg aag agt tcg        797
Gln Phe Trp Gly Trp Leu Gly Asn Asp Val Ala Ile Gly Lys Ser Ser
    200                 205                 210 gtg gag tgg cgg tat cat cac atg gtg agc cat cac tcg tac tgc aac        845
Val Glu Trp Arg Tyr His His Met Val Ser His His Ser Tyr Cys Asn
215                 220                 225                 230 gac gcc gat ctc gat caa gac gtg tac acc gcg tta ccg ttg ttg cga        893
Asp Ala Asp Leu Asp Gln Asp Val Tyr Thr Ala Leu Pro Leu Leu Arg
                235                 240                 245 ctt gac cca tcg cag gag ttg aag tgg ttc cat cgg tac caa gcg ttt        941
Leu Asp Pro Ser Gln Glu Leu Lys Trp Phe His Arg Tyr Gln Ala Phe
            250                 255                 260 tac gcg ccg ctc atg tgg ccg ttt tta tgg ctc gcc gcg caa gtc ggt        989
Tyr Ala Pro Leu Met Trp Pro Phe Leu Trp Leu Ala Ala Gln Val Gly
        265                 270                 275 gac gcg caa aac att tta atc gat cga gcg tct ccc ggc gtc gag tac       1037
Asp Ala Gln Asn Ile Leu Ile Asp Arg Ala Ser Pro Gly Val Glu Tyr
    280                 285                 290 aag ggc ttg atg aag aac gaa atc gcg ctg tac ctg ctc ggt aaa gtt       1085
Lys Gly Leu Met Lys Asn Glu Ile Ala Leu Tyr Leu Leu Gly Lys Val
295                 300                 305                 310 ctg cac ttc ggc tta ctt ctc ggc gtt ccg gcg tac atc cac ggg ttg       1133
Leu His Phe Gly Leu Leu Leu Gly Val Pro Ala Tyr Ile His Gly Leu
                315                 320                 325 tcc aac gtc atc gtg ccg ttc ctc gcg tac ggc gcg ttt ggc tcg ttc       1181
Ser Asn Val Ile Val Pro Phe Leu Ala Tyr Gly Ala Phe Gly Ser Phe
            330                 335                 340 gtc ctt tgc tgg ttc ttc atc gtc agc cac aac ttg gag gcg ttg acc       1229
Val Leu Cys Trp Phe Phe Ile Val Ser His Asn Leu Glu Ala Leu Thr
        345                 350                 355 ccg atg aac ttg agc aag agc act aag aac gat tgg ggt gcg tgg caa       1277
Pro Met Asn Leu Ser Lys Ser Thr Lys Asn Asp Trp Gly Ala Trp Gln
    360                 365                 370 atc gaa acg tcc gcg tcg tgg ggt aac agc ttc tgg agc ttc ttt tcc       1325
Ile Glu Thr Ser Ala Ser Trp Gly Asn Ser Phe Trp Ser Phe Phe Ser
375                 380                 385                 390 ggt ggt ttg aac ttg caa atc gag cac cac ttg ttt ccg gga tgc gcg       1373
Gly Gly Leu Asn Leu Gln Ile Glu His His Leu Phe Pro Gly Cys Ala
                395                 400                 405 cac aat ctg tac ccg aag atg gtt ccc atc atc aag gat gag tgc aaa       1421
His Asn Leu Tyr Pro Lys Met Val Pro Ile Ile Lys Asp Glu Cys Lys
            410                 415                 420 aag gct ggc ctc gcg tac acc ggc tat ggt ggc tac ttt gga ttg ttg       1469
Lys Ala Gly Leu Ala Tyr Thr Gly Tyr Gly Gly Tyr Phe Gly Leu Leu
        425                 430                 435 ccc atc acg cgc gac atg ttt tcc tat tta cac aag atg ggc cat caa       1517
Pro Ile Thr Arg Asp Met Phe Ser Tyr Leu His Lys Met Gly His Gln
    440                 445                 450 cga ccg aag gcc atg tag aaatccgaac aaaccgttgt acctcttgtt             1565
Arg Pro Lys Ala Met
455 tgatgaatac agtattttatt ttacaacgca actacgcat                           1604
```

<210> SEQ ID NO 8
<211> LENGTH: 459
<212> TYPE: PRT
<213> ORGANISM: Ostreococcus lucimarinus

<400> SEQUENCE: 8

Met Pro Ser Ala Ala Arg Ser Arg Ala Ser Lys Arg Ala Asn Ala Thr
1               5                   10                  15

Thr Asp Val Ala Thr Thr Ala Pro Glu Ala Thr Leu Asp Pro Thr Arg
            20                  25                  30

Ala Tyr Thr Arg Tyr Arg Gly Val Val Tyr Asp Val Thr Glu Phe Gln
        35                  40                  45

His Arg His Pro Gly Gly Ala Gln Leu Leu Ser Leu Cys Val Gly Arg
    50                  55                  60

Asp Ala Thr Ile Leu Ile Glu Ser His His Leu Arg Pro Glu Val Val
65                  70                  75                  80

Arg Lys Tyr Met Lys Thr Leu Pro Val Val Glu Gly Ala Ala Gly Ala
                85                  90                  95

Phe Gly Lys Glu Glu Thr Phe Pro Lys Pro Leu Asp Ser Ala Val Tyr
            100                 105                 110

Arg Ala Ile Gln Arg Arg Val Arg Asp Glu Val Val Glu Pro Met Lys
        115                 120                 125

Ala Lys Ser Gly Arg Glu Ala His Gly Arg Gly Cys Val Val Asp
    130                 135                 140

Ala Gly Val Val Leu Thr Phe Val Ala Ala Met Val Ala Tyr Trp
145                 150                 155                 160

Arg Ala Pro Ser Ala Leu Thr Gly Cys Ala Leu Gly Leu Ala Gly Tyr
                165                 170                 175

Trp Ser Gly Thr Gly Leu Gln His Thr Ala Asn His Gly Gly Leu Ala
            180                 185                 190

Lys Ser Gly Phe Trp Asn Gln Phe Trp Gly Trp Leu Gly Asn Asp Val
        195                 200                 205

Ala Ile Gly Lys Ser Ser Val Glu Trp Arg Tyr His His Met Val Ser
    210                 215                 220

His His Ser Tyr Cys Asn Asp Ala Asp Leu Asp Gln Asp Val Tyr Thr
225                 230                 235                 240

Ala Leu Pro Leu Leu Arg Leu Asp Pro Ser Gln Glu Leu Lys Trp Phe
                245                 250                 255

His Arg Tyr Gln Ala Phe Tyr Ala Pro Leu Met Trp Pro Phe Leu Trp
            260                 265                 270

Leu Ala Ala Gln Val Gly Asp Ala Gln Asn Ile Leu Ile Asp Arg Ala
        275                 280                 285

Ser Pro Gly Val Glu Tyr Lys Gly Leu Met Lys Asn Glu Ile Ala Leu
    290                 295                 300

Tyr Leu Leu Gly Lys Val Leu His Phe Gly Leu Leu Gly Val Pro
305                 310                 315                 320

Ala Tyr Ile His Gly Leu Ser Asn Val Ile Val Pro Phe Leu Ala Tyr
                325                 330                 335

Gly Ala Phe Gly Ser Phe Val Leu Cys Trp Phe Phe Ile Val Ser His
            340                 345                 350

Asn Leu Glu Ala Leu Thr Pro Met Asn Leu Ser Lys Ser Thr Lys Asn
        355                 360                 365

Asp Trp Gly Ala Trp Gln Ile Glu Thr Ser Ala Ser Trp Gly Asn Ser

```
                    370                 375                 380
Phe Trp Ser Phe Phe Ser Gly Gly Leu Asn Leu Gln Ile Glu His His
385                 390                 395                 400

Leu Phe Pro Gly Cys Ala His Asn Leu Tyr Pro Lys Met Val Pro Ile
                405                 410                 415

Ile Lys Asp Glu Cys Lys Lys Ala Gly Leu Ala Tyr Thr Gly Tyr Gly
            420                 425                 430

Gly Tyr Phe Gly Leu Leu Pro Ile Thr Arg Asp Met Phe Ser Tyr Leu
        435                 440                 445

His Lys Met Gly His Gln Arg Pro Lys Ala Met
    450                 455

<210> SEQ ID NO 9
<211> LENGTH: 2297
<212> TYPE: DNA
<213> ORGANISM: Ostreococcus lucimarinus
<220> FEATURE:
<223> OTHER INFORMATION: Delta-5 desaturase
<220> FEATURE:
<221> NAME/KEY: CDS
<222> LOCATION: (629)..(2104)

<400> SEQUENCE: 9
cgcgcgcgcg tcgccgcgac cccccctcgaa gtcgcgtacc gttcgcccgc gtcgctcgcg      60
tcgcgctctc gccgtctcgc gcgcgcgtcg cgtcgcgatg cgtcttcgcg cgtcgtcgcg     120
atcggcgtct tccggcgtcc acgattcgcg cgcgcgcgtc ctcctccgcg gcgctcgcgc     180
gcgcgcgtcg atcgcgtcgc gtcgatcgcg gtctctctcg cggttcctcg cggttcgcgc     240
ctccctcgcg cgcgcgtcga gcgcgcgccg tcgtctgcgg cgccgtcgcc gtttccgcg      300 cgattcgtcc gacacgcgtc cgacacgcgt gcgacacgcg cgtttacata ccacaaatac     360
cacacagtgt acgaccaaca ttaccgtact gtagaagaaa tgatggtcac tcgatgtata     420
cagaccccgt cactgatccc catacgcgac cgaccgcccc gcccggtgac gtcggcgcgc     480
gcgcgcgtcg ccacacgacg ccgcgcgctc gccgcgcgcg ctcgactcgc gcgccgcgtc     540
gcgcgccgtc gcgctcaccg cgcgcccgcg accgccggcg tcgcgcgtcg acgacgccgc     600
gcggcgaacg agggcgcgac gcgacgcg atg acg acg gtc gcg gag atc gtc        652
                                 Met Thr Thr Val Ala Glu Ile Val
                                   1               5 gac gac gac gcg cgg cgc gcg gga aag ggc gcg acg acg cga cga cga        700
Asp Asp Asp Ala Arg Arg Ala Gly Lys Gly Ala Thr Thr Arg Arg Arg
 10                  15                  20 cgc gcg acg acg cgc gtc gcg cgc gat gac gcg cgc gag gcg acg tac        748
Arg Ala Thr Thr Arg Val Ala Arg Asp Asp Ala Arg Glu Ala Thr Tyr
 25                  30                  35                  40 acg gcg gcg gag gtg gcg agg cac gcg cgc gcg gac gac tgc tgg gtg        796
Thr Ala Ala Glu Val Ala Arg His Ala Arg Ala Asp Asp Cys Trp Val
                 45                  50                  55 atc gtg cga ggc ggc gtg tac gac gtg acg agg ttc gtg ccg aga cac        844
Ile Val Arg Gly Gly Val Tyr Asp Val Thr Arg Phe Val Pro Arg His
             60                  65                  70 ccg gga ggg aac atg ata tac gtc aag gcg ggg ggc gag tgc acg gcg        892
Pro Gly Gly Asn Met Ile Tyr Val Lys Ala Gly Gly Glu Cys Thr Ala
         75                  80                  85 ctg ttc gac tcg tat cat ccc gag cgc gcg agg gcg acg ctg gag aag        940
Leu Phe Asp Ser Tyr His Pro Glu Arg Ala Arg Ala Thr Leu Glu Lys
     90                  95                 100 tat agg atc ggc gcg ctg cgg agg gac gcg ggg gaa cgc gag gac gag        988
```

```
Tyr Arg Ile Gly Ala Leu Arg Arg Asp Ala Gly Glu Arg Glu Asp Glu
105                 110                 115                 120 gac gtg gtg gag tac ttg aag gac gat ctg agg gag gga gag ttt tac    1036
Asp Val Val Glu Tyr Leu Lys Asp Asp Leu Arg Glu Gly Glu Phe Tyr
                125                 130                 135 gcg gat tgt aag gcg ggg gcg gcg aag tat ttt aag gat aat aag ctc    1084
Ala Asp Cys Lys Ala Gly Ala Ala Lys Tyr Phe Lys Asp Asn Lys Leu
            140                 145                 150 gat ccg cgc gtg cac tgg gag atg tac gcg aag acg ttg gtg att ttg    1132
Asp Pro Arg Val His Trp Glu Met Tyr Ala Lys Thr Leu Val Ile Leu
        155                 160                 165 acg ggc gtc gtc gtc gga cac tac ggg tcg ttt ttc gcg ccg tcg gcg    1180
Thr Gly Val Val Val Gly His Tyr Gly Ser Phe Phe Ala Pro Ser Ala
    170                 175                 180 tcc ttc gcc gcg gcg ttg gcg ctc gcg gtg ctg cac ggc acg tgc aag    1228
Ser Phe Ala Ala Ala Leu Ala Leu Ala Val Leu His Gly Thr Cys Lys
185                 190                 195                 200 gcg gaa gta gga gtg tcg atc cag cac gac gcc aat cac ggg gcg tac    1276
Ala Glu Val Gly Val Ser Ile Gln His Asp Ala Asn His Gly Ala Tyr
                205                 210                 215 gga aac aat cgc act tgg ttg cac gcg atg cag ttg acc ttg gac gcc    1324
Gly Asn Asn Arg Thr Trp Leu His Ala Met Gln Leu Thr Leu Asp Ala
            220                 225                 230 gtc ggc gcg tcg agc ttc atg tgg aag cag cag cac gtc gcc gga cat    1372
Val Gly Ala Ser Ser Phe Met Trp Lys Gln Gln His Val Ala Gly His
        235                 240                 245 cac gcg tac acc aac gtc gaa ggc atc gat ccc gac att cga tgc tcg    1420
His Ala Tyr Thr Asn Val Glu Gly Ile Asp Pro Asp Ile Arg Cys Ser
    250                 255                 260 gaa aag gac gtg cga cgg gtg aac gag cat cag cct cac gag ccg tac    1468
Glu Lys Asp Val Arg Arg Val Asn Glu His Gln Pro His Glu Pro Tyr
265                 270                 275                 280 cac aga gtt caa cac gtc tac ttg gcg ttg atg tac ggc ttg ttg tcg    1516
His Arg Val Gln His Val Tyr Leu Ala Leu Met Tyr Gly Leu Leu Ser
                285                 290                 295 ttc aaa tcg tgc ttc gtg gac gac ttc aac gcc ttc ttc tcc ggc cga    1564
Phe Lys Ser Cys Phe Val Asp Asp Phe Asn Ala Phe Phe Ser Gly Arg
            300                 305                 310 atc ggt tgg gtg aag gtg atg aag ttt act cgc ggt gaa gcc gtg gcg    1612
Ile Gly Trp Val Lys Val Met Lys Phe Thr Arg Gly Glu Ala Val Ala
        315                 320                 325 ttt tgg gga agc aag ctc gcg tgg gcg ttt tac tac ctc tac ttg ccc    1660
Phe Trp Gly Ser Lys Leu Ala Trp Ala Phe Tyr Tyr Leu Tyr Leu Pro
    330                 335                 340 gcc aag tac tcc cat cgc tcg atc ggt cag ctc ttg gcg ctc tgg acc    1708
Ala Lys Tyr Ser His Arg Ser Ile Gly Gln Leu Leu Ala Leu Trp Thr
345                 350                 355                 360 gtc acc gag ttc gtc acc ggt tgg ttg ctg gcg ttc atg ttc caa gtc    1756
Val Thr Glu Phe Val Thr Gly Trp Leu Leu Ala Phe Met Phe Gln Val
                365                 370                 375 gcc cac gtc gtc ggc gac gtc cac ttc ttc cgc ctc aac gaa aag aac    1804
Ala His Val Val Gly Asp Val His Phe Phe Arg Leu Asn Glu Lys Asn
            380                 385                 390 cag ctc aac aag ggc tgg ggc gag gcg caa ctc atg act tcg gct gat    1852
Gln Leu Asn Lys Gly Trp Gly Glu Ala Gln Leu Met Thr Ser Ala Asp
        395                 400                 405 ttc gcg cac ggc agc aag ttt tgg acc cac ttc tcc ggc ggc tta aac    1900
Phe Ala His Gly Ser Lys Phe Trp Thr His Phe Ser Gly Gly Leu Asn
    410                 415                 420
```

```
tat caa gtc gtc cac cac ctc ttc ccg ggc gtg tgt cac gtg cac tac    1948
Tyr Gln Val Val His His Leu Phe Pro Gly Val Cys His Val His Tyr
425                 430                 435                 440 ccc gcg ctc gcg ccg atc atc aag gct gcc gcg gat aag cac gga tta    1996
Pro Ala Leu Ala Pro Ile Ile Lys Ala Ala Ala Asp Lys His Gly Leu
            445                 450                 455 cac tat caa atc tac ccc acg ttt tgg tcc gcg ctg cgc gcg cac ttc    2044
His Tyr Gln Ile Tyr Pro Thr Phe Trp Ser Ala Leu Arg Ala His Phe
                460                 465                 470 tcc cac ctc gcc cgc gtc ggc cac gag gcg tac gtg cct tcc ctc cga    2092
Ser His Leu Ala Arg Val Gly His Glu Ala Tyr Val Pro Ser Leu Arg
        475                 480                 485 acc gtc ggg tga gcgcgcctcg cgcgcggcca tttattcata cctttacctc        2144
Thr Val Gly
        490 accccgacgc gtcgatcgct cgccggcgct cccatcgcat ttattttaat ctccacgtct  2204 tccgtccatc cctcgcgcct tcgcctcgcg ctcgcgctcg cctcgcctcg cccgggcttc  2264 ctccccactc cgccgcgcgc cgtcgcgcgc gcg                               2297

<210> SEQ ID NO 10
<211> LENGTH: 491
<212> TYPE: PRT
<213> ORGANISM: Ostreococcus lucimarinus

<400> SEQUENCE: 10

Met Thr Thr Val Ala Glu Ile Val Asp Asp Ala Arg Arg Ala Gly
 1               5                  10                  15

Lys Gly Ala Thr Thr Arg Arg Arg Ala Thr Thr Arg Val Ala Arg
                20                  25                  30

Asp Asp Ala Arg Glu Ala Thr Tyr Thr Ala Ala Glu Val Ala Arg His
            35                  40                  45

Ala Arg Ala Asp Asp Cys Trp Val Ile Val Arg Gly Val Tyr Asp
        50                  55                  60

Val Thr Arg Phe Val Pro Arg His Pro Gly Gly Asn Met Ile Tyr Val
 65                  70                  75                  80

Lys Ala Gly Gly Glu Cys Thr Ala Leu Phe Asp Ser Tyr His Pro Glu
                85                  90                  95

Arg Ala Arg Ala Thr Leu Glu Lys Tyr Arg Ile Gly Ala Leu Arg Arg
            100                 105                 110

Asp Ala Gly Glu Arg Glu Asp Glu Val Val Glu Tyr Leu Lys Asp
        115                 120                 125

Asp Leu Arg Glu Gly Glu Phe Tyr Ala Asp Cys Lys Ala Gly Ala Ala
    130                 135                 140

Lys Tyr Phe Lys Asp Asn Lys Leu Asp Pro Arg Val His Trp Glu Met
145                 150                 155                 160

Tyr Ala Lys Thr Leu Val Ile Leu Thr Gly Val Val Gly His Tyr
                165                 170                 175

Gly Ser Phe Phe Ala Pro Ser Ala Ser Phe Ala Ala Ala Leu Ala Leu
            180                 185                 190

Ala Val Leu His Gly Thr Cys Lys Ala Glu Val Gly Val Ser Ile Gln
        195                 200                 205

His Asp Ala Asn His Gly Ala Tyr Gly Asn Asn Arg Thr Trp Leu His
    210                 215                 220

Ala Met Gln Leu Thr Leu Asp Ala Val Gly Ala Ser Ser Phe Met Trp
225                 230                 235                 240
```

| | | | | | | | | | | | | |
|---|---|---|---|---|---|---|---|---|---|---|---|---|
|Lys|Gln|Gln|His|Val|Ala|Gly|His|His|Ala|Tyr|Thr|Asn|Val|Glu|Gly|
| | | | |245| | | | |250| | | | |255| |

Ile Asp Pro Asp Ile Arg Cys Ser Glu Lys Asp Val Arg Val Asn
        260                 265                 270

Glu His Gln Pro His Glu Pro Tyr His Arg Val Gln His Val Tyr Leu
    275                 280                 285

Ala Leu Met Tyr Gly Leu Leu Ser Phe Lys Ser Cys Phe Val Asp Asp
    290                 295                 300

Phe Asn Ala Phe Phe Ser Gly Arg Ile Gly Trp Val Lys Val Met Lys
305                 310                 315                 320

Phe Thr Arg Gly Glu Ala Val Ala Phe Trp Gly Ser Lys Leu Ala Trp
                325                 330                 335

Ala Phe Tyr Tyr Leu Tyr Leu Pro Ala Lys Tyr Ser His Arg Ser Ile
            340                 345                 350

Gly Gln Leu Leu Ala Leu Trp Thr Val Thr Glu Phe Val Thr Gly Trp
        355                 360                 365

Leu Leu Ala Phe Met Phe Gln Val Ala His Val Val Gly Asp Val His
    370                 375                 380

Phe Phe Arg Leu Asn Glu Lys Asn Gln Leu Asn Lys Gly Trp Gly Glu
385                 390                 395                 400

Ala Gln Leu Met Thr Ser Ala Asp Phe Ala His Gly Ser Lys Phe Trp
                405                 410                 415

Thr His Phe Ser Gly Gly Leu Asn Tyr Gln Val Val His His Leu Phe
            420                 425                 430

Pro Gly Val Cys His Val His Tyr Pro Ala Leu Ala Pro Ile Ile Lys
        435                 440                 445

Ala Ala Ala Asp Lys His Gly Leu His Tyr Gln Ile Tyr Pro Thr Phe
    450                 455                 460

Trp Ser Ala Leu Arg Ala His Phe Ser His Leu Ala Arg Val Gly His
465                 470                 475                 480

Glu Ala Tyr Val Pro Ser Leu Arg Thr Val Gly
                485                 490

```
<210> SEQ ID NO 11
<211> LENGTH: 1412
<212> TYPE: DNA
<213> ORGANISM: Ostreococcus lucimarinus
<220> FEATURE:
<223> OTHER INFORMATION: Delta-5 elongase
<220> FEATURE:
<221> NAME/KEY: CDS
<222> LOCATION: (254)..(1150)

<400> SEQUENCE: 11
```

| | |
|---|---|
|cgcgcgcgca cttttttcgcc caccgcgcgc cgtcgcgcac tgcgccgtcg tcgcgcgtcg|60|
|cgcgaacgcc gacatgtcaa acgttacgtt cgccgccgtc tcgcgcgcgt cgctccgtct|120|
|ctctcgcgcg cgtcgtgcgt cgagcgccgc gaaatgtcgc cgagcgtgcg ctatccgttc|180|
|gccaccgcga catcgtcgcc actgacgcgc gcgtcgcccg tcgctcgtcg ctcgcgcgcg|240|
|cgcacgcgga gac atg gcg cag ttt ccg ctc gtt tcg ctg tgt gct ttc|289|
|            Met Ala Gln Phe Pro Leu Val Ser Leu Cys Ala Phe| |
|             1           5            10| |
|gcg gtg tac ggc tac gcg acg tac gcg tac gcg ttc gaa tgg tcg cac|337|
|Ala Val Tyr Gly Tyr Ala Thr Tyr Ala Tyr Ala Phe Glu Trp Ser His| |
|     15             20            25| |
|gcg cgc acg ccc gga ggt ttg gcg aac gtc gac gcg cag cga tgg atc|385|
|Ala Arg Thr Pro Gly Gly Leu Ala Asn Val Asp Ala Gln Arg Trp Ile| |

```
                  30                  35                  40
ggt gat ctc tcg ttc gcg ctc ccg gcg tgc gcg acg acg gcg tac ttg      433
Gly Asp Leu Ser Phe Ala Leu Pro Ala Cys Ala Thr Thr Ala Tyr Leu
 45                  50                  55                  60 atg ttt tgc ctc gtc ggg ccg cgc gtg atg gcg aag cga gag gcg ttc      481
Met Phe Cys Leu Val Gly Pro Arg Val Met Ala Lys Arg Glu Ala Phe
                 65                  70                  75 gat ccg aaa ggg ctc atg ctg gcg tac aac gcg tat cag acg gcg ttc      529
Asp Pro Lys Gly Leu Met Leu Ala Tyr Asn Ala Tyr Gln Thr Ala Phe
             80                  85                  90 aac gtg tgc gtg ctc ggg atg ttt att cgg gag atc gtg acg ctg aaa      577
Asn Val Cys Val Leu Gly Met Phe Ile Arg Glu Ile Val Thr Leu Lys
         95                 100                 105 caa ccg acg tgg ggg tcg aag atg ccg tgg agc gat aaa cgg tcg ttt      625
Gln Pro Thr Trp Gly Ser Lys Met Pro Trp Ser Asp Lys Arg Ser Phe
    110                 115                 120 aac atc ttg ctc ggg gtg tgg ttt cat tac aac aac aag tat ttg gaa      673
Asn Ile Leu Leu Gly Val Trp Phe His Tyr Asn Asn Lys Tyr Leu Glu
125                 130                 135                 140 ttg ctg gac acg gcg ttt atg att gcc cgc aag aag acg aat caa ctg      721
Leu Leu Asp Thr Ala Phe Met Ile Ala Arg Lys Lys Thr Asn Gln Leu
                145                 150                 155 agc ttt ttg cac gtg tat cat cac gca ctg ttg att tgg gca tgg tgg      769
Ser Phe Leu His Val Tyr His His Ala Leu Leu Ile Trp Ala Trp Trp
            160                 165                 170 ttc gtg tgt cat ctg atg gcg acg aac gat tgc gtc gac gcg tac ttt      817
Phe Val Cys His Leu Met Ala Thr Asn Asp Cys Val Asp Ala Tyr Phe
        175                 180                 185 ggt gcg gcg tgt aac tcg ttc att cac atc gtg atg tac tcg tac tat      865
Gly Ala Ala Cys Asn Ser Phe Ile His Ile Val Met Tyr Ser Tyr Tyr
    190                 195                 200 tta atg gcg gcg ctc ggc gtg cga tgc ccc tgg aag cgt tac atc acg      913
Leu Met Ala Ala Leu Gly Val Arg Cys Pro Trp Lys Arg Tyr Ile Thr
205                 210                 215                 220 cag gcg caa atg tta caa ttt gtc atc gtt ttc gtc cac gcc gtg ttc      961
Gln Ala Gln Met Leu Gln Phe Val Ile Val Phe Val His Ala Val Phe
                225                 230                 235 gtc tta cga gaa aag cac tgc cca gtc tca tta cca tgg gcg caa atg     1009
Val Leu Arg Glu Lys His Cys Pro Val Ser Leu Pro Trp Ala Gln Met
            240                 245                 250 ttc gtc atg gcg aac atg ctc gtg tta ttc ggt aac ttc tac ctc aag     1057
Phe Val Met Ala Asn Met Leu Val Leu Phe Gly Asn Phe Tyr Leu Lys
        255                 260                 265 gcg tac gcc gcc aaa ccg tcg ggc aaa tcc tcg acg cgc gtc tcc gcc     1105
Ala Tyr Ala Ala Lys Pro Ser Gly Lys Ser Ser Thr Arg Val Ser Ala
    270                 275                 280 gcc aaa ccg gca acc agg cgc act cga agc cgt aag atc gat tga         1150
Ala Lys Pro Ala Thr Arg Arg Thr Arg Ser Arg Lys Ile Asp
285                 290                 295 tagtcgcgta gtgtggtcgt ttcactagtc ttcgtattgt ttcttcgcaa taatattgga   1210
atattggact tttcctgtac agatcgagcg ctcggccgcg ctgtttcgca acgaagcgcg   1270
cgcgcgccca gcccgaagct tcagcgcgca tcgcgacatc gtcctcacat tcgtacgcgc   1330
gacgttcacg cctcgtcgta aacgcgctcg atcgatcgaa agactttaaa cacgccgaac   1390
gaaggcgcga acgagtccaa cg                                            1412

<210> SEQ ID NO 12
<211> LENGTH: 298
```

```
<212> TYPE: PRT
<213> ORGANISM: Ostreococcus lucimarinus

<400> SEQUENCE: 12

Met Ala Gln Phe Pro Leu Val Ser Leu Cys Ala Phe Ala Val Tyr Gly
 1               5                  10                  15

Tyr Ala Thr Tyr Ala Tyr Ala Phe Glu Trp Ser His Ala Arg Thr Pro
             20                  25                  30

Gly Gly Leu Ala Asn Val Asp Ala Gln Arg Trp Ile Gly Asp Leu Ser
         35                  40                  45

Phe Ala Leu Pro Ala Cys Ala Thr Thr Ala Tyr Leu Met Phe Cys Leu
     50                  55                  60

Val Gly Pro Arg Val Met Ala Lys Arg Glu Ala Phe Asp Pro Lys Gly
 65                  70                  75                  80

Leu Met Leu Ala Tyr Asn Ala Tyr Gln Thr Ala Phe Asn Val Cys Val
                 85                  90                  95

Leu Gly Met Phe Ile Arg Glu Ile Val Thr Leu Lys Gln Pro Thr Trp
            100                 105                 110

Gly Ser Lys Met Pro Trp Ser Asp Lys Arg Ser Phe Asn Ile Leu Leu
        115                 120                 125

Gly Val Trp Phe His Tyr Asn Asn Lys Tyr Leu Glu Leu Leu Asp Thr
    130                 135                 140

Ala Phe Met Ile Ala Arg Lys Lys Thr Asn Gln Leu Ser Phe Leu His
145                 150                 155                 160

Val Tyr His His Ala Leu Leu Ile Trp Ala Trp Trp Phe Val Cys His
                165                 170                 175

Leu Met Ala Thr Asn Asp Cys Val Asp Ala Tyr Phe Gly Ala Ala Cys
            180                 185                 190

Asn Ser Phe Ile His Ile Val Met Tyr Ser Tyr Tyr Leu Met Ala Ala
        195                 200                 205

Leu Gly Val Arg Cys Pro Trp Lys Arg Tyr Ile Thr Gln Ala Gln Met
    210                 215                 220

Leu Gln Phe Val Ile Val Phe Val His Ala Val Phe Val Leu Arg Glu
225                 230                 235                 240

Lys His Cys Pro Val Ser Leu Pro Trp Ala Gln Met Phe Val Met Ala
                245                 250                 255

Asn Met Leu Val Leu Phe Gly Asn Phe Tyr Leu Lys Ala Tyr Ala Ala
            260                 265                 270

Lys Pro Ser Gly Lys Ser Ser Thr Arg Val Ser Ala Ala Lys Pro Ala
        275                 280                 285

Thr Arg Arg Thr Arg Ser Arg Lys Ile Asp
    290                 295

<210> SEQ ID NO 13
<211> LENGTH: 2077
<212> TYPE: DNA
<213> ORGANISM: Ostreococcus lucimarinus
<220> FEATURE:
<223> OTHER INFORMATION: Delta-6 desaturase
<220> FEATURE:
<221> NAME/KEY: CDS
<222> LOCATION: (388)..(1836)

<400> SEQUENCE: 13
cgccgcgcgg cgacgttcaa cgtagcgaat tgaaacgaat tagcatgtgc gaataacgcg    60
agagacgatg attcgatcgc gacgaccacc gcgtcgaccg cgcgcgcggt cgcgcgaggc   120
```

```
                                                            -continued gacattaaaa cgcgcgcgct cggcgctcgc gcgcgacgca gggagcacaa gatgatgaca        180
ctggcggctc gctttatcgt cacatcgcgt cgtcgcgcgc gcgcggcggc gtccgtgacc        240
gcgcgcaccg cgaaacaaac acgcgcgatc aaagtttcgc gcgcgccgca cgcctcgaag        300
acgcgcggcg acgacgtcag acgcgttcaa agcgacgaat tccacaaaac tgatcgttcg        360
ctttaaatcc tgattaaaac gcgagag atg tgc gtc gaa acg acc gaa ggc aca        414
                                Met Cys Val Glu Thr Thr Glu Gly Thr
                                  1               5 tcg cga acg atg gcg aac gaa cgc acg agc tcg tcg tcg ctg agc              462
Ser Arg Thr Met Ala Asn Glu Arg Thr Ser Ser Ser Ser Leu Ser
 10              15                  20                  25 gaa ggc gga acg ccg acg gtg acg gtc ggg atg gga agc gaa gac gcg          510
Glu Gly Gly Thr Pro Thr Val Thr Val Gly Met Gly Ser Glu Asp Ala
                 30                  35                  40 ggg aag aag act cga aac gcg agc gtc acg gcg tgg acg aaa gag ttg          558
Gly Lys Lys Thr Arg Asn Ala Ser Val Thr Ala Trp Thr Lys Glu Leu
                     45                  50                  55 gag ccg cac gcg atc gcg aag acg ttc gaa cgg cgg tac gtg acg atc          606
Glu Pro His Ala Ile Ala Lys Thr Phe Glu Arg Arg Tyr Val Thr Ile
             60                  65                  70 gaa ggc gtg gaa tac gat gtg acg gat ttt aag cat ccc gga gga tcg          654
Glu Gly Val Glu Tyr Asp Val Thr Asp Phe Lys His Pro Gly Gly Ser
 75                  80                  85 gtt att tat tac atg ctg tcg aac acg gga gcg gac gcg acg gag gct          702
Val Ile Tyr Tyr Met Leu Ser Asn Thr Gly Ala Asp Ala Thr Glu Ala
 90                  95                 100                 105 ttt aaa gag ttt cat tat cgg tcg aaa aag gcg cgc aag gcg ttg gcg          750
Phe Lys Glu Phe His Tyr Arg Ser Lys Lys Ala Arg Lys Ala Leu Ala
                110                 115                 120 gcg ttg ccg cat aag cca gtg gac gcg gcg acg cgg gaa ccg atc gaa          798
Ala Leu Pro His Lys Pro Val Asp Ala Ala Thr Arg Glu Pro Ile Glu
                    125                 130                 135 gat gag gcg atg ctg aag gat ttc gcg cag tgg cgc aag gaa ttg gag          846
Asp Glu Ala Met Leu Lys Asp Phe Ala Gln Trp Arg Lys Glu Leu Glu
            140                 145                 150 cgt gag gga ttt ttt aag ccc tcg ccg gcg cac gtg gcg tat cga ttc          894
Arg Glu Gly Phe Phe Lys Pro Ser Pro Ala His Val Ala Tyr Arg Phe
155                 160                 165 gcc gag ctc gcg gcg atg ttc gcg ctc ggc acg gcg ttg atg cac gcg          942
Ala Glu Leu Ala Ala Met Phe Ala Leu Gly Thr Ala Leu Met His Ala
170                 175                 180                 185 cgt tgg cac gtc gct tcc gtg atc gtg tac tcg tgt ttc ttc ggc gcg          990
Arg Trp His Val Ala Ser Val Ile Val Tyr Ser Cys Phe Phe Gly Ala
                    190                 195                 200 cga tgc ggt tgg gtg cag cac gag ggt ggg cac aat tcg ttg act gga         1038
Arg Cys Gly Trp Val Gln His Glu Gly Gly His Asn Ser Leu Thr Gly
                205                 210                 215 aac att tgg tgg gac aag cga atc caa gcc ttc gcc gcg ggg ttc ggc         1086
Asn Ile Trp Trp Asp Lys Arg Ile Gln Ala Phe Ala Ala Gly Phe Gly
            220                 225                 230 ttg gcg tcg agt ggc gac atg tgg aac aac atg cac aac aag cat cac         1134
Leu Ala Ser Ser Gly Asp Met Trp Asn Asn Met His Asn Lys His His
        235                 240                 245 gcg acg ccc caa aag gtg cga cac gat atg gat ctc gac acc act ccc         1182
Ala Thr Pro Gln Lys Val Arg His Asp Met Asp Leu Asp Thr Thr Pro
250                 255                 260                 265 acg gtg gcg ttc ttc aac tcc gcg gtt gaa gaa aat cgc ccg cgg gga         1230
Thr Val Ala Phe Phe Asn Ser Ala Val Glu Glu Asn Arg Pro Arg Gly
                    270                 275                 280
```

```
ttc agt aag ttg tgg ttg cgc ctt caa gcg tgg acc ttc gtg ccc gtg    1278
Phe Ser Lys Leu Trp Leu Arg Leu Gln Ala Trp Thr Phe Val Pro Val
            285                 290                 295 acg tcc ggt atg gtt ttg ttc ttc tgg atg ttc gtc ttg cac ccg cgt    1326
Thr Ser Gly Met Val Leu Phe Phe Trp Met Phe Val Leu His Pro Arg
        300                 305                 310 aac gcg ctg cga cgc aaa agc ttc gaa gaa gcg gct tgg atg ttt tcc    1374
Asn Ala Leu Arg Arg Lys Ser Phe Glu Glu Ala Ala Trp Met Phe Ser
        315                 320                 325 gcg cac gtc att cgc acg gcg gtt atc aaa gcc gtc acc ggc tac tcc    1422
Ala His Val Ile Arg Thr Ala Val Ile Lys Ala Val Thr Gly Tyr Ser
330                 335                 340                 345 tgg atc gcc tcg tac ggc ttg ttc gcg gcg acg atg tgg gcg agc gga    1470
Trp Ile Ala Ser Tyr Gly Leu Phe Ala Ala Thr Met Trp Ala Ser Gly
                350                 355                 360 tgt tac ttg ttc gcg cac ttt tcc acg tct cac acg cac ttg gat gtc    1518
Cys Tyr Leu Phe Ala His Phe Ser Thr Ser His Thr His Leu Asp Val
            365                 370                 375 gtg ccg agc gat aaa cac ctc tcg tgg gtg cga tac gcc gtc gat cac    1566
Val Pro Ser Asp Lys His Leu Ser Trp Val Arg Tyr Ala Val Asp His
        380                 385                 390 acg atc gac atc aat ccg aac aac agc gtc gtc aac tgg ttg atg ggc    1614
Thr Ile Asp Ile Asn Pro Asn Asn Ser Val Val Asn Trp Leu Met Gly
        395                 400                 405 tac ttg aac tgc caa gtc atc cat cac ctg ttc ccg gat atg cct cag    1662
Tyr Leu Asn Cys Gln Val Ile His His Leu Phe Pro Asp Met Pro Gln
410                 415                 420                 425 ttc cgc caa ccc gaa gtc tcc cgc cga ttc gtc ccg ttt gcg aag aag    1710
Phe Arg Gln Pro Glu Val Ser Arg Arg Phe Val Pro Phe Ala Lys Lys
                430                 435                 440 tgg aac tta aac tac aag gtc ttg acg tat tat ggg gcc tgg aag gcg    1758
Trp Asn Leu Asn Tyr Lys Val Leu Thr Tyr Tyr Gly Ala Trp Lys Ala
            445                 450                 455 acg ttc ggc aac ttg aac gac gtc ggg aag cac tat tac gtg cac gga    1806
Thr Phe Gly Asn Leu Asn Asp Val Gly Lys His Tyr Tyr Val His Gly
        460                 465                 470 tct cag cgc gtc aaa tca aag tcg gcg tga gtttcgatga gctcttcgcc      1856
Ser Gln Arg Val Lys Ser Lys Ser Ala
        475                 480 ctcgcgatgt cgcctcgcgc gacgttctct catcttatcc catcttgcat catctcgcgc  1916
ggcacttcac tagctcgccc gcgttatct ccaagattta ccgctttgtg aacgtttatt   1976
ctagcaacct ttagggtttt tttcgcgaac gagacgtcaa cttgtctgcc gcccatcgca  2036
acgttccgcc acaccacggc tcgccgacgc ccgctcgcgc g                      2077

<210> SEQ ID NO 14
<211> LENGTH: 482
<212> TYPE: PRT
<213> ORGANISM: Ostreococcus lucimarinus

<400> SEQUENCE: 14

Met Cys Val Glu Thr Thr Glu Gly Thr Ser Arg Thr Met Ala Asn Glu
1               5                   10                  15

Arg Thr Ser Ser Ser Ser Leu Ser Glu Gly Gly Thr Pro Thr Val
            20                  25                  30

Thr Val Gly Met Gly Ser Glu Asp Ala Gly Lys Lys Thr Arg Asn Ala
        35                  40                  45

Ser Val Thr Ala Trp Thr Lys Glu Leu Glu Pro His Ala Ile Ala Lys
```

```
                50                  55                  60
Thr Phe Glu Arg Arg Tyr Val Thr Ile Glu Gly Val Glu Tyr Asp Val
 65                      70                  75                  80

Thr Asp Phe Lys His Pro Gly Gly Ser Val Ile Tyr Met Leu Ser
                     85                  90                  95

Asn Thr Gly Ala Asp Ala Thr Glu Ala Phe Lys Glu Phe His Tyr Arg
                100                 105                 110

Ser Lys Lys Ala Arg Lys Ala Leu Ala Ala Leu Pro His Lys Pro Val
                115                 120                 125

Asp Ala Ala Thr Arg Glu Pro Ile Glu Asp Glu Ala Met Leu Lys Asp
            130                 135                 140

Phe Ala Gln Trp Arg Lys Glu Leu Glu Arg Glu Gly Phe Phe Lys Pro
145                 150                 155                 160

Ser Pro Ala His Val Ala Tyr Arg Phe Ala Glu Leu Ala Ala Met Phe
                    165                 170                 175

Ala Leu Gly Thr Ala Leu Met His Ala Arg Trp His Val Ala Ser Val
                180                 185                 190

Ile Val Tyr Ser Cys Phe Phe Gly Ala Arg Cys Gly Trp Val Gln His
            195                 200                 205

Glu Gly Gly His Asn Ser Leu Thr Gly Asn Ile Trp Trp Asp Lys Arg
            210                 215                 220

Ile Gln Ala Phe Ala Ala Gly Phe Gly Leu Ala Ser Ser Gly Asp Met
225                 230                 235                 240

Trp Asn Asn Met His Asn Lys His His Ala Thr Pro Gln Lys Val Arg
                    245                 250                 255

His Asp Met Asp Leu Asp Thr Thr Pro Thr Val Ala Phe Phe Asn Ser
                260                 265                 270

Ala Val Glu Glu Asn Arg Pro Arg Gly Phe Ser Lys Leu Trp Leu Arg
                275                 280                 285

Leu Gln Ala Trp Thr Phe Val Pro Val Thr Ser Gly Met Val Leu Phe
            290                 295                 300

Phe Trp Met Phe Val Leu His Pro Arg Asn Ala Leu Arg Arg Lys Ser
305                 310                 315                 320

Phe Glu Glu Ala Ala Trp Met Phe Ser Ala His Val Ile Arg Thr Ala
                    325                 330                 335

Val Ile Lys Ala Val Thr Gly Tyr Ser Trp Ile Ala Ser Tyr Gly Leu
                340                 345                 350

Phe Ala Ala Thr Met Trp Ala Ser Gly Cys Tyr Leu Phe Ala His Phe
                355                 360                 365

Ser Thr Ser His Thr His Leu Asp Val Val Pro Ser Asp Lys His Leu
            370                 375                 380

Ser Trp Val Arg Tyr Ala Val Asp His Thr Ile Asp Ile Asn Pro Asn
385                 390                 395                 400

Asn Ser Val Val Asn Trp Leu Met Gly Tyr Leu Asn Cys Gln Val Ile
                    405                 410                 415

His His Leu Phe Pro Asp Met Pro Gln Phe Arg Gln Pro Glu Val Ser
                420                 425                 430

Arg Arg Phe Val Pro Phe Ala Lys Lys Trp Asn Leu Asn Tyr Lys Val
                435                 440                 445

Leu Thr Tyr Tyr Gly Ala Trp Lys Ala Thr Phe Gly Asn Leu Asn Asp
            450                 455                 460

Val Gly Lys His Tyr Tyr Val His Gly Ser Gln Arg Val Lys Ser Lys
465                 470                 475                 480
```

Ser Ala

<210> SEQ ID NO 15
<211> LENGTH: 864
<212> TYPE: DNA
<213> ORGANISM: Ostreococcus lucimarinus
<220> FEATURE:
<223> OTHER INFORMATION: Delta-6 elongase
<220> FEATURE:
<221> NAME/KEY: CDS
<222> LOCATION: (1)..(864)

<400> SEQUENCE: 15

```
atg ttg cga cac tac tgg aag gcg tgg gac tca atc att tcg aaa gta      48
Met Leu Arg His Tyr Trp Lys Ala Trp Asp Ser Ile Ile Ser Lys Val
  1               5                  10                  15 gtt ttc tcc tgc gct gac tgg tta ggc tgg gag ctc gac ccg ctg agc      96
Val Phe Ser Cys Ala Asp Trp Leu Gly Trp Glu Leu Asp Pro Leu Ser
             20                  25                  30 ccc acc acc tca cat tta ccc gcc ata acc tca cca act cct ctg atc     144
Pro Thr Thr Ser His Leu Pro Ala Ile Thr Ser Pro Thr Pro Leu Ile
         35                  40                  45 acc agc ctt ctc gtg tac ttg gtc acg gtc gtt gta tcg tac cgc gtc     192
Thr Ser Leu Leu Val Tyr Leu Val Thr Val Val Val Ser Tyr Arg Val
     50                  55                  60 tta tcc gca aca aca aac aca aag att tgg gat ccc aca tgg tta aaa     240
Leu Ser Ala Thr Thr Asn Thr Lys Ile Trp Asp Pro Thr Trp Leu Lys
 65                  70                  75                  80 gca tcg gtg att tgc cac aat gca ttc ctc ata tta cta agt ttg tat     288
Ala Ser Val Ile Cys His Asn Ala Phe Leu Ile Leu Leu Ser Leu Tyr
                 85                  90                  95 atg tgc atc ggt tgt atc gtc gaa gca tac aaa agt gga tat aag cta     336
Met Cys Ile Gly Cys Ile Val Glu Ala Tyr Lys Ser Gly Tyr Lys Leu
            100                 105                 110 tgg gga aat aag ttc aac gtg aat gaa aag cag ctt gcg ttt tac atc     384
Trp Gly Asn Lys Phe Asn Val Asn Glu Lys Gln Leu Ala Phe Tyr Ile
        115                 120                 125 tac ctc ttt tac gtg agc aag ata tat gag ttc gtt gat aca ttc ata     432
Tyr Leu Phe Tyr Val Ser Lys Ile Tyr Glu Phe Val Asp Thr Phe Ile
    130                 135                 140 atg cta ctg aag aga aac tta cgc caa gta agc ttt ttg cat gtc tac     480
Met Leu Leu Lys Arg Asn Leu Arg Gln Val Ser Phe Leu His Val Tyr
145                 150                 155                 160 cat cac agc act att tcg ttt ata tgg tgg atg atc gca cgt cga gct     528
His His Ser Thr Ile Ser Phe Ile Trp Trp Met Ile Ala Arg Arg Ala
                165                 170                 175 ccg ggt ggg gat gct tac ttc agt gca gca ctg aac tct tgg gta cac     576
Pro Gly Gly Asp Ala Tyr Phe Ser Ala Ala Leu Asn Ser Trp Val His
            180                 185                 190 gtg tgc atg tac acg tac tat ctg cta tcg gct ctg atc ggg aaa aac     624
Val Cys Met Tyr Thr Tyr Tyr Leu Leu Ser Ala Leu Ile Gly Lys Asn
        195                 200                 205 aac gac aaa cgt gtt aag tac ctt tgg tgg ggt cga cat ttg acg cag     672
Asn Asp Lys Arg Val Lys Tyr Leu Trp Trp Gly Arg His Leu Thr Gln
    210                 215                 220 atg cag atg ctt caa ttt cta tgc aat ctg tta cag gcc gtg tac tgt     720
Met Gln Met Leu Gln Phe Leu Cys Asn Leu Leu Gln Ala Val Tyr Cys
225                 230                 235                 240 gca tat ttt tca gaa tac ccg aag ttc ttg tca aag ata ctc ctt ttt     768
Ala Tyr Phe Ser Glu Tyr Pro Lys Phe Leu Ser Lys Ile Leu Leu Phe
                245                 250                 255
```

```
tac atg att agc ctg ctg gcg ctg ttt gga cat ttc tat tac tcc aag    816
Tyr Met Ile Ser Leu Leu Ala Leu Phe Gly His Phe Tyr Tyr Ser Lys
        260                 265                 270 cac atc gcc acc gcg aag ctc agg aaa aaa cac acc aag aag gcg tga    864
His Ile Ala Thr Ala Lys Leu Arg Lys Lys His Thr Lys Lys Ala
        275                 280                 285
```

<210> SEQ ID NO 16
<211> LENGTH: 287
<212> TYPE: PRT
<213> ORGANISM: Ostreococcus lucimarinus

<400> SEQUENCE: 16

```
Met Leu Arg His Tyr Trp Lys Ala Trp Asp Ser Ile Ile Ser Lys Val
 1               5                  10                  15

Val Phe Ser Cys Ala Asp Trp Leu Gly Trp Glu Leu Asp Pro Leu Ser
                20                  25                  30

Pro Thr Thr Ser His Leu Pro Ala Ile Thr Ser Pro Thr Pro Leu Ile
            35                  40                  45

Thr Ser Leu Leu Val Tyr Leu Val Thr Val Val Ser Tyr Arg Val
        50                  55                  60

Leu Ser Ala Thr Thr Asn Thr Lys Ile Trp Asp Pro Thr Trp Leu Lys
 65                  70                  75                  80

Ala Ser Val Ile Cys His Asn Ala Phe Leu Ile Leu Ser Leu Tyr
                85                  90                  95

Met Cys Ile Gly Cys Ile Val Glu Ala Tyr Lys Ser Gly Tyr Lys Leu
            100                 105                 110

Trp Gly Asn Lys Phe Asn Val Asn Glu Lys Gln Leu Ala Phe Tyr Ile
        115                 120                 125

Tyr Leu Phe Tyr Val Ser Lys Ile Tyr Glu Phe Val Asp Thr Phe Ile
    130                 135                 140

Met Leu Leu Lys Arg Asn Leu Arg Gln Val Ser Phe Leu His Val Tyr
145                 150                 155                 160

His His Ser Thr Ile Ser Phe Ile Trp Trp Met Ile Ala Arg Arg Ala
                165                 170                 175

Pro Gly Gly Asp Ala Tyr Phe Ser Ala Ala Leu Asn Ser Trp Val His
            180                 185                 190

Val Cys Met Tyr Thr Tyr Tyr Leu Leu Ser Ala Leu Ile Gly Lys Asn
        195                 200                 205

Asn Asp Lys Arg Val Lys Tyr Leu Trp Trp Gly Arg His Leu Thr Gln
    210                 215                 220

Met Gln Met Leu Gln Phe Leu Cys Asn Leu Leu Gln Ala Val Tyr Cys
225                 230                 235                 240

Ala Tyr Phe Ser Glu Tyr Pro Lys Phe Leu Ser Lys Ile Leu Leu Phe
                245                 250                 255

Tyr Met Ile Ser Leu Leu Ala Leu Phe Gly His Phe Tyr Tyr Ser Lys
            260                 265                 270

His Ile Ala Thr Ala Lys Leu Arg Lys Lys His Thr Lys Lys Ala
        275                 280                 285
```

<210> SEQ ID NO 17
<211> LENGTH: 903
<212> TYPE: DNA
<213> ORGANISM: Ostreococcus tauri
<220> FEATURE:
<221> NAME/KEY: CDS
<222> LOCATION: (1)..(903)

<223> OTHER INFORMATION: Delta-5-Elongase

<400> SEQUENCE: 17

```
atg agc gcc tcc ggt gcg ctg ctg ccc gcg atc gcg ttc gcc gcg tac        48
Met Ser Ala Ser Gly Ala Leu Leu Pro Ala Ile Ala Phe Ala Ala Tyr
1               5                   10                  15 gcg tac gcg acg tac gcc tac gcc ttt gag tgg tcg cac gcg aat ggc        96
Ala Tyr Ala Thr Tyr Ala Tyr Ala Phe Glu Trp Ser His Ala Asn Gly
            20                  25                  30 atc gac aac gtc gac gcg cgc gag tgg atc ggt gcg ctg tcg ttg agg       144
Ile Asp Asn Val Asp Ala Arg Glu Trp Ile Gly Ala Leu Ser Leu Arg
        35                  40                  45 ctc ccg gcg atc gcg acg acg atg tac ctg ttg ttc tgc ctg gtc gga       192
Leu Pro Ala Ile Ala Thr Thr Met Tyr Leu Leu Phe Cys Leu Val Gly
    50                  55                  60 ccg agg ttg atg gcg aag cgc gag gcg ttc gac ccg aag ggg ttc atg       240
Pro Arg Leu Met Ala Lys Arg Glu Ala Phe Asp Pro Lys Gly Phe Met
65                  70                  75                  80 ctg gcg tac aat gcg tat cag acg gcg ttc aac gtc gtc gtc ctc ggg       288
Leu Ala Tyr Asn Ala Tyr Gln Thr Ala Phe Asn Val Val Val Leu Gly
                85                  90                  95 atg ttc gcg cga gag atc tcg ggg ctg ggg cag ccc gtg tgg ggg tca       336
Met Phe Ala Arg Glu Ile Ser Gly Leu Gly Gln Pro Val Trp Gly Ser
            100                 105                 110 acc atg ccg tgg agc gat aga aaa tcg ttt aag atc ctc ctc ggg gtg       384
Thr Met Pro Trp Ser Asp Arg Lys Ser Phe Lys Ile Leu Leu Gly Val
        115                 120                 125 tgg ttg cac tac aac aac caa tat ttg gag cta ttg gac act gtg ttc       432
Trp Leu His Tyr Asn Asn Gln Tyr Leu Glu Leu Leu Asp Thr Val Phe
    130                 135                 140 atg gtt gcg cgc aag aag acg aag cag ttg agc ttc ttg cac gtt tat       480
Met Val Ala Arg Lys Lys Thr Lys Gln Leu Ser Phe Leu His Val Tyr
145                 150                 155                 160 cat cac gcc ctg ttg atc tgg gcg tgg tgg ttg gtg tgt cac ttg atg       528
His His Ala Leu Leu Ile Trp Ala Trp Trp Leu Val Cys His Leu Met
                165                 170                 175 gcc acg aac gat tgt atc gat gcc tac ttc ggc gcg gcg tgc aac tcg       576
Ala Thr Asn Asp Cys Ile Asp Ala Tyr Phe Gly Ala Ala Cys Asn Ser
            180                 185                 190 ttc att cac atc gtg atg tac tcg tat tat ctc atg tcg gcg ctc ggc       624
Phe Ile His Ile Val Met Tyr Ser Tyr Tyr Leu Met Ser Ala Leu Gly
        195                 200                 205 att cga tgc ccg tgg aag cga tac atc acc cag gct caa atg ctc caa       672
Ile Arg Cys Pro Trp Lys Arg Tyr Ile Thr Gln Ala Gln Met Leu Gln
    210                 215                 220 ttc gtc att gtc ttc gcg cac gcc gtg ttc gtg ctg cgt cag aag cac       720
Phe Val Ile Val Phe Ala His Ala Val Phe Val Leu Arg Gln Lys His
225                 230                 235                 240 tgc ccg gtc acc ctt cct tgg gcg caa atg ttc gtc atg acg aac atg       768
Cys Pro Val Thr Leu Pro Trp Ala Gln Met Phe Val Met Thr Asn Met
                245                 250                 255 ctc gtg ctc ttc ggg aac ttc tac ctc aag gcg tac tcg aac aag tcg       816
Leu Val Leu Phe Gly Asn Phe Tyr Leu Lys Ala Tyr Ser Asn Lys Ser
            260                 265                 270 cgc ggc gac ggc gcg agt tcc gtg aaa cca gcc gag acc acg cgc gcg       864
Arg Gly Asp Gly Ala Ser Ser Val Lys Pro Ala Glu Thr Thr Arg Ala
        275                 280                 285 ccc agc gtg cga cgc acg cga tct cga aaa att gac taa                   903
Pro Ser Val Arg Arg Thr Arg Ser Arg Lys Ile Asp
    290                 295                 300
```

<210> SEQ ID NO 18
<211> LENGTH: 300
<212> TYPE: PRT
<213> ORGANISM: Ostreococcus tauri

<400> SEQUENCE: 18

```
Met Ser Ala Ser Gly Ala Leu Leu Pro Ala Ile Ala Phe Ala Ala Tyr
  1               5                  10                  15

Ala Tyr Ala Thr Tyr Ala Tyr Ala Phe Glu Trp Ser His Ala Asn Gly
             20                  25                  30

Ile Asp Asn Val Asp Ala Arg Glu Trp Ile Gly Ala Leu Ser Leu Arg
         35                  40                  45

Leu Pro Ala Ile Ala Thr Thr Met Tyr Leu Leu Phe Cys Leu Val Gly
     50                  55                  60

Pro Arg Leu Met Ala Lys Arg Glu Ala Phe Asp Pro Lys Gly Phe Met
 65                  70                  75                  80

Leu Ala Tyr Asn Ala Tyr Gln Thr Ala Phe Asn Val Val Val Leu Gly
                 85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Gln Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
        275                 280                 285

Pro Ser Val Arg Arg Thr Arg Ser Arg Lys Ile Asp
    290                 295                 300
```

<210> SEQ ID NO 19
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: Delta-6-Elongase

<400> SEQUENCE: 19

```
atg agt ggc tta cgt gca ccc aac ttt tta cac aga ttc tgg aca aag      48
```

```
Met Ser Gly Leu Arg Ala Pro Asn Phe Leu His Arg Phe Trp Thr Lys
 1               5                  10                  15 tgg gac tac gcg att tcc aaa gtc gtc ttc acg tgt gcc gac agt ttt        96
Trp Asp Tyr Ala Ile Ser Lys Val Val Phe Thr Cys Ala Asp Ser Phe
             20                  25                  30 cag tgg gac atc ggg cca gtg agt tcg agt acg gcg cat tta ccc gcc       144
Gln Trp Asp Ile Gly Pro Val Ser Ser Ser Thr Ala His Leu Pro Ala
         35                  40                  45 att gaa tcc cct acc cca ctg gtg act agc ctc ttg ttc tac tta gtc       192
Ile Glu Ser Pro Thr Pro Leu Val Thr Ser Leu Leu Phe Tyr Leu Val
     50                  55                  60 aca gtt ttc ttg tgg tat ggt cgt tta acc agg agt tca gac aag aaa       240
Thr Val Phe Leu Trp Tyr Gly Arg Leu Thr Arg Ser Ser Asp Lys Lys
 65                  70                  75                  80 att aga gag cct acg tgg tta aga aga ttc ata ata tgt cat aat gcg       288
Ile Arg Glu Pro Thr Trp Leu Arg Arg Phe Ile Ile Cys His Asn Ala
                 85                  90                  95 ttc ttg ata gtc ctc agt ctt tac atg tgc ctt ggt tgt gtg gcc caa       336
Phe Leu Ile Val Leu Ser Leu Tyr Met Cys Leu Gly Cys Val Ala Gln
             100                 105                 110 gcg tat cag aat gga tat act tta tgg ggt aat gaa ttc aag gcc acg       384
Ala Tyr Gln Asn Gly Tyr Thr Leu Trp Gly Asn Glu Phe Lys Ala Thr
         115                 120                 125 gaa act cag ctt gct ctc tac att tac att ttt tac gta agt aaa ata       432
Glu Thr Gln Leu Ala Leu Tyr Ile Tyr Ile Phe Tyr Val Ser Lys Ile
     130                 135                 140 tac gag ttt gta gat act tac att atg ctt ctc aag aat aac ttg cgg       480
Tyr Glu Phe Val Asp Thr Tyr Ile Met Leu Leu Lys Asn Asn Leu Arg
145                 150                 155                 160 caa gta agt ttc cta cac att tat cac cac agc acg att tcc ttt att       528
Gln Val Ser Phe Leu His Ile Tyr His His Ser Thr Ile Ser Phe Ile
                 165                 170                 175 tgg tgg atc att gct cgg agg gct ccg ggt ggt gat gct tac ttc agc       576
Trp Trp Ile Ile Ala Arg Arg Ala Pro Gly Gly Asp Ala Tyr Phe Ser
             180                 185                 190 gcg gcc ttg aac tca tgg gta cac gtg tgc atg tac acc tat tat cta       624
Ala Ala Leu Asn Ser Trp Val His Val Cys Met Tyr Thr Tyr Tyr Leu
         195                 200                 205 tta tca acc ctt att gga aaa gaa gat cct aag cgt tcc aac tac ctt       672
Leu Ser Thr Leu Ile Gly Lys Glu Asp Pro Lys Arg Ser Asn Tyr Leu
     210                 215                 220 tgg tgg ggt cgc cac cta acg caa atg cag atg ctt cag ttt ttc ttc       720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag       768
Asn Val Leu Gln Ala Leu Tyr Cys Ala Ser Phe Ser Thr Tyr Pro Lys
                 245                 250                 255 ttt ttg tcc aaa att ctg ctc gtc tat atg atg agc ctt ctc ggc ttg       816
Phe Leu Ser Lys Ile Leu Leu Val Tyr Met Met Ser Leu Leu Gly Leu
             260                 265                 270 ttt ggg cat ttc tac tat tcc aag cac ata gca gca gct aag ctc cag       864
Phe Gly His Phe Tyr Tyr Ser Lys His Ile Ala Ala Ala Lys Leu Gln
         275                 280                 285 aaa aaa cag cag tga                                                   879
Lys Lys Gln Gln
     290
```

<210> SEQ ID NO 20
<211> LENGTH: 292
<212> TYPE: PRT

<213> ORGANISM: Ostreococcus tauri

<400> SEQUENCE: 20

```
Met Ser Gly Leu Arg Ala Pro Asn Phe Leu His Arg Phe Trp Thr Lys
 1               5                  10                  15
Trp Asp Tyr Ala Ile Ser Lys Val Val Phe Thr Cys Ala Asp Ser Phe
            20                  25                  30
Gln Trp Asp Ile Gly Pro Val Ser Ser Thr Ala His Leu Pro Ala
        35                  40                  45
Ile Glu Ser Pro Thr Pro Leu Val Thr Ser Leu Leu Phe Tyr Leu Val
    50                  55                  60
Thr Val Phe Leu Trp Tyr Gly Arg Leu Thr Arg Ser Ser Asp Lys Lys
65                  70                  75                  80
Ile Arg Glu Pro Thr Trp Leu Arg Arg Phe Ile Ile Cys His Asn Ala
                85                  90                  95
Phe Leu Ile Val Leu Ser Leu Tyr Met Cys Leu Gly Cys Val Ala Gln
            100                 105                 110
Ala Tyr Gln Asn Gly Tyr Thr Leu Trp Gly Asn Glu Phe Lys Ala Thr
        115                 120                 125
Glu Thr Gln Leu Ala Leu Tyr Ile Tyr Ile Phe Tyr Val Ser Lys Ile
    130                 135                 140
Tyr Glu Phe Val Asp Thr Tyr Ile Met Leu Leu Lys Asn Asn Leu Arg
145                 150                 155                 160
Gln Val Ser Phe Leu His Ile Tyr His His Ser Thr Ile Ser Phe Ile
                165                 170                 175
Trp Trp Ile Ile Ala Arg Arg Ala Pro Gly Gly Asp Ala Tyr Phe Ser
            180                 185                 190
Ala Ala Leu Asn Ser Trp Val His Val Cys Met Tyr Thr Tyr Tyr Leu
        195                 200                 205
Leu Ser Thr Leu Ile Gly Lys Glu Asp Pro Lys Arg Ser Asn Tyr Leu
    210                 215                 220
Trp Trp Gly Arg His Leu Thr Gln Met Gln Met Leu Gln Phe Phe Phe
225                 230                 235                 240
Asn Val Leu Gln Ala Leu Tyr Cys Ala Ser Phe Ser Tyr Pro Lys
                245                 250                 255
Phe Leu Ser Lys Ile Leu Leu Val Tyr Met Met Ser Leu Leu Gly Leu
            260                 265                 270
Phe Gly His Phe Tyr Tyr Ser Lys His Ile Ala Ala Ala Lys Leu Gln
        275                 280                 285
Lys Lys Gln Gln
    290
```

<210> SEQ ID NO 21
<211> LENGTH: 879
<212> TYPE: DNA
<213> ORGANISM: Ostreococcus tauri
<220> FEATURE:
<221> NAME/KEY: CDS
<222> LOCATION: (1)..(879)
<223> OTHER INFORMATION: Delta-6-Elongase

<400> SEQUENCE: 21

```
atg agt ggc tta cgt gca ccc aac ttt tta cac aga ttc tgg aca aag      48
Met Ser Gly Leu Arg Ala Pro Asn Phe Leu His Arg Phe Trp Thr Lys
 1               5                  10                  15 tgg gac tac gcg att tcc aaa gtc gtc ttc acg tgt gcc gac agt ttt      96
Trp Asp Tyr Ala Ile Ser Lys Val Val Phe Thr Cys Ala Asp Ser Phe
```

```
                      20                  25                  30
cag tgg gac atc ggg cca gtg agt tcg agt acg gcg cat tta ccc gcc      144
Gln Trp Asp Ile Gly Pro Val Ser Ser Ser Thr Ala His Leu Pro Ala
         35                  40                  45 att gaa tcc cct acc cca ctg gtg act agc ctc ttg ttc tac tta gtc      192
Ile Glu Ser Pro Thr Pro Leu Val Thr Ser Leu Leu Phe Tyr Leu Val
 50                  55                  60 aca gtt ttc ttg tgg tat ggt cgt tta acc agg agt tca gac aag aaa      240
Thr Val Phe Leu Trp Tyr Gly Arg Leu Thr Arg Ser Ser Asp Lys Lys
 65                  70                  75                  80 att aga gag cct acg tgg tta aga aga ttc ata ata tgt cat aat gcg      288
Ile Arg Glu Pro Thr Trp Leu Arg Arg Phe Ile Ile Cys His Asn Ala
             85                  90                  95 ttc ttg ata gtc ctc agt ctt tac atg tgc ctt ggt tgt gtg gcc caa      336
Phe Leu Ile Val Leu Ser Leu Tyr Met Cys Leu Gly Cys Val Ala Gln
            100                 105                 110 gcg tat cag aat gga tat act tta tgg ggt aat gaa ttc aag gcc acg      384
Ala Tyr Gln Asn Gly Tyr Thr Leu Trp Gly Asn Glu Phe Lys Ala Thr
            115                 120                 125 gaa act cag ctt gct ctc tac att tac att ttt tac gta agt aaa ata      432
Glu Thr Gln Leu Ala Leu Tyr Ile Tyr Ile Phe Tyr Val Ser Lys Ile
130                 135                 140 tac gag ttt gta gat act tac att atg ctt ctc aag aat aac ttg cgg      480
Tyr Glu Phe Val Asp Thr Tyr Ile Met Leu Leu Lys Asn Asn Leu Arg
145                 150                 155                 160 caa gta aga ttc cta cac act tat cac cac agc acg att tcc ttt att      528
Gln Val Arg Phe Leu His Thr Tyr His His Ser Thr Ile Ser Phe Ile
                165                 170                 175 tgg tgg atc att gct cgg agg gct ccg ggt ggt gat gct tac ttc agc      576
Trp Trp Ile Ile Ala Arg Arg Ala Pro Gly Gly Asp Ala Tyr Phe Ser
            180                 185                 190 gcg gcc ttg aac tca tgg gta cac gtg tgc atg tac acc tat tat cta      624
Ala Ala Leu Asn Ser Trp Val His Val Cys Met Tyr Thr Tyr Tyr Leu
            195                 200                 205 tta tca acc ctt att gga aaa gaa gat cct aag cgt tcc aac tac ctt      672
Leu Ser Thr Leu Ile Gly Lys Glu Asp Pro Lys Arg Ser Asn Tyr Leu
210                 215                 220 tgg tgg ggt cgc cac cta acg caa atg cag atg ctt cag ttt ttc ttc      720
Trp Trp Gly Arg His Leu Thr Gln Met Gln Met Leu Gln Phe Phe Phe
225                 230                 235                 240 aac gta ctt caa gcg ttg tac tgc gct tcg ttc tct acg tat ccc aag      768
Asn Val Leu Gln Ala Leu Tyr Cys Ala Ser Phe Ser Thr Tyr Pro Lys
                245                 250                 255 ttt ttg tcc aaa att ctg ctc gtc tat atg atg agc ctt ctc ggc ttg      816
Phe Leu Ser Lys Ile Leu Leu Val Tyr Met Met Ser Leu Leu Gly Leu
            260                 265                 270 ttt ggg cat ttc tac tat tcc aag cac ata gca gca gct aag ctc cag      864
Phe Gly His Phe Tyr Tyr Ser Lys His Ile Ala Ala Ala Lys Leu Gln
            275                 280                 285 aaa aaa cag cag tga                                                  879
Lys Lys Gln Gln
    290

<210> SEQ ID NO 22
<211> LENGTH: 292
<212> TYPE: PRT
<213> ORGANISM: Ostreococcus tauri

<400> SEQUENCE: 22

Met Ser Gly Leu Arg Ala Pro Asn Phe Leu His Arg Phe Trp Thr Lys
```

```
                1               5                  10                 15
           Trp Asp Tyr Ala Ile Ser Lys Val Val Phe Thr Cys Ala Asp Ser Phe
                              20                  25                 30

Gln Trp Asp Ile Gly Pro Val Ser Ser Thr Ala His Leu Pro Ala
                       35                  40                  45

Ile Glu Ser Pro Thr Pro Leu Val Thr Ser Leu Leu Phe Tyr Leu Val
            50                  55                  60

Thr Val Phe Leu Trp Tyr Gly Arg Leu Thr Arg Ser Ser Asp Lys Lys
            65                  70                  75                  80

Ile Arg Glu Pro Thr Trp Leu Arg Arg Phe Ile Ile Cys His Asn Ala
                              85                  90                  95

Phe Leu Ile Val Leu Ser Leu Tyr Met Cys Leu Gly Cys Val Ala Gln
                             100                 105                 110

Ala Tyr Gln Asn Gly Tyr Thr Leu Trp Gly Asn Glu Phe Lys Ala Thr
                             115                 120                 125

Glu Thr Gln Leu Ala Leu Tyr Ile Tyr Ile Phe Tyr Val Ser Lys Ile
                       130                 135                 140

Tyr Glu Phe Val Asp Thr Tyr Ile Met Leu Leu Lys Asn Asn Leu Arg
           145                 150                 155                 160

Gln Val Arg Phe Leu His Thr Tyr His His Ser Thr Ile Ser Phe Ile
                             165                 170                 175

Trp Trp Ile Ile Ala Arg Arg Ala Pro Gly Gly Asp Ala Tyr Phe Ser
                             180                 185                 190

Ala Ala Leu Asn Ser Trp Val His Val Cys Met Tyr Thr Tyr Tyr Leu
                       195                 200                 205

Leu Ser Thr Leu Ile Gly Lys Glu Asp Pro Lys Arg Ser Asn Tyr Leu
                 210                 215                 220

Trp Trp Gly Arg His Leu Thr Gln Met Gln Met Leu Gln Phe Phe
           225                 230                 235                 240

Asn Val Leu Gln Ala Leu Tyr Cys Ala Ser Phe Ser Thr Tyr Pro Lys
                             245                 250                 255

Phe Leu Ser Lys Ile Leu Leu Val Tyr Met Met Ser Leu Leu Gly Leu
                       260                 265                 270

Phe Gly His Phe Tyr Tyr Ser Lys His Ile Ala Ala Ala Lys Leu Gln
                       275                 280                 285

Lys Lys Gln Gln
                 290

<210> SEQ ID NO 23
<211> LENGTH: 1611
<212> TYPE: DNA
<213> ORGANISM: Ostreococcus tauri
<220> FEATURE:
<221> NAME/KEY: CDS
<222> LOCATION: (1)..(1611)
<223> OTHER INFORMATION: Delta-4-Desaturase

<400> SEQUENCE: 23 atg tac ctc gga cgc ggc cgt ctc gag agc ggg acg acg cga ggg atg       48
Met Tyr Leu Gly Arg Gly Arg Leu Glu Ser Gly Thr Thr Arg Gly Met
 1                5                 10                  15 atg cgg acg cac gcg cgg cga ccg tcg acg acg tcg aat ccg tgc gcg       96
Met Arg Thr His Ala Arg Arg Pro Ser Thr Thr Ser Asn Pro Cys Ala
            20                  25                  30 cgg tca cgc gtg cgt aag acg acg gag cga tcg ctc gcg cga gtg cga      144
Arg Ser Arg Val Arg Lys Thr Thr Glu Arg Ser Leu Ala Arg Val Arg
        35                  40                  45
```

-continued

| | |
|---|---|
| cga tcg acg agt gag aag gga agc gcg ctc gtg ctc gag cga gag agc<br>Arg Ser Thr Ser Glu Lys Gly Ser Ala Leu Val Leu Glu Arg Glu Ser<br>50              55              60 | 192 |
| gaa cgg gag aag gag gag gga ggg aaa gcg cga gcg gag gga ttg cga<br>Glu Arg Glu Lys Glu Glu Gly Gly Lys Ala Arg Ala Glu Gly Leu Arg<br>65              70              75              80 | 240 |
| ttc caa cgc ccg gac gtc gcc gcg ccg ggg gga gcg gat cct tgg aac<br>Phe Gln Arg Pro Asp Val Ala Ala Pro Gly Gly Ala Asp Pro Trp Asn<br>                   85              90              95 | 288 |
| gac gag aag tgg aca aag acc aag tgg acg gta ttc aga gac gtc gcg<br>Asp Glu Lys Trp Thr Lys Thr Lys Trp Thr Val Phe Arg Asp Val Ala<br>             100             105             110 | 336 |
| tac gat ctc gat cct ttc ttc gct cga cac ccc gga gga gac tgg ctc<br>Tyr Asp Leu Asp Pro Phe Phe Ala Arg His Pro Gly Gly Asp Trp Leu<br>             115             120             125 | 384 |
| ctg aac ttg gcc gtg gga cga gac tgc acc gcg ctc atc gaa tcc tat<br>Leu Asn Leu Ala Val Gly Arg Asp Cys Thr Ala Leu Ile Glu Ser Tyr<br>130             135             140 | 432 |
| cac ttg cga cca gag gtg gcg acg gct cgt ttc aga atg ctg ccc aaa<br>His Leu Arg Pro Glu Val Ala Thr Ala Arg Phe Arg Met Leu Pro Lys<br>145             150             155             160 | 480 |
| ctc gag gat ttt ccc gtc gag gcc gtg ccc aag tcc ccg aga ccg aac<br>Leu Glu Asp Phe Pro Val Glu Ala Val Pro Lys Ser Pro Arg Pro Asn<br>                   165             170             175 | 528 |
| gat tcg ccg tta tac aac aac att cgc aac cga gtc cgc gaa gag ctc<br>Asp Ser Pro Leu Tyr Asn Asn Ile Arg Asn Arg Val Arg Glu Glu Leu<br>             180             185             190 | 576 |
| ttc cca gag gag gga aag aat atg cac aga cag ggc ggc gac cac ggc<br>Phe Pro Glu Glu Gly Lys Asn Met His Arg Gln Gly Gly Asp His Gly<br>             195             200             205 | 624 |
| gac ggt gac gat tct ggg ttt cgc cgc ctt ttg ctt atg ccg tgt acc<br>Asp Gly Asp Asp Ser Gly Phe Arg Arg Leu Leu Leu Met Pro Cys Thr<br>210             215             220 | 672 |
| tat tcc ctt ccg ggg gtt cct ttc cgg ctg cct cct cgg gtc tcg cgg<br>Tyr Ser Leu Pro Gly Val Pro Phe Arg Leu Pro Pro Arg Val Ser Arg<br>225             230             235             240 | 720 |
| ggg cgt gga ttg gtc tca cga ttc agg cac tgc gcc aac cac ggc gcg<br>Gly Arg Gly Leu Val Ser Arg Phe Arg His Cys Ala Asn His Gly Ala<br>                   245             250             255 | 768 |
| atg tct cct tcg ccg gcc gtt aac ggc gtc ctc ggt ttg acg aac gat<br>Met Ser Pro Ser Pro Ala Val Asn Gly Val Leu Gly Leu Thr Asn Asp<br>             260             265             270 | 816 |
| ctc atc ggc ggc tcg tcc ttg atg tgg aga tat cac cac caa gtc agc<br>Leu Ile Gly Gly Ser Ser Leu Met Trp Arg Tyr His His Gln Val Ser<br>             275             280             285 | 864 |
| cac cac att cat tgc aac gac aac gcc atg gat caa gac gtg tac acg<br>His His Ile His Cys Asn Asp Asn Ala Met Asp Gln Asp Val Tyr Thr<br>290             295             300 | 912 |
| gcg atg cca tta ttg cgt ttc gac gct cgc cgg ccc aag tcc tgg tac<br>Ala Met Pro Leu Leu Arg Phe Asp Ala Arg Arg Pro Lys Ser Trp Tyr<br>305             310             315             320 | 960 |
| cat cgc ttc cag cag tgg tac atg ttt tta gcg ttc ccg ttg ttg cag<br>His Arg Phe Gln Gln Trp Tyr Met Phe Leu Ala Phe Pro Leu Leu Gln<br>                   325             330             335 | 1008 |
| gtt gcc ttc caa gtc gga gac att gcc gca ctg ttc acg cgt gat acc<br>Val Ala Phe Gln Val Gly Asp Ile Ala Ala Leu Phe Thr Arg Asp Thr<br>             340             345             350 | 1056 |
| gaa ggc gct aag ctt cac ggg gcg acg acg tgg gag ctt acc acg gtt<br>Glu Gly Ala Lys Leu His Gly Ala Thr Thr Trp Glu Leu Thr Thr Val | 1104 |

```
                355                 360                 365
gtc ctc ggt aag att gtg cac ttc ggt ctt ttg ttg ggg ccg ttg atg      1152
Val Leu Gly Lys Ile Val His Phe Gly Leu Leu Leu Gly Pro Leu Met
    370                 375                 380 aac cac gcg gtg agt tct gtt ttg ctg ggg atc gtc ggt ttc atg gcg      1200
Asn His Ala Val Ser Ser Val Leu Leu Gly Ile Val Gly Phe Met Ala
385                 390                 395                 400 tgc caa ggt ata gtt ctg gcg tgc acg ttt gct gtg agt cac aat gtc      1248
Cys Gln Gly Ile Val Leu Ala Cys Thr Phe Ala Val Ser His Asn Val
            405                 410                 415 gcg gag gcg aag ata cct gag gac acc gga gga gaa gcc tgg gag aga      1296
Ala Glu Ala Lys Ile Pro Glu Asp Thr Gly Gly Glu Ala Trp Glu Arg
        420                 425                 430 gat tgg ggt gtc cag cag ttg gtg act agc gcc gac tgg ggt gga aag      1344
Asp Trp Gly Val Gln Gln Leu Val Thr Ser Ala Asp Trp Gly Gly Lys
    435                 440                 445 ata ggt aac ttc ttc acg ggt ggc ctc aac ttg caa gtt gag cac cac      1392
Ile Gly Asn Phe Phe Thr Gly Gly Leu Asn Leu Gln Val Glu His His
450                 455                 460 ttg ttt ccg gcg att tgc ttc gtc cac tac ccg gac atc gcg aag atc      1440
Leu Phe Pro Ala Ile Cys Phe Val His Tyr Pro Asp Ile Ala Lys Ile
465                 470                 475                 480 gtg aag gaa gaa gcg gcc aag ctc aac atc cct tac gcg tct tac agg      1488
Val Lys Glu Glu Ala Ala Lys Leu Asn Ile Pro Tyr Ala Ser Tyr Arg
            485                 490                 495 act ctt cct ggt att ttc gtc caa ttc tgg aga ttt atg aag gac atg      1536
Thr Leu Pro Gly Ile Phe Val Gln Phe Trp Arg Phe Met Lys Asp Met
        500                 505                 510 ggc acg gct gag caa att ggt gaa gtt cca ttg ccg aag att ccc aac      1584
Gly Thr Ala Glu Gln Ile Gly Glu Val Pro Leu Pro Lys Ile Pro Asn
    515                 520                 525 ccg cag ctc gcg ccg aag ctc gct tag                                  1611
Pro Gln Leu Ala Pro Lys Leu Ala
    530                 535

<210> SEQ ID NO 24
<211> LENGTH: 536
<212> TYPE: PRT
<213> ORGANISM: Ostreococcus tauri

<400> SEQUENCE: 24

Met Tyr Leu Gly Arg Gly Arg Leu Glu Ser Gly Thr Thr Arg Gly Met
1               5                   10                  15

Met Arg Thr His Ala Arg Arg Pro Ser Thr Thr Ser Asn Pro Cys Ala
            20                  25                  30

Arg Ser Arg Val Arg Lys Thr Thr Glu Arg Ser Leu Ala Arg Val Arg
        35                  40                  45

Arg Ser Thr Ser Glu Lys Gly Ser Ala Leu Val Leu Glu Arg Glu Ser
    50                  55                  60

Glu Arg Glu Lys Glu Gly Gly Lys Ala Arg Ala Glu Gly Leu Arg
65                  70                  75                  80

Phe Gln Arg Pro Asp Val Ala Ala Pro Gly Gly Ala Asp Pro Trp Asn
                85                  90                  95

Asp Glu Lys Trp Thr Lys Thr Lys Trp Thr Val Phe Arg Asp Val Ala
            100                 105                 110

Tyr Asp Leu Asp Pro Phe Phe Ala Arg His Pro Gly Gly Asp Trp Leu
        115                 120                 125

Leu Asn Leu Ala Val Gly Arg Asp Cys Thr Ala Leu Ile Glu Ser Tyr
```

```
              130                 135                 140
His Leu Arg Pro Glu Val Ala Thr Ala Arg Phe Arg Met Leu Pro Lys
145                 150                 155                 160

Leu Glu Asp Phe Pro Val Glu Ala Val Pro Lys Ser Pro Arg Pro Asn
                165                 170                 175

Asp Ser Pro Leu Tyr Asn Asn Ile Arg Asn Arg Val Arg Glu Glu Leu
                180                 185                 190

Phe Pro Glu Glu Gly Lys Asn Met His Arg Gln Gly Gly Asp His Gly
            195                 200                 205

Asp Gly Asp Asp Ser Gly Phe Arg Arg Leu Leu Leu Met Pro Cys Thr
        210                 215                 220

Tyr Ser Leu Pro Gly Val Pro Phe Arg Leu Pro Pro Arg Val Ser Arg
225                 230                 235                 240

Gly Arg Gly Leu Val Ser Arg Phe Arg His Cys Ala Asn His Gly Ala
                245                 250                 255

Met Ser Pro Ser Pro Ala Val Asn Gly Val Leu Gly Leu Thr Asn Asp
                260                 265                 270

Leu Ile Gly Gly Ser Ser Leu Met Trp Arg Tyr His His Gln Val Ser
            275                 280                 285

His His Ile His Cys Asn Asp Asn Ala Met Asp Gln Asp Val Tyr Thr
        290                 295                 300

Ala Met Pro Leu Leu Arg Phe Asp Ala Arg Arg Pro Lys Ser Trp Tyr
305                 310                 315                 320

His Arg Phe Gln Gln Trp Tyr Met Phe Leu Ala Phe Pro Leu Leu Gln
                325                 330                 335

Val Ala Phe Gln Val Gly Asp Ile Ala Ala Leu Phe Thr Arg Asp Thr
                340                 345                 350

Glu Gly Ala Lys Leu His Gly Ala Thr Thr Trp Glu Leu Thr Thr Val
            355                 360                 365

Val Leu Gly Lys Ile Val His Phe Gly Leu Leu Leu Gly Pro Leu Met
        370                 375                 380

Asn His Ala Val Ser Ser Val Leu Leu Gly Ile Val Gly Phe Met Ala
385                 390                 395                 400

Cys Gln Gly Ile Val Leu Ala Cys Thr Phe Ala Val Ser His Asn Val
                405                 410                 415

Ala Glu Ala Lys Ile Pro Glu Asp Thr Gly Gly Glu Ala Trp Glu Arg
            420                 425                 430

Asp Trp Gly Val Gln Gln Leu Val Thr Ser Ala Asp Trp Gly Gly Lys
        435                 440                 445

Ile Gly Asn Phe Phe Thr Gly Leu Asn Leu Gln Val Glu His His
450                 455                 460

Leu Phe Pro Ala Ile Cys Phe Val His Tyr Pro Asp Ile Ala Lys Ile
465                 470                 475                 480

Val Lys Glu Glu Ala Lys Leu Asn Ile Pro Tyr Ala Ser Tyr Arg
                485                 490                 495

Thr Leu Pro Gly Ile Phe Val Gln Phe Trp Arg Phe Met Lys Asp Met
                500                 505                 510

Gly Thr Ala Glu Gln Ile Gly Glu Val Pro Leu Pro Lys Ile Pro Asn
            515                 520                 525

Pro Gln Leu Ala Pro Lys Leu Ala
    530                 535

<210> SEQ ID NO 25
```

<211> LENGTH: 606
<212> TYPE: DNA
<213> ORGANISM: Ostreococcus tauri
<220> FEATURE:
<221> NAME/KEY: CDS
<222> LOCATION: (1)..(606)
<223> OTHER INFORMATION: Delta-5-Desaturase

<400> SEQUENCE: 25

```
atg tac ggt ttg cta tcg ctc aag tcg tgc ttc gtc gac gat ttc aac      48
Met Tyr Gly Leu Leu Ser Leu Lys Ser Cys Phe Val Asp Asp Phe Asn
 1               5                  10                  15 gcc tac ttc tcc gga cgc atc ggc tgg gtc aag gtg atg aag ttc acc      96
Ala Tyr Phe Ser Gly Arg Ile Gly Trp Val Lys Val Met Lys Phe Thr
             20                  25                  30 cgc ggc gag gcg atc gca ttt tgg ggc acc aag ctc ttg tgg gcc gcg     144
Arg Gly Glu Ala Ile Ala Phe Trp Gly Thr Lys Leu Leu Trp Ala Ala
         35                  40                  45 tat tac ctc gcg ttg ccg cta aag atg tcg cat cgg ccg ctc gga gaa     192
Tyr Tyr Leu Ala Leu Pro Leu Lys Met Ser His Arg Pro Leu Gly Glu
     50                  55                  60 ctc ctc gca ctc tgg gcc gtc acc gag ttc gtc acc gga tgg ctg ttg     240
Leu Leu Ala Leu Trp Ala Val Thr Glu Phe Val Thr Gly Trp Leu Leu
 65                  70                  75                  80 gcg ttc atg ttc caa gtc gcc cac gtc gtc ggc gag gtt cac ttc ttc     288
Ala Phe Met Phe Gln Val Ala His Val Val Gly Glu Val His Phe Phe
                 85                  90                  95 acc ctc gac gcg aag aac cgc gtg aac ttg gga tgg gga gag gca cag     336
Thr Leu Asp Ala Lys Asn Arg Val Asn Leu Gly Trp Gly Glu Ala Gln
            100                 105                 110 ctc atg tcg agc gcg gat ttc gcc cac gga tcc aag ttt tgg acg cac     384
Leu Met Ser Ser Ala Asp Phe Ala His Gly Ser Lys Phe Trp Thr His
        115                 120                 125 ttc tcc gga ggc tta aac tac caa gtc gtc cac cat ctc ttc ccg ggc     432
Phe Ser Gly Gly Leu Asn Tyr Gln Val Val His His Leu Phe Pro Gly
    130                 135                 140 gtc tgc cac gtg cac tat ccc gcg ctc gcg cca att att aag gcg gca     480
Val Cys His Val His Tyr Pro Ala Leu Ala Pro Ile Ile Lys Ala Ala
145                 150                 155                 160 gct gag aag cac ggc ctc cac tac cag att tac ccc acg ttt tgg tcc     528
Ala Glu Lys His Gly Leu His Tyr Gln Ile Tyr Pro Thr Phe Trp Ser
                165                 170                 175 gcc ctg cgc gcg cac ttc cgg cac ctc gcc aac gtc ggc cgc gcc gcg     576
Ala Leu Arg Ala His Phe Arg His Leu Ala Asn Val Gly Arg Ala Ala
            180                 185                 190 tac gta ccg tcc ctc caa acc gtc gga tga                             606
Tyr Val Pro Ser Leu Gln Thr Val Gly
        195                 200
```

<210> SEQ ID NO 26
<211> LENGTH: 201
<212> TYPE: PRT
<213> ORGANISM: Ostreococcus tauri

<400> SEQUENCE: 26

```
Met Tyr Gly Leu Leu Ser Leu Lys Ser Cys Phe Val Asp Asp Phe Asn
 1               5                  10                  15

Ala Tyr Phe Ser Gly Arg Ile Gly Trp Val Lys Val Met Lys Phe Thr
             20                  25                  30

Arg Gly Glu Ala Ile Ala Phe Trp Gly Thr Lys Leu Leu Trp Ala Ala
         35                  40                  45
```

```
Tyr Tyr Leu Ala Leu Pro Leu Lys Met Ser His Arg Pro Leu Gly Glu
     50                  55                  60

Leu Leu Ala Leu Trp Ala Val Thr Glu Phe Val Thr Gly Trp Leu Leu
 65                  70                  75                  80

Ala Phe Met Phe Gln Val Ala His Val Val Gly Glu Val His Phe Phe
                 85                  90                  95

Thr Leu Asp Ala Lys Asn Arg Val Asn Leu Gly Trp Gly Glu Ala Gln
                100                 105                 110

Leu Met Ser Ser Ala Asp Phe Ala His Gly Ser Lys Phe Trp Thr His
            115                 120                 125

Phe Ser Gly Gly Leu Asn Tyr Gln Val Val His Leu Phe Pro Gly
130                 135                 140

Val Cys His Val His Tyr Pro Ala Leu Ala Pro Ile Ile Lys Ala Ala
145                 150                 155                 160

Ala Glu Lys His Gly Leu His Tyr Gln Ile Tyr Pro Thr Phe Trp Ser
                165                 170                 175

Ala Leu Arg Ala His Phe Arg His Leu Ala Asn Val Gly Arg Ala Ala
            180                 185                 190

Tyr Val Pro Ser Leu Gln Thr Val Gly
                195                 200

<210> SEQ ID NO 27
<211> LENGTH: 714
<212> TYPE: DNA
<213> ORGANISM: Ostreococcus tauri
<220> FEATURE:
<221> NAME/KEY: CDS
<222> LOCATION: (1)..(714)
<223> OTHER INFORMATION: Delta-5-Desaturase

<400> SEQUENCE: 27 atg gtg agc cat cac tcg tac tgt aac gac gcg gat ttg gat cag gat      48
Met Val Ser His His Ser Tyr Cys Asn Asp Ala Asp Leu Asp Gln Asp
 1               5                  10                  15 gtg tac acc gca ctg ccg ctc ctg cgc ctg gac ccg tct cag gag ttg      96
Val Tyr Thr Ala Leu Pro Leu Leu Arg Leu Asp Pro Ser Gln Glu Leu
                 20                  25                  30 aag tgg ttt cat cga tac cag gcg ttt tac gcc ccg ctc atg tgg ccg     144
Lys Trp Phe His Arg Tyr Gln Ala Phe Tyr Ala Pro Leu Met Trp Pro
             35                  40                  45 ttt ttg tgg ctc gcg gcg cag ttt ggc gac gcg cag aac atc ctg atc     192
Phe Leu Trp Leu Ala Ala Gln Phe Gly Asp Ala Gln Asn Ile Leu Ile
 50                  55                  60 gac cga gcg tcg ccg ggc gtc gcg tac aag gga ttg atg gcg aac gag     240
Asp Arg Ala Ser Pro Gly Val Ala Tyr Lys Gly Leu Met Ala Asn Glu
 65                  70                  75                  80 gtc gcg ctg tac gtt ctc ggt aag gtt tta cac ttt ggt ctt ctc ctc     288
Val Ala Leu Tyr Val Leu Gly Lys Val Leu His Phe Gly Leu Leu Leu
                 85                  90                  95 ggc gtt cct gcg tac ttg cac gga ttg tcc aac gcg atc gtt cca ttc     336
Gly Val Pro Ala Tyr Leu His Gly Leu Ser Asn Ala Ile Val Pro Phe
                100                 105                 110 ttg gcg tac ggc gca ttc ggc tcc ttc gtc ctg tgc tgg ttc ttc atc     384
Leu Ala Tyr Gly Ala Phe Gly Ser Phe Val Leu Cys Trp Phe Phe Ile
            115                 120                 125 gtc agc cat aac ctc gaa gcg ctg aca ccc gtt aac ctt aac aag tcc     432
Val Ser His Asn Leu Glu Ala Leu Thr Pro Val Asn Leu Asn Lys Ser
130                 135                 140 acg aag aac gac tgg ggg gcg tgg cag atc gag aca tcg gcg tct tgg     480
```

```
Thr Lys Asn Asp Trp Gly Ala Trp Gln Ile Glu Thr Ser Ala Ser Trp
145                 150                 155                 160 ggc aac gcg ttc tgg agc ttc ttc tct gga ggt ctg aac ctg caa atc       528
Gly Asn Ala Phe Trp Ser Phe Phe Ser Gly Gly Leu Asn Leu Gln Ile
                165                 170                 175 gag cac cac ctc ttc ccg ggc atg gcg cac aac ctg tac ccg aag atg       576
Glu His His Leu Phe Pro Gly Met Ala His Asn Leu Tyr Pro Lys Met
            180                 185                 190 gtg ccg atc atc aag gac gag tgt gcg aaa gcg ggc gtt cgc tac acc       624
Val Pro Ile Ile Lys Asp Glu Cys Ala Lys Ala Gly Val Arg Tyr Thr
            195                 200                 205 ggt tac ggt ggc tac acc ggc ctg ctc ccg atc acc cgc gac atg ttc       672
Gly Tyr Gly Gly Tyr Thr Gly Leu Leu Pro Ile Thr Arg Asp Met Phe
210                 215                 220 tcc tac ctc cat aag tgt ggc cga acg gcg aaa cta gcc taa               714
Ser Tyr Leu His Lys Cys Gly Arg Thr Ala Lys Leu Ala
225                 230                 235

<210> SEQ ID NO 28
<211> LENGTH: 237
<212> TYPE: PRT
<213> ORGANISM: Ostreococcus tauri

<400> SEQUENCE: 28

Met Val Ser His His Ser Tyr Cys Asn Asp Ala Asp Leu Asp Gln Asp
1               5                   10                  15

Val Tyr Thr Ala Leu Pro Leu Leu Arg Leu Asp Pro Ser Gln Glu Leu
            20                  25                  30

Lys Trp Phe His Arg Tyr Gln Ala Phe Tyr Ala Pro Leu Met Trp Pro
        35                  40                  45

Phe Leu Trp Leu Ala Ala Gln Phe Gly Asp Ala Gln Asn Ile Leu Ile
    50                  55                  60

Asp Arg Ala Ser Pro Gly Val Ala Tyr Lys Gly Leu Met Ala Asn Glu
65                  70                  75                  80

Val Ala Leu Tyr Val Leu Gly Lys Val Leu His Phe Gly Leu Leu Leu
                85                  90                  95

Gly Val Pro Ala Tyr Leu His Gly Leu Ser Asn Ala Ile Val Pro Phe
            100                 105                 110

Leu Ala Tyr Gly Ala Phe Gly Ser Phe Val Leu Cys Trp Phe Phe Ile
        115                 120                 125

Val Ser His Asn Leu Glu Ala Leu Thr Pro Val Asn Leu Asn Lys Ser
    130                 135                 140

Thr Lys Asn Asp Trp Gly Ala Trp Gln Ile Glu Thr Ser Ala Ser Trp
145                 150                 155                 160

Gly Asn Ala Phe Trp Ser Phe Phe Ser Gly Gly Leu Asn Leu Gln Ile
                165                 170                 175

Glu His His Leu Phe Pro Gly Met Ala His Asn Leu Tyr Pro Lys Met
            180                 185                 190

Val Pro Ile Ile Lys Asp Glu Cys Ala Lys Ala Gly Val Arg Tyr Thr
        195                 200                 205

Gly Tyr Gly Gly Tyr Thr Gly Leu Leu Pro Ile Thr Arg Asp Met Phe
    210                 215                 220

Ser Tyr Leu His Lys Cys Gly Arg Thr Ala Lys Leu Ala
225                 230                 235

<210> SEQ ID NO 29
<211> LENGTH: 1371
```

```
<212> TYPE: DNA
<213> ORGANISM: Ostreococcus tauri
<220> FEATURE:
<221> NAME/KEY: CDS
<222> LOCATION: (1)..(1371)
<223> OTHER INFORMATION: Delta-6-Desaturase

<400> SEQUENCE: 29 atg tgc gtg gag acg gaa aat aac gat ggg atc ccc acg gtg gag atc      48
Met Cys Val Glu Thr Glu Asn Asn Asp Gly Ile Pro Thr Val Glu Ile
 1               5                  10                  15 gcg ttc gac ggt gag cgc gag cgg gcg gag gca aac gtg aag ctg tcc      96
Ala Phe Asp Gly Glu Arg Glu Arg Ala Glu Ala Asn Val Lys Leu Ser
             20                  25                  30 gcg gag aag atg gag ccg gcg gcg ctg gcg aag acg ttc gcg agg cgg     144
Ala Glu Lys Met Glu Pro Ala Ala Leu Ala Lys Thr Phe Ala Arg Arg
         35                  40                  45 tac gtc gtg atc gag ggg gtg gag tac gat gtg acg gat ttt aag cac     192
Tyr Val Val Ile Glu Gly Val Glu Tyr Asp Val Thr Asp Phe Lys His
     50                  55                  60 ccg gga gga acg gtt att ttc tat gcg ttg tca aac acc ggg gcg gac     240
Pro Gly Gly Thr Val Ile Phe Tyr Ala Leu Ser Asn Thr Gly Ala Asp
 65                  70                  75                  80 gcg acg gaa gcg ttc aag gag ttt cat cat cgg tcg aga aag gcg agg     288
Ala Thr Glu Ala Phe Lys Glu Phe His His Arg Ser Arg Lys Ala Arg
                 85                  90                  95 aaa gcc ttg gcg gcg ctc ccg tct cga ccg gcc aag acg gcc aag gtg     336
Lys Ala Leu Ala Ala Leu Pro Ser Arg Pro Ala Lys Thr Ala Lys Val
            100                 105                 110 gac gac gcg gag atg ctc caa gat ttc gcc aag tgg cgg aaa gaa ttg     384
Asp Asp Ala Glu Met Leu Gln Asp Phe Ala Lys Trp Arg Lys Glu Leu
        115                 120                 125 gag aga gat gga ttc ttc aag ccc tct ccg gcg cac gtg gcg tat cgc     432
Glu Arg Asp Gly Phe Phe Lys Pro Ser Pro Ala His Val Ala Tyr Arg
    130                 135                 140 ttc gcc gag ctc gcg gcg atg tac gct ctc ggg acg tac ctg atg tac     480
Phe Ala Glu Leu Ala Ala Met Tyr Ala Leu Gly Thr Tyr Leu Met Tyr
145                 150                 155                 160 gct cga tac gtc gtc tcc tcg gtg ctc gtg tac gct tgc ttt ttc ggc     528
Ala Arg Tyr Val Val Ser Ser Val Leu Val Tyr Ala Cys Phe Phe Gly
                165                 170                 175 gcc cga tgc ggt tgg gtg cag cac gag ggc gga cac agc tcg ctg acg     576
Ala Arg Cys Gly Trp Val Gln His Glu Gly Gly His Ser Ser Leu Thr
            180                 185                 190 ggc aac att tgg tgg gac aag cgc atc cag gcc ttc aca gcc ggg ttc     624
Gly Asn Ile Trp Trp Asp Lys Arg Ile Gln Ala Phe Thr Ala Gly Phe
        195                 200                 205 ggt ctc gcc ggt agc ggc gac atg tgg aac tcg atg cac aac aag cat     672
Gly Leu Ala Gly Ser Gly Asp Met Trp Asn Ser Met His Asn Lys His
    210                 215                 220 cac gcg acg cct caa aag gtt cgt cac gac atg gat ctg gac acc acc     720
His Ala Thr Pro Gln Lys Val Arg His Asp Met Asp Leu Asp Thr Thr
225                 230                 235                 240 ccc gcg gtg gcg ttc ttc aac acc gcg gtg gaa gac aat cgt ccc cgt     768
Pro Ala Val Ala Phe Phe Asn Thr Ala Val Glu Asp Asn Arg Pro Arg
                245                 250                 255 ggc ttt agc aag tac tgg ttg cgc ctt cag gcg tgg acc ttc atc ccc     816
Gly Phe Ser Lys Tyr Trp Leu Arg Leu Gln Ala Trp Thr Phe Ile Pro
            260                 265                 270 gtg acg tcc ggc ttg gtg ctc ctt ttc tgg atg ttt ttc ctc cac ccc     864
Val Thr Ser Gly Leu Val Leu Leu Phe Trp Met Phe Phe Leu His Pro
```

```
                275                 280                 285
tcc aag gct ttg aag ggt ggc aag tac gaa gag ttg gtg tgg atg ctc         912
Ser Lys Ala Leu Lys Gly Gly Lys Tyr Glu Glu Leu Val Trp Met Leu
290                 295                 300 gcc gcg cac gtc atc cgc acg tgg acg atc aag gcg gtg acc gga ttc         960
Ala Ala His Val Ile Arg Thr Trp Thr Ile Lys Ala Val Thr Gly Phe
305                 310                 315                 320 acc gcg atg cag tcc tac ggc tta ttt ttg gcg acg agc tgg gtg agc        1008
Thr Ala Met Gln Ser Tyr Gly Leu Phe Leu Ala Thr Ser Trp Val Ser
                325                 330                 335 ggc tgc tat ctg ttt gca cac ttc tcc acg tcg cac acg cac ctg gat        1056
Gly Cys Tyr Leu Phe Ala His Phe Ser Thr Ser His Thr His Leu Asp
340                 345                 350 gtg gtg ccc gcg gac gag cat ctc tcc tgg gtt cga tac gcc gtc gat        1104
Val Val Pro Ala Asp Glu His Leu Ser Trp Val Arg Tyr Ala Val Asp
355                 360                 365 cac acg atc gac atc gat ccg agt caa ggt tgg gtg aac tgg ttg atg        1152
His Thr Ile Asp Ile Asp Pro Ser Gln Gly Trp Val Asn Trp Leu Met
370                 375                 380 ggc tac ctc aac tgc caa gtc atc cac cac ctc ttt ccg agc atg ccg        1200
Gly Tyr Leu Asn Cys Gln Val Ile His His Leu Phe Pro Ser Met Pro
385                 390                 395                 400 cag ttc cgc cag ccc gag gta tct cgc cgc ttc gtc gcc ttt gcg aaa        1248
Gln Phe Arg Gln Pro Glu Val Ser Arg Arg Phe Val Ala Phe Ala Lys
                405                 410                 415 aag tgg aac ctc aac tac aag gtc atg acc tac gcc ggt gcg tgg aag        1296
Lys Trp Asn Leu Asn Tyr Lys Val Met Thr Tyr Ala Gly Ala Trp Lys
420                 425                 430 gca acg ctc gga aac ctc gac aac gtg ggt aag cac tac tac gtg cac        1344
Ala Thr Leu Gly Asn Leu Asp Asn Val Gly Lys His Tyr Tyr Val His
435                 440                 445 ggc caa cac tcc gga aag acg gcg taa                                     1371
Gly Gln His Ser Gly Lys Thr Ala
450                 455

<210> SEQ ID NO 30
<211> LENGTH: 456
<212> TYPE: PRT
<213> ORGANISM: Ostreococcus tauri

<400> SEQUENCE: 30

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
```

```
                130                 135                 140
Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly His Ser Ser Leu Thr
                180                 185                 190

Gly Asn Ile Trp Trp Asp Lys Arg Ile Gln Ala Phe Thr Ala Gly Phe
                195                 200                 205

Gly Leu Ala Gly Ser Gly Asp Met Trp Asn Ser Met His Asn Lys His
210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
                260                 265                 270

Val Thr Ser Gly Leu Val Leu Leu Phe Trp Met Phe Phe Leu His Pro
                275                 280                 285

Ser Lys Ala Leu Lys Gly Gly Lys Tyr Glu Glu Leu Val Trp Met Leu
290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
                340                 345                 350

Val Val Pro Ala Asp Glu His Leu Ser Trp Val Arg Tyr Ala Val Asp
                355                 360                 365

His Thr Ile Asp Ile Asp Pro Ser Gln Gly Trp Val Asn Trp Leu Met
370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
                420                 425                 430

Ala Thr Leu Gly Asn Leu Asp Asn Val Gly Lys His Tyr Tyr Val His
                435                 440                 445

Gly Gln His Ser Gly Lys Thr Ala
450                 455

<210> SEQ ID NO 31
<211> LENGTH: 1086
<212> TYPE: DNA
<213> ORGANISM: Ostreococcus tauri
<220> FEATURE:
<221> NAME/KEY: CDS
<222> LOCATION: (1)..(1086)
<223> OTHER INFORMATION: Delta-12-Desaturase

<400> SEQUENCE: 31 atg cag gag ggg gtg cga aac att ccg aac gag tgc ttt gag acg gga    48
Met Gln Glu Gly Val Arg Asn Ile Pro Asn Glu Cys Phe Glu Thr Gly
 1               5                  10                  15 cat ctt gaa aga ccc tgg cgt tcc ggc cgg tgt ggg cgc gat ccc ggt    96
```

```
            His Leu Glu Arg Pro Trp Arg Ser Gly Arg Cys Gly Arg Asp Pro Gly
                        20                  25                  30 tcg aat tgg ggc gct ggc ttc cgc ttt ttt tcg ctc aag ggg ttt tgg        144
Ser Asn Trp Gly Ala Gly Phe Arg Phe Phe Ser Leu Lys Gly Phe Trp
             35                  40                  45 tgg ccg gcg tgg tgg gcg tac gcg ttc gtg acg ggg acg gcg gcc act        192
Trp Pro Ala Trp Trp Ala Tyr Ala Phe Val Thr Gly Thr Ala Ala Thr
         50                  55                  60 ggg tgt tgg gtc gcc gcg cac gag tgc ggg cac ggc gcg ttc agc gat        240
Gly Cys Trp Val Ala Ala His Glu Cys Gly His Gly Ala Phe Ser Asp
 65                  70                  75                  80 aac aag acg ttg caa gat gcg gtt gga tac gtg ttg cac tcg ttg ctc        288
Asn Lys Thr Leu Gln Asp Ala Val Gly Tyr Val Leu His Ser Leu Leu
                 85                  90                  95 ttg gtg ccg tac ttt tct tgg cag cga tca cac gcg gtg cat cac tcg        336
Leu Val Pro Tyr Phe Ser Trp Gln Arg Ser His Ala Val His His Ser
             100                 105                 110 agg acg aat cac gtt ctt gag ggc gag acg cac gtg ccg gcg cgc ttg        384
Arg Thr Asn His Val Leu Glu Gly Glu Thr His Val Pro Ala Arg Leu
         115                 120                 125 ggg acg gaa gac gcc aac gtc gtg ttc aag ctt cgc gaa ttg atc ggt        432
Gly Thr Glu Asp Ala Asn Val Val Phe Lys Leu Arg Glu Leu Ile Gly
130                 135                 140 gaa ggg ccg ttc acg ttt ttc aac ctc gtc ggc gtc ttc gcg ctc gga        480
Glu Gly Pro Phe Thr Phe Phe Asn Leu Val Gly Val Phe Ala Leu Gly
145                 150                 155                 160 tgg ccg att tac ttg ctc acc ggc gcg agc ggc gga ccg gtg cgc ggt        528
Trp Pro Ile Tyr Leu Leu Thr Gly Ala Ser Gly Gly Pro Val Arg Gly
                165                 170                 175 aac acg aac cac ttc tta ccc ttc atg ggc gag aaa ggt aag cac gcg        576
Asn Thr Asn His Phe Leu Pro Phe Met Gly Glu Lys Gly Lys His Ala
            180                 185                 190 ctg ttc ccg ggt aag tgg gcg aag aag gtg tgg cag tct gac atc ggc        624
Leu Phe Pro Gly Lys Trp Ala Lys Lys Val Trp Gln Ser Asp Ile Gly
        195                 200                 205 gtt gtt gcc gtc ctg ggc gcg ctc gcg gct tgg gcg gcg cac agc ggg        672
Val Val Ala Val Leu Gly Ala Leu Ala Ala Trp Ala Ala His Ser Gly
210                 215                 220 att gcc aca gtg atg gca ctc tac gtc ggc ccg tac atg gtg acc aac        720
Ile Ala Thr Val Met Ala Leu Tyr Val Gly Pro Tyr Met Val Thr Asn
225                 230                 235                 240 ttt tgg ctc gtc ttg tac acg tgg tta cag cac acc gac gtt gac gtg        768
Phe Trp Leu Val Leu Tyr Thr Trp Leu Gln His Thr Asp Val Asp Val
                245                 250                 255 ccg cac ttc gag ggc gac gat tgg aac ttg gtc aag ggg gca ttc atg        816
Pro His Phe Glu Gly Asp Asp Trp Asn Leu Val Lys Gly Ala Phe Met
            260                 265                 270 acg atc gat cgc ccg tac ggc cca gtt ttt gat ttc ttg cac cac cgc        864
Thr Ile Asp Arg Pro Tyr Gly Pro Val Phe Asp Phe Leu His His Arg
        275                 280                 285 atc ggc agc acg cac gtc gcg cac cac atc aac aca cca ttc ccg cat        912
Ile Gly Ser Thr His Val Ala His His Ile Asn Thr Pro Phe Pro His
290                 295                 300 tac aag gct caa atg gcg acg gat gcg cta aag gag gcg tat ccc gac        960
Tyr Lys Ala Gln Met Ala Thr Asp Ala Leu Lys Glu Ala Tyr Pro Asp
305                 310                 315                 320 ctc tac ctt tac gat cca act ccg atc gcg acc gct acg tgg cgc gtg       1008
Leu Tyr Leu Tyr Asp Pro Thr Pro Ile Ala Thr Ala Thr Trp Arg Val
                325                 330                 335
```

```
ggg agc aag tgc atc gcc gtc gtg aag aag gga gac gaa tgg gtg ttc    1056
Gly Ser Lys Cys Ile Ala Val Val Lys Lys Gly Asp Glu Trp Val Phe
        340                 345                 350 acg gat aag caa ctc ccg gtc gcg gcg tga                            1086
Thr Asp Lys Gln Leu Pro Val Ala Ala
355                 360
```

<210> SEQ ID NO 32
<211> LENGTH: 361
<212> TYPE: PRT
<213> ORGANISM: Ostreococcus tauri

<400> SEQUENCE: 32

```
Met Gln Glu Gly Val Arg Asn Ile Pro Asn Glu Cys Phe Glu Thr Gly
1               5                   10                  15

His Leu Glu Arg Pro Trp Arg Ser Gly Arg Cys Gly Arg Asp Pro Gly
            20                  25                  30

Ser Asn Trp Gly Ala Gly Phe Arg Phe Ser Leu Lys Gly Phe Trp
        35                  40                  45

Trp Pro Ala Trp Trp Ala Tyr Ala Phe Val Thr Gly Thr Ala Ala Thr
    50                  55                  60

Gly Cys Trp Val Ala Ala His Glu Cys Gly His Gly Ala Phe Ser Asp
65                  70                  75                  80

Asn Lys Thr Leu Gln Asp Ala Val Gly Tyr Val Leu His Ser Leu Leu
                85                  90                  95

Leu Val Pro Tyr Phe Ser Trp Gln Arg Ser His Ala Val His His Ser
            100                 105                 110

Arg Thr Asn His Val Leu Glu Gly Glu Thr His Val Pro Ala Arg Leu
        115                 120                 125

Gly Thr Glu Asp Ala Asn Val Val Phe Lys Leu Arg Glu Leu Ile Gly
    130                 135                 140

Glu Gly Pro Phe Thr Phe Phe Asn Leu Val Gly Val Phe Ala Leu Gly
145                 150                 155                 160

Trp Pro Ile Tyr Leu Leu Thr Gly Ala Ser Gly Pro Val Arg Gly
                165                 170                 175

Asn Thr Asn His Phe Leu Pro Phe Met Gly Lys Gly Lys His Ala
            180                 185                 190

Leu Phe Pro Gly Lys Trp Ala Lys Lys Val Trp Gln Ser Asp Ile Gly
        195                 200                 205

Val Val Ala Val Leu Gly Ala Leu Ala Ala Trp Ala Ala His Ser Gly
    210                 215                 220

Ile Ala Thr Val Met Ala Leu Tyr Val Gly Pro Tyr Met Val Thr Asn
225                 230                 235                 240

Phe Trp Leu Val Leu Tyr Thr Trp Leu Gln His Thr Asp Val Asp Val
                245                 250                 255

Pro His Phe Glu Gly Asp Asp Trp Asn Leu Val Lys Gly Ala Phe Met
            260                 265                 270

Thr Ile Asp Arg Pro Tyr Gly Pro Val Phe Asp Phe Leu His His Arg
        275                 280                 285

Ile Gly Ser Thr His Val Ala His His Ile Asn Thr Pro Phe Pro His
    290                 295                 300

Tyr Lys Ala Gln Met Ala Thr Asp Ala Leu Lys Glu Ala Tyr Pro Asp
305                 310                 315                 320

Leu Tyr Leu Tyr Asp Pro Thr Pro Ile Ala Thr Ala Trp Arg Val
                325                 330                 335
```

```
Gly Ser Lys Cys Ile Ala Val Val Lys Lys Gly Asp Glu Trp Val Phe
            340                 345                 350

Thr Asp Lys Gln Leu Pro Val Ala Ala
        355                 360

<210> SEQ ID NO 33
<211> LENGTH: 1077
<212> TYPE: DNA
<213> ORGANISM: Thalassiosira pseudonana
<220> FEATURE:
<221> NAME/KEY: CDS
<222> LOCATION: (1)..(1077)
<223> OTHER INFORMATION: Delta-5-Elongase

<400> SEQUENCE: 33 atg tgc tca tca ccg ccg tca caa tcc aaa aca aca tcc ctc cta gca      48
Met Cys Ser Ser Pro Pro Ser Gln Ser Lys Thr Thr Ser Leu Leu Ala
 1               5                  10                  15 cgg tac acc acc gcc gcc ctc ctc ctc acc ctc aca aca tgg tgc          96
Arg Tyr Thr Thr Ala Ala Leu Leu Leu Thr Leu Thr Thr Trp Cys
             20                  25                  30 cac ttc gcc ttc cca gcc gcc acc gcc aca ccc ggc ctc acc gcc gaa    144
His Phe Ala Phe Pro Ala Ala Thr Ala Thr Pro Gly Leu Thr Ala Glu
         35                  40                  45 atg cac tcc tac aaa gtc cca ctc ggt ctc acc gta ttc tac ctg ctg    192
Met His Ser Tyr Lys Val Pro Leu Gly Leu Thr Val Phe Tyr Leu Leu
 50                  55                  60 agt cta ccg tca cta aag tac gtt acg gac aac tac ctt gcc aaa aag    240
Ser Leu Pro Ser Leu Lys Tyr Val Thr Asp Asn Tyr Leu Ala Lys Lys
 65                  70                  75                  80 tat gat atg aag tca ctc cta acg gaa tca atg gtg ttg tac aat gtg    288
Tyr Asp Met Lys Ser Leu Leu Thr Glu Ser Met Val Leu Tyr Asn Val
                 85                  90                  95 gcg caa gtg ctg ctc aat ggg tgg acg gtg tat gcg att gtg gat gcg    336
Ala Gln Val Leu Leu Asn Gly Trp Thr Val Tyr Ala Ile Val Asp Ala
            100                 105                 110 gtg atg aat aga gac cat ccg ttt att gga agt aga agt ttg gtt ggg    384
Val Met Asn Arg Asp His Pro Phe Ile Gly Ser Arg Ser Leu Val Gly
        115                 120                 125 gcg gcg ttg cat agt ggg agc tcg tat gcg gtg tgg gtt cat tat tgt    432
Ala Ala Leu His Ser Gly Ser Ser Tyr Ala Val Trp Val His Tyr Cys
    130                 135                 140 gat aag tat ttg gag ttc ttt gat acg tat ttt atg gtg ttg agg ggg    480
Asp Lys Tyr Leu Glu Phe Phe Asp Thr Tyr Phe Met Val Leu Arg Gly
145                 150                 155                 160 aaa atg gac cag gtc tcc ttc ctc cac atc tac cac cac acg acc ata    528
Lys Met Asp Gln Val Ser Phe Leu His Ile Tyr His His Thr Thr Ile
                165                 170                 175 gcg tgg gca tgg tgg atc gcc ctc cgc ttc tcc ccc ggt gga gac att    576
Ala Trp Ala Trp Trp Ile Ala Leu Arg Phe Ser Pro Gly Gly Asp Ile
            180                 185                 190 tac ttc ggg gca ctc ctc aac tcc atc atc cac gtc ctc atg tat tcc    624
Tyr Phe Gly Ala Leu Leu Asn Ser Ile Ile His Val Leu Met Tyr Ser
        195                 200                 205 tac tac gcc ctt gcc cta ctc aag gtc agt tgt cca tgg aaa cga tac    672
Tyr Tyr Ala Leu Ala Leu Leu Lys Val Ser Cys Pro Trp Lys Arg Tyr
    210                 215                 220 ctg act caa gct caa tta ttg caa ttc aca agt gtg gtg gtt tat acg    720
Leu Thr Gln Ala Gln Leu Leu Gln Phe Thr Ser Val Val Val Tyr Thr
225                 230                 235                 240 ggg tgt acg ggt tat act cat tac tat cat acg aag cat gga gcg gat    768
```

```
                Gly Cys Thr Gly Tyr Thr His Tyr Tyr His Thr Lys His Gly Ala Asp
                                245                 250                 255 gag aca cag cct agt tta gga acg tat tat ttc tgt tgt gga gtg cag                 816
Glu Thr Gln Pro Ser Leu Gly Thr Tyr Tyr Phe Cys Cys Gly Val Gln
            260                 265                 270 gtg ttt gag atg gtt agt ttg ttt gta ctc ttt tcc atc ttt tat aaa                 864
Val Phe Glu Met Val Ser Leu Phe Val Leu Phe Ser Ile Phe Tyr Lys
        275                 280                 285 cga tcc tat tcg aag aag aac aag tca gga gga aag gat agc aag aag                 912
Arg Ser Tyr Ser Lys Lys Asn Lys Ser Gly Gly Lys Asp Ser Lys Lys
    290                 295                 300 aat gat gat ggg aat aat gag gat caa tgt cac aag gct atg aag gat                 960
Asn Asp Asp Gly Asn Asn Glu Asp Gln Cys His Lys Ala Met Lys Asp
305                 310                 315                 320 ata tcg gag ggt gcg aag gag gtt gtg ggg cat gca gcg aag gat gct                1008
Ile Ser Glu Gly Ala Lys Glu Val Val Gly His Ala Ala Lys Asp Ala
                325                 330                 335 gga aag ttg gtg gct acg gcg agt aag gct gta aag agg aag gga act                1056
Gly Lys Leu Val Ala Thr Ala Ser Lys Ala Val Lys Arg Lys Gly Thr
            340                 345                 350 cgt gtt act ggt gcc atg tag                                                    1077
Arg Val Thr Gly Ala Met
        355

<210> SEQ ID NO 34
<211> LENGTH: 358
<212> TYPE: PRT
<213> ORGANISM: Thalassiosira pseudonana

<400> SEQUENCE: 34

Met Cys Ser Ser Pro Pro Ser Gln Ser Lys Thr Thr Ser Leu Leu Ala
 1               5                  10                  15

Arg Tyr Thr Thr Ala Ala Leu Leu Leu Thr Leu Thr Thr Trp Cys
            20                  25                  30

His Phe Ala Phe Pro Ala Ala Thr Ala Thr Pro Gly Leu Thr Ala Glu
        35                  40                  45

Met His Ser Tyr Lys Val Pro Leu Gly Leu Thr Val Phe Tyr Leu Leu
    50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125

Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
        195                 200                 205

Tyr Tyr Ala Leu Ala Leu Leu Lys Val Ser Cys Pro Trp Lys Arg Tyr
```

```
                    210                 215                 220
Leu Thr Gln Ala Gln Leu Leu Gln Phe Thr Ser Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
                260                 265                 270

Val Phe Glu Met Val Ser Leu Phe Val Leu Phe Ser Ile Phe Tyr Lys
            275                 280                 285

Arg Ser Tyr Ser Lys Lys Asn Lys Ser Gly Gly Lys Asp Ser Lys Lys
        290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335

Gly Lys Leu Val Ala Thr Ala Ser Lys Ala Val Lys Arg Lys Gly Thr
                340                 345                 350

Arg Val Thr Gly Ala Met
        355

<210> SEQ ID NO 35
<211> LENGTH: 819
<212> TYPE: DNA
<213> ORGANISM: Thalassiosira pseudonana
<220> FEATURE:
<221> NAME/KEY: CDS
<222> LOCATION: (1)..(819)
<223> OTHER INFORMATION: Delta-6-Elongase

<400> SEQUENCE: 35 atg gac gcc tac aac gct gca atg gat aag atc ggt gcc gcc atc atc      48
Met Asp Ala Tyr Asn Ala Ala Met Asp Lys Ile Gly Ala Ala Ile Ile
  1               5                  10                  15 gat tgg tct gat ccc gat gga aag ttc cgt gcc gat aga gag gac tgg      96
Asp Trp Ser Asp Pro Asp Gly Lys Phe Arg Ala Asp Arg Glu Asp Trp
             20                  25                  30 tgg ctc tgc gac ttc cgt agc gcc atc acc atc gcc ctc atc tac atc     144
Trp Leu Cys Asp Phe Arg Ser Ala Ile Thr Ile Ala Leu Ile Tyr Ile
         35                  40                  45 gcc ttc gtc atc ctc ggt tcc gcc gtc atg caa tcc ctc ccc gca atg     192
Ala Phe Val Ile Leu Gly Ser Ala Val Met Gln Ser Leu Pro Ala Met
     50                  55                  60 gat ccc tac ccc atc aaa ttc ctc tac aac gtc tcc caa atc ttc ctt     240
Asp Pro Tyr Pro Ile Lys Phe Leu Tyr Asn Val Ser Gln Ile Phe Leu
 65                  70                  75                  80 tgt gcc tac atg act gtc gag gcg gga ttt ttg gcc tac cgc aat gga     288
Cys Ala Tyr Met Thr Val Glu Ala Gly Phe Leu Ala Tyr Arg Asn Gly
                 85                  90                  95 tat acc gtc atg cct tgc aat cat ttc aat gtg aat gat cct ccc gtg     336
Tyr Thr Val Met Pro Cys Asn His Phe Asn Val Asn Asp Pro Pro Val
            100                 105                 110 gcg aat ctt ctt tgg ttg ttt tat att tcc aag gtg tgg gac ttt tgg     384
Ala Asn Leu Leu Trp Leu Phe Tyr Ile Ser Lys Val Trp Asp Phe Trp
        115                 120                 125 gat acc att ttc att gtg ttg ggg aag aag tgg cgt caa tta tct ttc     432
Asp Thr Ile Phe Ile Val Leu Gly Lys Lys Trp Arg Gln Leu Ser Phe
    130                 135                 140 ttg cat gta tac cat cac acc acc atc ttt cta ttc tat tgg ctg aat     480
Leu His Val Tyr His His Thr Thr Ile Phe Leu Phe Tyr Trp Leu Asn
```

```
                  145                 150                 155                 160
gcc aat gtc ttg tac gat ggt gac atc ttc ctt acc atc ttg ctc aat      528
Ala Asn Val Leu Tyr Asp Gly Asp Ile Phe Leu Thr Ile Leu Leu Asn
                165                 170                 175 gga ttc atc cac acg gtg atg tac acg tat tac ttc atc tgt atg cat      576
Gly Phe Ile His Thr Val Met Tyr Thr Tyr Tyr Phe Ile Cys Met His
            180                 185                 190 acc aaa gat tcc aag acg ggc aag agt ctt cct ata tgg tgg aag tcg      624
Thr Lys Asp Ser Lys Thr Gly Lys Ser Leu Pro Ile Trp Trp Lys Ser
        195                 200                 205 agt ttg acg gcg ttt cag ttg ttg caa ttc act atc atg atg agt cag      672
Ser Leu Thr Ala Phe Gln Leu Leu Gln Phe Thr Ile Met Met Ser Gln
    210                 215                 220 gct acc tac ctt gtc ttc cac ggg tgt gat aag gtg tcg ctt cgt atc      720
Ala Thr Tyr Leu Val Phe His Gly Cys Asp Lys Val Ser Leu Arg Ile
225                 230                 235                 240 acg att gtg tac ttt gtg tcc ctt ttg agt ttg ttc ttc ctt ttt gct      768
Thr Ile Val Tyr Phe Val Ser Leu Leu Ser Leu Phe Phe Leu Phe Ala
                245                 250                 255 cag ttc ttt gtg caa tca tac atg gca ccc aaa aag aag agt gct          816
Gln Phe Phe Val Gln Ser Tyr Met Ala Pro Lys Lys Lys Ser Ala
            260                 265                 270 tag                                                                  819

<210> SEQ ID NO 36
<211> LENGTH: 272
<212> TYPE: PRT
<213> ORGANISM: Thalassiosira pseudonana

<400> SEQUENCE: 36

Met Asp Ala Tyr Asn Ala Ala Met Asp Lys Ile Gly Ala Ala Ile Ile
 1               5                  10                  15

Asp Trp Ser Asp Pro Asp Gly Lys Phe Arg Ala Asp Arg Glu Asp Trp
                20                  25                  30

Trp Leu Cys Asp Phe Arg Ser Ala Ile Thr Ile Ala Leu Ile Tyr Ile
            35                  40                  45

Ala Phe Val Ile Leu Gly Ser Ala Val Met Gln Ser Leu Pro Ala Met
        50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205
```

```
Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Ser Leu Leu Ser Leu Phe Phe Leu Phe Ala
                245                 250                 255

Gln Phe Phe Val Gln Ser Tyr Met Ala Pro Lys Lys Lys Ser Ala
                260                 265                 270

<210> SEQ ID NO 37
<211> LENGTH: 1455
<212> TYPE: DNA
<213> ORGANISM: Thalassiosira pseudonana
<220> FEATURE:
<221> NAME/KEY: CDS
<222> LOCATION: (1)..(1455)
<223> OTHER INFORMATION: Delta-6-Desaturase

<400> SEQUENCE: 37 atg gga aaa gga gga gac gca gcc gca gct acc aag cgt agt gga gca     48
Met Gly Lys Gly Gly Asp Ala Ala Ala Ala Thr Lys Arg Ser Gly Ala
 1               5                  10                  15 ttg aaa ttg gcg gag aag ccg cag aag tac act tgg cag gag gtg aag     96
Leu Lys Leu Ala Glu Lys Pro Gln Lys Tyr Thr Trp Gln Glu Val Lys
             20                  25                  30 aag cac atc acc ccc gac gat gcc tgg gta gtc cac caa aac aaa gtc    144
Lys His Ile Thr Pro Asp Asp Ala Trp Val Val His Gln Asn Lys Val
         35                  40                  45 tac gac gtc tcc aac tgg tac gac cac ccc ggt gga gcc gtg gtg ttc    192
Tyr Asp Val Ser Asn Trp Tyr Asp His Pro Gly Gly Ala Val Val Phe
     50                  55                  60 acc cac gcc gga gac gac atg acg gac atc ttc gcc gcc ttc cac gcc    240
Thr His Ala Gly Asp Asp Met Thr Asp Ile Phe Ala Ala Phe His Ala
 65                  70                  75                  80 caa ggc tct cag gcc atg atg aag aag ttt tac att gga gat ttg att    288
Gln Gly Ser Gln Ala Met Met Lys Lys Phe Tyr Ile Gly Asp Leu Ile
                 85                  90                  95 ccg gag agt gtg gag cat aag gat caa aga cag ttg gat ttc gag aag    336
Pro Glu Ser Val Glu His Lys Asp Gln Arg Gln Leu Asp Phe Glu Lys
            100                 105                 110 gga tat cgt gat tta cgg gcc aag ctt gtc atg atg ggg atg ttc aag    384
Gly Tyr Arg Asp Leu Arg Ala Lys Leu Val Met Met Gly Met Phe Lys
        115                 120                 125 tcg agt aag atg tat tat gca tac aag tgc tcg ttc aat atg tgc atg    432
Ser Ser Lys Met Tyr Tyr Ala Tyr Lys Cys Ser Phe Asn Met Cys Met
    130                 135                 140 tgg ttg gtg gcg gtg gcc atg gtg tac tac tcg gac agt ttg gca atg    480
Trp Leu Val Ala Val Ala Met Val Tyr Tyr Ser Asp Ser Leu Ala Met
145                 150                 155                 160 cac att gga tcg gct ctc ttg ttg gga ttg ttc tgg cag cag tgt gga    528
His Ile Gly Ser Ala Leu Leu Leu Gly Leu Phe Trp Gln Gln Cys Gly
                165                 170                 175 tgg ctt gcg cac gac ttt ctt cac cac caa gtc ttt aag caa cga aag    576
Trp Leu Ala His Asp Phe Leu His His Gln Val Phe Lys Gln Arg Lys
            180                 185                 190 tac gga gat ctc gtt ggc atc ttt tgg gga gat ctc atg cag ggg ttc    624
Tyr Gly Asp Leu Val Gly Ile Phe Trp Gly Asp Leu Met Gln Gly Phe
        195                 200                 205 tcg atg cag tgg tgg aag aac aag cac aat ggc cac cat gct gtt ccc    672
Ser Met Gln Trp Trp Lys Asn Lys His Asn Gly His His Ala Val Pro
    210                 215                 220
```

```
aac ttg cac aac tct tcc ttg gac agt cag gat ggt gat ccc gat att      720
Asn Leu His Asn Ser Ser Leu Asp Ser Gln Asp Gly Asp Pro Asp Ile
225                 230                 235                 240 gat acc atg cca ctc ctt gct tgg agt ctc aag cag gct cag agt ttc      768
Asp Thr Met Pro Leu Leu Ala Trp Ser Leu Lys Gln Ala Gln Ser Phe
                245                 250                 255 aga gag atc aat aag gga aag gac agt acc ttc gtc aag tac gct atc      816
Arg Glu Ile Asn Lys Gly Lys Asp Ser Thr Phe Val Lys Tyr Ala Ile
            260                 265                 270 aaa ttc cag gca ttc aca tac ttc ccc atc ctc ctg gct cgc atc          864
Lys Phe Gln Ala Phe Thr Tyr Phe Pro Ile Leu Leu Ala Arg Ile
        275                 280                 285 tct tgg ttg aat gaa tcc ttc aaa act gca ttc gga ctc gga gct gcc      912
Ser Trp Leu Asn Glu Ser Phe Lys Thr Ala Phe Gly Leu Gly Ala Ala
290                 295                 300 tcg gag aat gcc aag ttg gag ttg gag aag cgt gga ctt cag tac cca      960
Ser Glu Asn Ala Lys Leu Glu Leu Glu Lys Arg Gly Leu Gln Tyr Pro
305                 310                 315                 320 ctt ttg gag aag ctt gga atc acc ctt cat tac act tgg atg ttc gtc     1008
Leu Leu Glu Lys Leu Gly Ile Thr Leu His Tyr Thr Trp Met Phe Val
                325                 330                 335 ctc tct tcc gga ttt gga agg tgg tct ctt cca tat tcc atc atg tat     1056
Leu Ser Ser Gly Phe Gly Arg Trp Ser Leu Pro Tyr Ser Ile Met Tyr
            340                 345                 350 ttc ttc act gcc aca tgc tcc tcg gga ctt ttc ctc gca ttg gtc ttt     1104
Phe Phe Thr Ala Thr Cys Ser Ser Gly Leu Phe Leu Ala Leu Val Phe
        355                 360                 365 gga ttg gga cac aac ggt atg tca gtg tac gat gcc acc acc cga cct     1152
Gly Leu Gly His Asn Gly Met Ser Val Tyr Asp Ala Thr Thr Arg Pro
    370                 375                 380 gac ttc tgg caa ctc caa gtc acc act aca cgt aac atc att ggt gga     1200
Asp Phe Trp Gln Leu Gln Val Thr Thr Thr Arg Asn Ile Ile Gly Gly
385                 390                 395                 400 cac ggc att ccc caa ttc ttt gtg gat tgg ttc tgc ggt gga ttg caa     1248
His Gly Ile Pro Gln Phe Phe Val Asp Trp Phe Cys Gly Gly Leu Gln
                405                 410                 415 tac caa gtg gat cac cac ctc ttc ccc atg atg cct aga aac aat atc     1296
Tyr Gln Val Asp His His Leu Phe Pro Met Met Pro Arg Asn Asn Ile
            420                 425                 430 gcg aaa tgc cac aag ctt gtg gag tca ttc tgt aag gag tgg ggt gtg     1344
Ala Lys Cys His Lys Leu Val Glu Ser Phe Cys Lys Glu Trp Gly Val
        435                 440                 445 aag tac cat gag gcc gat atg tgg gat ggt acc gtg gaa gtg ttg caa     1392
Lys Tyr His Glu Ala Asp Met Trp Asp Gly Thr Val Glu Val Leu Gln
    450                 455                 460 cat ctc tcc aag gtg tcg gat gat ttc ctt gtg gag atg gtg aag gat     1440
His Leu Ser Lys Val Ser Asp Asp Phe Leu Val Glu Met Val Lys Asp
465                 470                 475                 480 ttc cct gcc atg taa                                                 1455
Phe Pro Ala Met <210> SEQ ID NO 38
<211> LENGTH: 484
<212> TYPE: PRT
<213> ORGANISM: Thalassiosira pseudonana

<400> SEQUENCE: 38

Met Gly Lys Gly Gly Asp Ala Ala Ala Ala Thr Lys Arg Ser Gly Ala
1               5                   10                  15
```

```
Leu Lys Leu Ala Glu Lys Pro Gln Lys Tyr Thr Trp Gln Glu Val Lys
             20                  25                  30

Lys His Ile Thr Pro Asp Asp Ala Trp Val His Gln Asn Lys Val
         35                  40                  45

Tyr Asp Val Ser Asn Trp Tyr Asp His Pro Gly Gly Ala Val Val Phe
     50                  55                  60

Thr His Ala Gly Asp Asp Met Thr Asp Ile Phe Ala Ala Phe His Ala
 65                  70                  75                  80

Gln Gly Ser Gln Ala Met Met Lys Lys Phe Tyr Ile Gly Asp Leu Ile
                 85                  90                  95

Pro Glu Ser Val Glu His Lys Asp Gln Arg Gln Leu Asp Phe Glu Lys
             100                 105                 110

Gly Tyr Arg Asp Leu Arg Ala Lys Leu Val Met Met Gly Met Phe Lys
         115                 120                 125

Ser Ser Lys Met Tyr Tyr Ala Tyr Lys Cys Ser Phe Asn Met Cys Met
     130                 135                 140

Trp Leu Val Ala Val Ala Met Val Tyr Ser Asp Ser Leu Ala Met
145                 150                 155                 160

His Ile Gly Ser Ala Leu Leu Leu Gly Leu Phe Trp Gln Gln Cys Gly
                 165                 170                 175

Trp Leu Ala His Asp Phe Leu His His Gln Val Phe Lys Gln Arg Lys
             180                 185                 190

Tyr Gly Asp Leu Val Gly Ile Phe Trp Gly Asp Leu Met Gln Gly Phe
         195                 200                 205

Ser Met Gln Trp Trp Lys Asn Lys His Asn Gly His His Ala Val Pro
     210                 215                 220

Asn Leu His Asn Ser Ser Leu Asp Ser Gln Asp Gly Asp Pro Asp Ile
225                 230                 235                 240

Asp Thr Met Pro Leu Leu Ala Trp Ser Leu Lys Gln Ala Gln Ser Phe
                 245                 250                 255

Arg Glu Ile Asn Lys Gly Lys Asp Ser Thr Phe Val Lys Tyr Ala Ile
             260                 265                 270

Lys Phe Gln Ala Phe Thr Tyr Phe Pro Ile Leu Leu Leu Ala Arg Ile
         275                 280                 285

Ser Trp Leu Asn Glu Ser Phe Lys Thr Ala Phe Gly Leu Gly Ala Ala
     290                 295                 300

Ser Glu Asn Ala Lys Leu Glu Leu Glu Lys Arg Gly Leu Gln Tyr Pro
305                 310                 315                 320

Leu Leu Glu Lys Leu Gly Ile Thr Leu His Tyr Thr Trp Met Phe Val
                 325                 330                 335

Leu Ser Ser Gly Phe Gly Arg Trp Ser Leu Pro Tyr Ser Ile Met Tyr
             340                 345                 350

Phe Phe Thr Ala Thr Cys Ser Ser Gly Leu Phe Leu Ala Leu Val Phe
         355                 360                 365

Gly Leu Gly His Asn Gly Met Ser Val Tyr Asp Ala Thr Thr Arg Pro
     370                 375                 380

Asp Phe Trp Gln Leu Gln Val Thr Thr Thr Arg Asn Ile Ile Gly Gly
385                 390                 395                 400

His Gly Ile Pro Gln Phe Phe Val Asp Trp Phe Cys Gly Gly Leu Gln
                 405                 410                 415

Tyr Gln Val Asp His His Leu Phe Pro Met Met Pro Arg Asn Asn Ile
             420                 425                 430

Ala Lys Cys His Lys Leu Val Glu Ser Phe Cys Lys Glu Trp Gly Val
```

-continued

```
              435                 440                 445
Lys Tyr His Glu Ala Asp Met Trp Asp Gly Thr Val Glu Val Leu Gln
    450                 455                 460

His Leu Ser Lys Val Ser Asp Asp Phe Leu Val Glu Met Val Lys Asp
465                 470                 475                 480

Phe Pro Ala Met

<210> SEQ ID NO 39
<211> LENGTH: 1449
<212> TYPE: DNA
<213> ORGANISM: Thalassiosira pseudonana
<220> FEATURE:
<221> NAME/KEY: CDS
<222> LOCATION: (1)..(1449)
<223> OTHER INFORMATION: Delta-5-Desaturase

<400> SEQUENCE: 39 atg cca ccc aac gcc gag gtc aaa aac ctc cgt tca cgt tcc atc cca        48
Met Pro Pro Asn Ala Glu Val Lys Asn Leu Arg Ser Arg Ser Ile Pro
  1               5                  10                  15 acg aag aag tcc agt tca tcg tca tcc acc gcg aac gac gat ccg gct        96
Thr Lys Lys Ser Ser Ser Ser Ser Thr Ala Asn Asp Asp Pro Ala
             20                  25                  30 acc caa tcc acc tca cct gtg aac cga acc ctc aag tct ttg aat gga       144
Thr Gln Ser Thr Ser Pro Val Asn Arg Thr Leu Lys Ser Leu Asn Gly
         35                  40                  45 aac gaa ata gct att gac ggt gtc atc tat gat att gat ggc ttt gtc       192
Asn Glu Ile Ala Ile Asp Gly Val Ile Tyr Asp Ile Asp Gly Phe Val
     50                  55                  60 cat cct gga gga gag gtt att agc ttc ttt gga ggc aac gat gtg act       240
His Pro Gly Gly Glu Val Ile Ser Phe Phe Gly Gly Asn Asp Val Thr
 65                  70                  75                  80 gta cag tac aaa atg att cat ccg tat cat aat agt aag cat ctc gag       288
Val Gln Tyr Lys Met Ile His Pro Tyr His Asn Ser Lys His Leu Glu
                 85                  90                  95 aag atg aga gcc gtt gga aag att gca gac tac tcc aca gag tac aag       336
Lys Met Arg Ala Val Gly Lys Ile Ala Asp Tyr Ser Thr Glu Tyr Lys
            100                 105                 110 ttc gac aca ccc ttt gaa cga gag atc aaa tcc gaa gtg ttc aaa atc       384
Phe Asp Thr Pro Phe Glu Arg Glu Ile Lys Ser Glu Val Phe Lys Ile
        115                 120                 125 gtc cgt cga gga cgt gaa ttc ggt aca aca gga tat ttc ctc cgt gcc       432
Val Arg Arg Gly Arg Glu Phe Gly Thr Thr Gly Tyr Phe Leu Arg Ala
    130                 135                 140 ttc ttc tac att gct ctc ttc ttc acc atg caa tac acc ttc gcc aca       480
Phe Phe Tyr Ile Ala Leu Phe Phe Thr Met Gln Tyr Thr Phe Ala Thr
145                 150                 155                 160 tgc act acc ttc acc acc tac gat cat tgg tat caa agt ggt gta ttc       528
Cys Thr Thr Phe Thr Thr Tyr Asp His Trp Tyr Gln Ser Gly Val Phe
                165                 170                 175 atc gcc att gtg ttt ggt atc tca caa gct ttc att ggg ttg aat gta       576
Ile Ala Ile Val Phe Gly Ile Ser Gln Ala Phe Ile Gly Leu Asn Val
            180                 185                 190 caa cat gat gcc aat cac gga gct gct agc aaa cga cct tgg gtg aat       624
Gln His Asp Ala Asn His Gly Ala Ala Ser Lys Arg Pro Trp Val Asn
        195                 200                 205 gat ctc ctt gga tct gga gct gat ctc atc ggt gga tgc aaa tgg aac       672
Asp Leu Leu Gly Ser Gly Ala Asp Leu Ile Gly Gly Cys Lys Trp Asn
    210                 215                 220 tgg ttg gct cag cat tgg act cat cat gcg tat acc aat cac gct gat       720
```

```
Trp Leu Ala Gln His Trp Thr His His Ala Tyr Thr Asn His Ala Asp
225                 230                 235                 240 aaa gat cct gat agc ttt agt tcc gag ccg gtc ttc aac ttt aac gat      768
Lys Asp Pro Asp Ser Phe Ser Ser Glu Pro Val Phe Asn Phe Asn Asp
                    245                 250                 255 tat ccc att ggt cac ccc aaa aga aag tgg tgg cat agg ttc caa ggg      816
Tyr Pro Ile Gly His Pro Lys Arg Lys Trp Trp His Arg Phe Gln Gly
                260                 265                 270 ctc tac ttc cta atc atg ctg agt ttc tat tgg gta tcg atg gta ttc      864
Leu Tyr Phe Leu Ile Met Leu Ser Phe Tyr Trp Val Ser Met Val Phe
            275                 280                 285 aac cca caa gtt atc gac ctc cgt cat gct gga gct gcc tac gtt gga      912
Asn Pro Gln Val Ile Asp Leu Arg His Ala Gly Ala Ala Tyr Val Gly
        290                 295                 300 ttt cag atg gag aac gac ttt atc gtc aaa cgg aga aag tat gca atg      960
Phe Gln Met Glu Asn Asp Phe Ile Val Lys Arg Arg Lys Tyr Ala Met
305                 310                 315                 320 gca ctt cgt gca atg tac ttc tat ttc aac atc tat tgt ccg att gtc     1008
Ala Leu Arg Ala Met Tyr Phe Tyr Phe Asn Ile Tyr Cys Pro Ile Val
                    325                 330                 335 aac aat gga ttg act tgg tcg aca gtt gga atc atc ctc tta atg gga     1056
Asn Asn Gly Leu Thr Trp Ser Thr Val Gly Ile Ile Leu Leu Met Gly
                340                 345                 350 gtt agc gaa agc ttc atg ctc tcc ggt cta ttc gta ctc tca cac aac     1104
Val Ser Glu Ser Phe Met Leu Ser Gly Leu Phe Val Leu Ser His Asn
            355                 360                 365 ttt gaa aat tcc gaa cgt gat cct acc tct gag tat cgc aag act ggt     1152
Phe Glu Asn Ser Glu Arg Asp Pro Thr Ser Glu Tyr Arg Lys Thr Gly
        370                 375                 380 gag caa gta tgt tgg ttc aag tct caa gtg gag act tct tct acc tac     1200
Glu Gln Val Cys Trp Phe Lys Ser Gln Val Glu Thr Ser Ser Thr Tyr
385                 390                 395                 400 gga ggt atc gtt gct ggg tgt ctc act ggt gga ctc aac ttt caa gtg     1248
Gly Gly Ile Val Ala Gly Cys Leu Thr Gly Gly Leu Asn Phe Gln Val
                    405                 410                 415 gag cat cat ttg ttc ccg agg atg agc agt gct tgg tat cct ttc atc     1296
Glu His His Leu Phe Pro Arg Met Ser Ser Ala Trp Tyr Pro Phe Ile
                420                 425                 430 gcg ccg aag gtt aga gag att tgt aag aag cat gga gtt aga tac gct     1344
Ala Pro Lys Val Arg Glu Ile Cys Lys Lys His Gly Val Arg Tyr Ala
            435                 440                 445 tac tat ccg tac atc tgg cag aac ttg cat tct acc gtg agt tac atg     1392
Tyr Tyr Pro Tyr Ile Trp Gln Asn Leu His Ser Thr Val Ser Tyr Met
        450                 455                 460 cat ggg acg gga acg gga gct aga tgg gag ctt cag ccg ttg tct gga     1440
His Gly Thr Gly Thr Gly Ala Arg Trp Glu Leu Gln Pro Leu Ser Gly
465                 470                 475                 480 agg gcg tag                                                         1449
Arg Ala <210> SEQ ID NO 40
<211> LENGTH: 482
<212> TYPE: PRT
<213> ORGANISM: Thalassiosira pseudonana

<400> SEQUENCE: 40

Met Pro Pro Asn Ala Glu Val Lys Asn Leu Arg Ser Arg Ser Ile Pro
1               5                   10                  15

Thr Lys Lys Ser Ser Ser Ser Ser Thr Ala Asn Asp Asp Pro Ala
            20                  25                  30
```

```
Thr Gln Ser Thr Ser Pro Val Asn Arg Thr Leu Lys Ser Leu Asn Gly
         35                  40                  45

Asn Glu Ile Ala Ile Asp Gly Val Ile Tyr Asp Ile Asp Gly Phe Val
     50                  55                  60

His Pro Gly Gly Glu Val Ile Ser Phe Gly Gly Asn Asp Val Thr
 65                  70                  75                  80

Val Gln Tyr Lys Met Ile His Pro Tyr His Asn Ser Lys His Leu Glu
             85                  90                  95

Lys Met Arg Ala Val Gly Lys Ile Ala Asp Tyr Ser Thr Glu Tyr Lys
             100                 105                 110

Phe Asp Thr Pro Phe Glu Arg Glu Ile Lys Ser Glu Val Phe Lys Ile
             115                 120                 125

Val Arg Arg Gly Arg Glu Phe Gly Thr Thr Gly Tyr Phe Leu Arg Ala
         130                 135                 140

Phe Phe Tyr Ile Ala Leu Phe Phe Thr Met Gln Tyr Thr Phe Ala Thr
145                 150                 155                 160

Cys Thr Thr Phe Thr Thr Tyr Asp His Trp Tyr Gln Ser Gly Val Phe
                 165                 170                 175

Ile Ala Ile Val Phe Gly Ile Ser Gln Ala Phe Ile Gly Leu Asn Val
             180                 185                 190

Gln His Asp Ala Asn His Gly Ala Ala Ser Lys Arg Pro Trp Val Asn
         195                 200                 205

Asp Leu Leu Gly Ser Gly Ala Asp Leu Ile Gly Gly Cys Lys Trp Asn
         210                 215                 220

Trp Leu Ala Gln His Trp Thr His Ala Tyr Thr Asn His Ala Asp
225                 230                 235                 240

Lys Asp Pro Asp Ser Phe Ser Ser Glu Pro Val Phe Asn Phe Asn Asp
                 245                 250                 255

Tyr Pro Ile Gly His Pro Lys Arg Lys Trp His Arg Phe Gln Gly
             260                 265                 270

Leu Tyr Phe Leu Ile Met Leu Ser Phe Tyr Trp Val Ser Met Val Phe
         275                 280                 285

Asn Pro Gln Val Ile Asp Leu Arg His Ala Gly Ala Ala Tyr Val Gly
         290                 295                 300

Phe Gln Met Glu Asn Asp Phe Ile Val Lys Arg Arg Lys Tyr Ala Met
305                 310                 315                 320

Ala Leu Arg Ala Met Tyr Phe Tyr Phe Asn Ile Tyr Cys Pro Ile Val
                 325                 330                 335

Asn Asn Gly Leu Thr Trp Ser Thr Val Gly Ile Ile Leu Leu Met Gly
             340                 345                 350

Val Ser Glu Ser Phe Met Leu Ser Gly Leu Phe Val Leu Ser His Asn
         355                 360                 365

Phe Glu Asn Ser Glu Arg Asp Pro Thr Ser Glu Tyr Arg Lys Thr Gly
     370                 375                 380

Glu Gln Val Cys Trp Phe Lys Ser Gln Val Glu Thr Ser Ser Thr Tyr
385                 390                 395                 400

Gly Gly Ile Val Ala Gly Cys Leu Thr Gly Gly Leu Asn Phe Gln Val
                 405                 410                 415

Glu His His Leu Phe Pro Arg Met Ser Ser Ala Trp Tyr Pro Phe Ile
             420                 425                 430

Ala Pro Lys Val Arg Glu Ile Cys Lys Lys His Gly Val Arg Tyr Ala
             435                 440                 445
```

```
                                Tyr Tyr Pro Tyr Ile Trp Gln Asn Leu His Ser Thr Val Ser Tyr Met
                                    450             455                 460

His Gly Thr Gly Thr Gly Ala Arg Trp Glu Leu Gln Pro Leu Ser Gly
                                465             470                 475                 480

Arg Ala

<210> SEQ ID NO 41
<211> LENGTH: 1512
<212> TYPE: DNA
<213> ORGANISM: Thalassiosira pseudonana
<220> FEATURE:
<221> NAME/KEY: CDS
<222> LOCATION: (1)..(1512)
<223> OTHER INFORMATION: Delta-4-Desaturase

<400> SEQUENCE: 41 atg tgc aac ggc aac ctc cca gca tcc acc gca cag ctc aag tcc acc        48
Met Cys Asn Gly Asn Leu Pro Ala Ser Thr Ala Gln Leu Lys Ser Thr
  1               5                  10                  15 tcg aag ccc cag cag caa cat gag cat cgc acc atc tcc aag tcc gag        96
Ser Lys Pro Gln Gln Gln His Glu His Arg Thr Ile Ser Lys Ser Glu
                 20                  25                  30 ctc gcc caa cac aac acg ccc aaa tca gca tgg tgt gcc gtc cac tcc       144
Leu Ala Gln His Asn Thr Pro Lys Ser Ala Trp Cys Ala Val His Ser
             35                  40                  45 act ccc gcc acc gac cca tcc cac tcc aac aac aaa caa cac gca cac       192
Thr Pro Ala Thr Asp Pro Ser His Ser Asn Asn Lys Gln His Ala His
         50                  55                  60 cta gtc ctc gac att acc gac ttt gcg tcc cgc cat cca ggg gga gac       240
Leu Val Leu Asp Ile Thr Asp Phe Ala Ser Arg His Pro Gly Gly Asp
 65                  70                  75                  80 ctc atc ctc ctc gct tcc ggc aaa gac gcc tcg gtg ctg ttt gaa aca       288
Leu Ile Leu Leu Ala Ser Gly Lys Asp Ala Ser Val Leu Phe Glu Thr
                 85                  90                  95 tac cat cca cgt gga gtt ccg acg tct ctc att caa aag ctg cag att       336
Tyr His Pro Arg Gly Val Pro Thr Ser Leu Ile Gln Lys Leu Gln Ile
                100                 105                 110 gga gtg atg gag gag gag gcg ttt cgg gat tcg ttt tac agt tgg act       384
Gly Val Met Glu Glu Glu Ala Phe Arg Asp Ser Phe Tyr Ser Trp Thr
            115                 120                 125 gat tct gac ttt tat act gtg ttg aag agg agg gtt gtg gag cgg ttg       432
Asp Ser Asp Phe Tyr Thr Val Leu Lys Arg Arg Val Val Glu Arg Leu
        130                 135                 140 gag gag agg ggg ttg gac agg agg gga tcg aaa gag att tgg atc aag       480
Glu Glu Arg Gly Leu Asp Arg Arg Gly Ser Lys Glu Ile Trp Ile Lys
145                 150                 155                 160 gct ttg ttc ttg ttg gtt gga ttt tgg tac tgt ttg tac aag atg tat       528
Ala Leu Phe Leu Leu Val Gly Phe Trp Tyr Cys Leu Tyr Lys Met Tyr
                165                 170                 175 act acg tcg gat atc gat cag tac ggt att gcc att gcc tat tct att       576
Thr Thr Ser Asp Ile Asp Gln Tyr Gly Ile Ala Ile Ala Tyr Ser Ile
            180                 185                 190 gga atg gga acc ttt gcg gca ttc atc ggc acg tgt att caa cac gat       624
Gly Met Gly Thr Phe Ala Ala Phe Ile Gly Thr Cys Ile Gln His Asp
        195                 200                 205 gga aat cac ggt gca ttc gct cag aac aag tta ctc aac aag ttg gct       672
Gly Asn His Gly Ala Phe Ala Gln Asn Lys Leu Leu Asn Lys Leu Ala
    210                 215                 220 ggg tgg acg ttg gat atg att ggt gcg agt gcg ttt acg tgg gag ctt       720
Gly Trp Thr Leu Asp Met Ile Gly Ala Ser Ala Phe Thr Trp Glu Leu
225                 230                 235                 240
```

```
cag cac atg ctg ggg cat cat cca tat acg aat gtg ttg gat ggg gtg         768
Gln His Met Leu Gly His His Pro Tyr Thr Asn Val Leu Asp Gly Val
            245                 250                 255 gag gag gag agg aag gag agg ggg gag gat gtt gct ttg gaa gaa aag         816
Glu Glu Glu Arg Lys Glu Arg Gly Glu Asp Val Ala Leu Glu Glu Lys
        260                 265                 270 gat cag gat ttt gaa gtt gcc aca tcc gga cga tta tat cat att gat         864
Asp Gln Asp Phe Glu Val Ala Thr Ser Gly Arg Leu Tyr His Ile Asp
    275                 280                 285 gcc aat gta cgt tat ggt tcg gta tgg aat gtc atg agg ttt tgg gct         912
Ala Asn Val Arg Tyr Gly Ser Val Trp Asn Val Met Arg Phe Trp Ala
290                 295                 300 atg aag gtc att acg atg gga tat atg atg gga tta cca atc tac ttt         960
Met Lys Val Ile Thr Met Gly Tyr Met Met Gly Leu Pro Ile Tyr Phe
305                 310                 315                 320 cat gga gta ctg agg gga gtt gga ttg ttt gtt att ggg cat ttg gcg        1008
His Gly Val Leu Arg Gly Val Gly Leu Phe Val Ile Gly His Leu Ala
                325                 330                 335 tgt gga gag ttg ttg gcg acg atg ttt att gtg aat cac gtc att gag        1056
Cys Gly Glu Leu Leu Ala Thr Met Phe Ile Val Asn His Val Ile Glu
            340                 345                 350 ggt gtg agt tat gga acg aag gat ttg gtt ggt ggt gcg agt cat gta        1104
Gly Val Ser Tyr Gly Thr Lys Asp Leu Val Gly Gly Ala Ser His Val
        355                 360                 365 gat gag aag aag att gtc aag cca acg act gta ttg gga gat aca cca        1152
Asp Glu Lys Lys Ile Val Lys Pro Thr Thr Val Leu Gly Asp Thr Pro
    370                 375                 380 atg gta aag act cgc gag gag gca ttg aaa agc aac agc aat aac aac        1200
Met Val Lys Thr Arg Glu Glu Ala Leu Lys Ser Asn Ser Asn Asn Asn
385                 390                 395                 400 aag aag aag gga gag aag aac tcg gta cca tcc gtt cca ttc aac gac        1248
Lys Lys Lys Gly Glu Lys Asn Ser Val Pro Ser Val Pro Phe Asn Asp
                405                 410                 415 tgg gca gca gtc caa tgc cag acc tcc gtg aat tgg tct cca ggc tca        1296
Trp Ala Ala Val Gln Cys Gln Thr Ser Val Asn Trp Ser Pro Gly Ser
            420                 425                 430 tgg ttc tgg aat cac ttt tct ggg gga ctc tct cat cag att gag cat        1344
Trp Phe Trp Asn His Phe Ser Gly Gly Leu Ser His Gln Ile Glu His
        435                 440                 445 cac ttg ttc ccc agc att tgt cat aca aac tac tgt cat atc cag gat        1392
His Leu Phe Pro Ser Ile Cys His Thr Asn Tyr Cys His Ile Gln Asp
    450                 455                 460 gtt gtg gag agt acg tgt gct gag tac gga gtt ccg tat cag agt gag        1440
Val Val Glu Ser Thr Cys Ala Glu Tyr Gly Val Pro Tyr Gln Ser Glu
465                 470                 475                 480 agt aat ttg ttt gtt gct tat gga aag atg att agt cat ttg aag ttt        1488
Ser Asn Leu Phe Val Ala Tyr Gly Lys Met Ile Ser His Leu Lys Phe
                485                 490                 495 ttg ggt aaa gcc aag tgt gag tag                                         1512
Leu Gly Lys Ala Lys Cys Glu
            500
```

<210> SEQ ID NO 42
<211> LENGTH: 503
<212> TYPE: PRT
<213> ORGANISM: Thalassiosira pseudonana

<400> SEQUENCE: 42

```
Met Cys Asn Gly Asn Leu Pro Ala Ser Thr Ala Gln Leu Lys Ser Thr
  1               5                  10                  15
```

```
Ser Lys Pro Gln Gln Gln His Glu His Arg Thr Ile Ser Lys Ser Glu
             20                  25                  30

Leu Ala Gln His Asn Thr Pro Lys Ser Ala Trp Cys Ala Val His Ser
         35                  40                  45

Thr Pro Ala Thr Asp Pro Ser His Ser Asn Asn Lys Gln His Ala His
 50                  55                  60

Leu Val Leu Asp Ile Thr Asp Phe Ala Ser Arg His Pro Gly Gly Asp
 65                  70                  75                  80

Leu Ile Leu Leu Ala Ser Gly Lys Asp Ala Ser Val Leu Phe Glu Thr
             85                  90                  95

Tyr His Pro Arg Gly Val Pro Thr Ser Leu Ile Gln Lys Leu Gln Ile
             100                 105                 110

Gly Val Met Glu Glu Ala Phe Arg Asp Ser Phe Tyr Ser Trp Thr
             115                 120                 125

Asp Ser Asp Phe Tyr Thr Val Leu Lys Arg Arg Val Val Glu Arg Leu
 130                 135                 140

Glu Glu Arg Gly Leu Asp Arg Arg Gly Ser Lys Glu Ile Trp Ile Lys
 145                 150                 155                 160

Ala Leu Phe Leu Leu Val Gly Phe Trp Tyr Cys Leu Tyr Lys Met Tyr
             165                 170                 175

Thr Thr Ser Asp Ile Asp Gln Tyr Gly Ile Ala Ile Ala Tyr Ser Ile
             180                 185                 190

Gly Met Gly Thr Phe Ala Ala Phe Ile Gly Thr Cys Ile Gln His Asp
             195                 200                 205

Gly Asn His Gly Ala Phe Ala Gln Asn Lys Leu Leu Asn Lys Leu Ala
             210                 215                 220

Gly Trp Thr Leu Asp Met Ile Gly Ala Ser Ala Phe Thr Trp Glu Leu
225                 230                 235                 240

Gln His Met Leu Gly His His Pro Tyr Thr Asn Val Leu Asp Gly Val
             245                 250                 255

Glu Glu Glu Arg Lys Glu Arg Gly Glu Asp Val Ala Leu Glu Glu Lys
             260                 265                 270

Asp Gln Asp Phe Glu Val Ala Thr Ser Gly Arg Leu Tyr His Ile Asp
             275                 280                 285

Ala Asn Val Arg Tyr Gly Ser Val Trp Asn Val Met Arg Phe Trp Ala
             290                 295                 300

Met Lys Val Ile Thr Met Gly Tyr Met Met Gly Leu Pro Ile Tyr Phe
305                 310                 315                 320

His Gly Val Leu Arg Gly Val Gly Leu Phe Val Ile Gly His Leu Ala
             325                 330                 335

Cys Gly Glu Leu Leu Ala Thr Met Phe Ile Val Asn His Val Ile Glu
             340                 345                 350

Gly Val Ser Tyr Gly Thr Lys Asp Leu Val Gly Gly Ala Ser His Val
             355                 360                 365

Asp Glu Lys Lys Ile Val Lys Pro Thr Thr Val Leu Gly Asp Thr Pro
             370                 375                 380

Met Val Lys Thr Arg Glu Glu Ala Leu Lys Ser Asn Ser Asn Asn
385                 390                 395                 400

Lys Lys Lys Gly Glu Lys Asn Ser Val Pro Ser Val Pro Phe Asn Asp
             405                 410                 415

Trp Ala Ala Val Gln Cys Gln Thr Ser Val Asn Trp Ser Pro Gly Ser
             420                 425                 430
```

```
Trp Phe Trp Asn His Phe Ser Gly Gly Leu Ser His Gln Ile Glu His
        435                 440                 445
His Leu Phe Pro Ser Ile Cys His Thr Asn Tyr Cys His Ile Gln Asp
    450                 455                 460
Val Val Glu Ser Thr Cys Ala Glu Tyr Gly Val Pro Tyr Gln Ser Glu
465                 470                 475                 480
Ser Asn Leu Phe Val Ala Tyr Gly Lys Met Ile Ser His Leu Lys Phe
                485                 490                 495
Leu Gly Lys Ala Lys Cys Glu
            500

<210> SEQ ID NO 43
<211> LENGTH: 1305
<212> TYPE: DNA
<213> ORGANISM: Thalassiosira pseudonana
<220> FEATURE:
<221> NAME/KEY: CDS
<222> LOCATION: (1)..(1305)
<223> OTHER INFORMATION: Delta-12-Desaturase

<400> SEQUENCE: 43 atg gga aag gga gga aga tca gta acc cgc gct caa aca gca gaa aag       48
Met Gly Lys Gly Gly Arg Ser Val Thr Arg Ala Gln Thr Ala Glu Lys
 1               5                  10                  15 tca gca cac acc atc caa acc ttc acc gac ggc cga tgg gtc tcc ccc       96
Ser Ala His Thr Ile Gln Thr Phe Thr Asp Gly Arg Trp Val Ser Pro
                20                  25                  30 tac aac ccc ctc gca aaa gat gca cct gaa ctc ccc tcc aag ggt gaa      144
Tyr Asn Pro Leu Ala Lys Asp Ala Pro Glu Leu Pro Ser Lys Gly Glu
            35                  40                  45 atc aag gcg gtc atc ccc aaa gag tgc ttc gaa cga agc tac ctc cac      192
Ile Lys Ala Val Ile Pro Lys Glu Cys Phe Glu Arg Ser Tyr Leu His
        50                  55                  60 tcc atg tac ttc gtc ctc cgt gac acc gtc atg gcc gtg gcc tgc gcc      240
Ser Met Tyr Phe Val Leu Arg Asp Thr Val Met Ala Val Ala Cys Ala
 65                  70                  75                  80 tac atc gcc cac tca acg ctc tcc acc gat att ccc tcc gag tta ctg      288
Tyr Ile Ala His Ser Thr Leu Ser Thr Asp Ile Pro Ser Glu Leu Leu
                85                  90                  95 agc gtg gac gca ctc aaa tgg ttc ctc gga tgg aac acc tac gcc ttt      336
Ser Val Asp Ala Leu Lys Trp Phe Leu Gly Trp Asn Thr Tyr Ala Phe
            100                 105                 110 tgg atg ggg tgc att ctc acc gga cac tgg gtc cta gcc cat gaa tgt      384
Trp Met Gly Cys Ile Leu Thr Gly His Trp Val Leu Ala His Glu Cys
        115                 120                 125 gga cat ggt gca ttc tct ccc tct cag acg ttt aat gac ttt tgg ggg      432
Gly His Gly Ala Phe Ser Pro Ser Gln Thr Phe Asn Asp Phe Trp Gly
    130                 135                 140 ttc att atg cat cag gcg gtg ttg gtt ccg tat ttc gcc tgg cag tac      480
Phe Ile Met His Gln Ala Val Leu Val Pro Tyr Phe Ala Trp Gln Tyr
145                 150                 155                 160 tct cat gcg aag cat cat cga cgt acc aac aac att atg gat ggg gag      528
Ser His Ala Lys His His Arg Arg Thr Asn Asn Ile Met Asp Gly Glu
                165                 170                 175 agc cat gtg ccc aat atc gcc aag gaa atg gga ttg aac gag aag aat      576
Ser His Val Pro Asn Ile Ala Lys Glu Met Gly Leu Asn Glu Lys Asn
            180                 185                 190 gag cgc agt gga gga tat gcc gcc att cat gag gct att gga gat gga      624
Glu Arg Ser Gly Gly Tyr Ala Ala Ile His Glu Ala Ile Gly Asp Gly
        195                 200                 205
```

```
ccc ttt gcg atg ttt caa atc ttt gct cac ttg gtg atc ggg tgg cct      672
Pro Phe Ala Met Phe Gln Ile Phe Ala His Leu Val Ile Gly Trp Pro
    210                 215                 220 att tac ttg atg gga ttt gct tcc act gga cgt ctc ggt cag gat ggg      720
Ile Tyr Leu Met Gly Phe Ala Ser Thr Gly Arg Leu Gly Gln Asp Gly
225                 230                 235                 240 aag gaa ctt cag gct gga gag atc atc gac cat tac cgt cct tgg agt      768
Lys Glu Leu Gln Ala Gly Glu Ile Ile Asp His Tyr Arg Pro Trp Ser
                245                 250                 255 aag atg ttc ccc acc aag ttg cga ttc aaa att gct ctt tcg aca ctt      816
Lys Met Phe Pro Thr Lys Leu Arg Phe Lys Ile Ala Leu Ser Thr Leu
    260                 265                 270 gga gtg att gcc gcc tgg gtt ggg ttg tac ttt gct gca caa gag tat      864
Gly Val Ile Ala Ala Trp Val Gly Leu Tyr Phe Ala Ala Gln Glu Tyr
                275                 280                 285 gga gtc ttg ccc gtg gtt ctt tgg tac att ggc cca ctc atg tgg aat      912
Gly Val Leu Pro Val Val Leu Trp Tyr Ile Gly Pro Leu Met Trp Asn
290                 295                 300 cag gcg tgg ctt gtg ctc tac act tgg ctt cag cac aat gat ccc tcc      960
Gln Ala Trp Leu Val Leu Tyr Thr Trp Leu Gln His Asn Asp Pro Ser
305                 310                 315                 320 gtg cct caa tat gga agt gac gaa tgg aca tgg gtc aag gga gct ttg     1008
Val Pro Gln Tyr Gly Ser Asp Glu Trp Thr Trp Val Lys Gly Ala Leu
                325                 330                 335 tcg acg att gat cgc ccg tat ggt atc ttt gac ttc ttc cat cac aag     1056
Ser Thr Ile Asp Arg Pro Tyr Gly Ile Phe Asp Phe Phe His His Lys
    340                 345                 350 att gga agc act cac gta gct cat cat ttg ttc cac gag atg cca ttt     1104
Ile Gly Ser Thr His Val Ala His His Leu Phe His Glu Met Pro Phe
                355                 360                 365 tac aag gcg gat gtg gct act gcg tcg atc aag ggt ttc ttg gag ccg     1152
Tyr Lys Ala Asp Val Ala Thr Ala Ser Ile Lys Gly Phe Leu Glu Pro
370                 375                 380 aag gga ctt tac aac tat gat cca acg cct tgg tat gtg gcc atg tgg     1200
Lys Gly Leu Tyr Asn Tyr Asp Pro Thr Pro Trp Tyr Val Ala Met Trp
385                 390                 395                 400 agg gtg gcc aag act tgt cat tat att gag gat gtg gat gga gtt cag     1248
Arg Val Ala Lys Thr Cys His Tyr Ile Glu Asp Val Asp Gly Val Gln
                405                 410                 415 tat tat aag agt ttg gag gat gtg cct ttg aag aag gat gcc aag aag     1296
Tyr Tyr Lys Ser Leu Glu Asp Val Pro Leu Lys Lys Asp Ala Lys Lys
            420                 425                 430 tct gat tag                                                         1305
Ser Asp <210> SEQ ID NO 44
<211> LENGTH: 434
<212> TYPE: PRT
<213> ORGANISM: Thalassiosira pseudonana

<400> SEQUENCE: 44

Met Gly Lys Gly Gly Arg Ser Val Thr Arg Ala Gln Thr Ala Glu Lys
1               5                   10                  15

Ser Ala His Thr Ile Gln Thr Phe Thr Asp Gly Arg Trp Val Ser Pro
                20                  25                  30

Tyr Asn Pro Leu Ala Lys Asp Ala Pro Glu Leu Pro Ser Lys Gly Glu
            35                  40                  45

Ile Lys Ala Val Ile Pro Lys Glu Cys Phe Glu Arg Ser Tyr Leu His
        50                  55                  60
```

```
Ser Met Tyr Phe Val Leu Arg Asp Thr Val Met Ala Val Ala Cys Ala
 65                  70                  75                  80

Tyr Ile Ala His Ser Thr Leu Ser Thr Asp Ile Pro Ser Glu Leu Leu
             85                  90                  95

Ser Val Asp Ala Leu Lys Trp Phe Leu Gly Trp Asn Thr Tyr Ala Phe
        100                 105                 110

Trp Met Gly Cys Ile Leu Thr Gly His Trp Val Leu Ala His Glu Cys
            115                 120                 125

Gly His Gly Ala Phe Ser Pro Ser Gln Thr Phe Asn Asp Phe Trp Gly
        130                 135                 140

Phe Ile Met His Gln Ala Val Leu Val Pro Tyr Phe Ala Trp Gln Tyr
145                 150                 155                 160

Ser His Ala Lys His His Arg Arg Thr Asn Asn Ile Met Asp Gly Glu
                165                 170                 175

Ser His Val Pro Asn Ile Ala Lys Glu Met Gly Leu Asn Glu Lys Asn
            180                 185                 190

Glu Arg Ser Gly Gly Tyr Ala Ala Ile His Glu Ala Ile Gly Asp Gly
        195                 200                 205

Pro Phe Ala Met Phe Gln Ile Phe Ala His Leu Val Ile Gly Trp Pro
    210                 215                 220

Ile Tyr Leu Met Gly Phe Ala Ser Thr Gly Arg Leu Gly Gln Asp Gly
225                 230                 235                 240

Lys Glu Leu Gln Ala Gly Glu Ile Ile Asp His Tyr Arg Pro Trp Ser
                245                 250                 255

Lys Met Phe Pro Thr Lys Leu Arg Phe Lys Ile Ala Leu Ser Thr Leu
            260                 265                 270

Gly Val Ile Ala Ala Trp Val Gly Leu Tyr Phe Ala Ala Gln Glu Tyr
        275                 280                 285

Gly Val Leu Pro Val Val Leu Trp Tyr Ile Gly Pro Leu Met Trp Asn
    290                 295                 300

Gln Ala Trp Leu Val Leu Tyr Thr Trp Leu Gln His Asn Asp Pro Ser
305                 310                 315                 320

Val Pro Gln Tyr Gly Ser Asp Glu Trp Thr Trp Val Lys Gly Ala Leu
                325                 330                 335

Ser Thr Ile Asp Arg Pro Tyr Gly Ile Phe Asp Phe Phe His His Lys
            340                 345                 350

Ile Gly Ser Thr His Val Ala His His Leu Phe His Glu Met Pro Phe
        355                 360                 365

Tyr Lys Ala Asp Val Ala Thr Ala Ser Ile Lys Gly Phe Leu Glu Pro
    370                 375                 380

Lys Gly Leu Tyr Asn Tyr Asp Pro Thr Pro Trp Tyr Val Ala Met Trp
385                 390                 395                 400

Arg Val Ala Lys Thr Cys His Tyr Ile Glu Asp Val Asp Gly Val Gln
                405                 410                 415

Tyr Tyr Lys Ser Leu Glu Asp Val Pro Leu Lys Lys Asp Ala Lys Lys
            420                 425                 430

Ser Asp
```